United States Patent
Keyser et al.

(10) Patent No.: US 10,695,366 B2
(45) Date of Patent: *Jun. 30, 2020

(54) MICROPOROUS ZIRCONIUM SILICATE AND DIURETICS FOR THE REDUCTION OF POTASSIUM AND TREATMENT OF CHRONIC KIDNEY AND/OR CHRONIC HEART DISEASE

(71) Applicant: ZS PHARMA, INC., Coppell, TX (US)

(72) Inventors: Donald Jeffrey Keyser, Southlake, TX (US); Alvaro F. Guillem, Lantana, TX (US)

(73) Assignee: ZS PHARMA, INC., Coppell, TX (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/925,348

(22) Filed: Mar. 19, 2018

(65) Prior Publication Data
US 2018/0271902 A1 Sep. 27, 2018

Related U.S. Application Data

(63) Continuation of application No. 14/782,288, filed as application No. PCT/US2014/032815 on Apr. 3, 2014, now abandoned.
(Continued)

(51) Int. Cl.
*A61K 33/24* (2019.01)
*A61K 45/06* (2006.01)
(Continued)

(52) U.S. Cl.
CPC .............. *A61K 33/24* (2013.01); *A61K 9/16* (2013.01); *A61K 31/4184* (2013.01);
(Continued)

(58) Field of Classification Search
CPC ............ C01B 39/00; A61K 33/24; A61K 9/16
See application file for complete search history.

(56) References Cited

U.S. PATENT DOCUMENTS

| 5,888,472 A | 3/1999 | Bem et al. |
| 5,891,417 A | 4/1999 | Bem et al. |
| (Continued) | | |

FOREIGN PATENT DOCUMENTS

| WO | WO 02/062356 A2 | 8/2002 |
| WO | WO 2012/109590 A2 | 8/2002 |
| (Continued) | | |

OTHER PUBLICATIONS

Clearfield et al. ("On the selectivity regulation of K2ZrSi30 9•H20-type ion exchangers" J. Molecular Structure 470 (1998) 207-213).*
(Continued)

*Primary Examiner* — Kortney L. Klinkel
(74) *Attorney, Agent, or Firm* — Culhane Meadows PLLC; Jeff B. Vockrodt

(57) ABSTRACT

The present invention relates to novel methods of using microporous zirconium silicate to reduce the risk of hyperkalemia and to lower aldosterone levels in the treatment of chronic kidney disease and/or chronic heart disease with therapies comprising diuretics. The invention provides a safe way to reduce the risk of hyperkalemia and to lower aldosterone. The invention also relates to treatment of other conditions that can occur either alone or in connection with hyperkalemia, chronic kidney disease, and/or chronic heart disease.

3 Claims, 29 Drawing Sheets

Dark = ZrO3 (oct), Light = SiO2 (tet), Cations not shown

Related U.S. Application Data

(60) Provisional application No. 61/930,331, filed on Jan. 22, 2014, provisional application No. 61/914,362, filed on Dec. 10, 2013, provisional application No. 61/808,897, filed on Apr. 5, 2013.

(51) Int. Cl.
  *C01B 39/00*   (2006.01)
  *A61K 9/16*    (2006.01)
  *A61K 31/4184* (2006.01)
  *A61K 38/06*   (2006.01)

(52) U.S. Cl.
  CPC .............. *A61K 38/06* (2013.01); *A61K 45/06* (2013.01); *C01B 39/00* (2013.01); *Y02A 50/471* (2018.01); *Y02A 50/475* (2018.01); *Y02A 50/483* (2018.01)

(56) References Cited

U.S. PATENT DOCUMENTS

| | | | |
|---|---|---|---|
| 6,099,737 | A | 8/2000 | Sherman et al. |
| 6,159,505 | A | 12/2000 | Piper |
| 6,332,985 | B1 | 12/2001 | Sherman et al. |
| 6,579,460 | B1 | 6/2003 | Willis et al. |
| 2004/0105895 | A1 | 6/2004 | Ash |
| 2010/0104527 | A1 | 4/2010 | Mansky et al. |
| 2012/0213847 | A1 | 8/2012 | Keyser et al. |

FOREIGN PATENT DOCUMENTS

| | | |
|---|---|---|
| WO | 2010022381 A1 | 2/2010 |
| WO | 2010022383 A2 | 2/2010 |
| WO | WO 2014/011876 A2 | 1/2014 |
| WO | WO 2014/066407 A1 | 5/2014 |

OTHER PUBLICATIONS

International Search Report of PCT/US2014/032815 dated Aug. 20, 2014.

Extended European Search Report issued in European Patent Application No. 14779186.7 dated Nov. 9, 2016.

Office Action issued in Chinese Patent Application No. 201480032064.8 dated Jul. 4, 2017.

Navascues, N., et al., "Reconstruction of umbite framework variants by atomistic simulations using XRD and sorption data", Chemical Engineering and Processing 47, 2008, pp. 1139-1149.

Bortun, A.I., et al., "Hydrothermal Synthesis of Sodium Zirconium Silicates and Characterization of Their Properties", Chem. Mater, 1997, pp. 1984-1864.

Lehnardt, A., et al., "Pathogenesis, diagnosis and management of hyperkalemia", Pediatr Nephrol, 2011, pagers 377-384.

Jani, P.U., et al., "Biliary Excretion of Polystyrene Microspheres with Covalenty Linked FITC Fluorescene after Oral and Parental Administration to Male Wistar Rats", Journal of Drug Testing, 1996, vol. 4, pp. 87-93.

Genet, F., et al., "Hydotermal Synthesis and Recrystallization of Compounds Belonging to the Nasicon Family: Synthesis and Crystallization of Na4Zr2Si3O12", Solid State Ionics 9 & 10, 1983, pp. 891-894.

O'Hagan, D.T., "The intestinal uptake of particles and the implications for drug and antigen delivery", J. Anat, (1996) 189, pp. 477-482.

O'Hagan, D.T., "Intestinal translocation of particulates—implications for drug and antigen delivery", Advanced Drug Delivery Reviews, 5, (1990), pp. 265-285.

Florence, A., "Nanoparticle uptake by the oral route: Fulfilling its potential?", Elsevier, Drug Discovery Today: Technologies, vol. 2, No. 1, 2005, pp. 75-81.

Information on ZS Pharma Website, "An Innovative Technology Platform", URL: [http://web.archive.org/web/20100906213849/http://zspharma.com/index.php?format=feed &type=atom]; published Sep. 6, 2010.

Brown, I.J., et al., "Salt intakes around the world: implications for public health", International Journal of Epidemiology, 2009, 38, pp. 791-813.

Sica, D.A., et al., "Hyperkalemia in Congestive Heart Failure", Pharmacotherapy in Congestive Heart Failure, Mar./Apr. 2001, pp. 97-100.

\* cited by examiner

Dark = ZrO3 (oct), Light = SiO2 (tet), Cations not shown

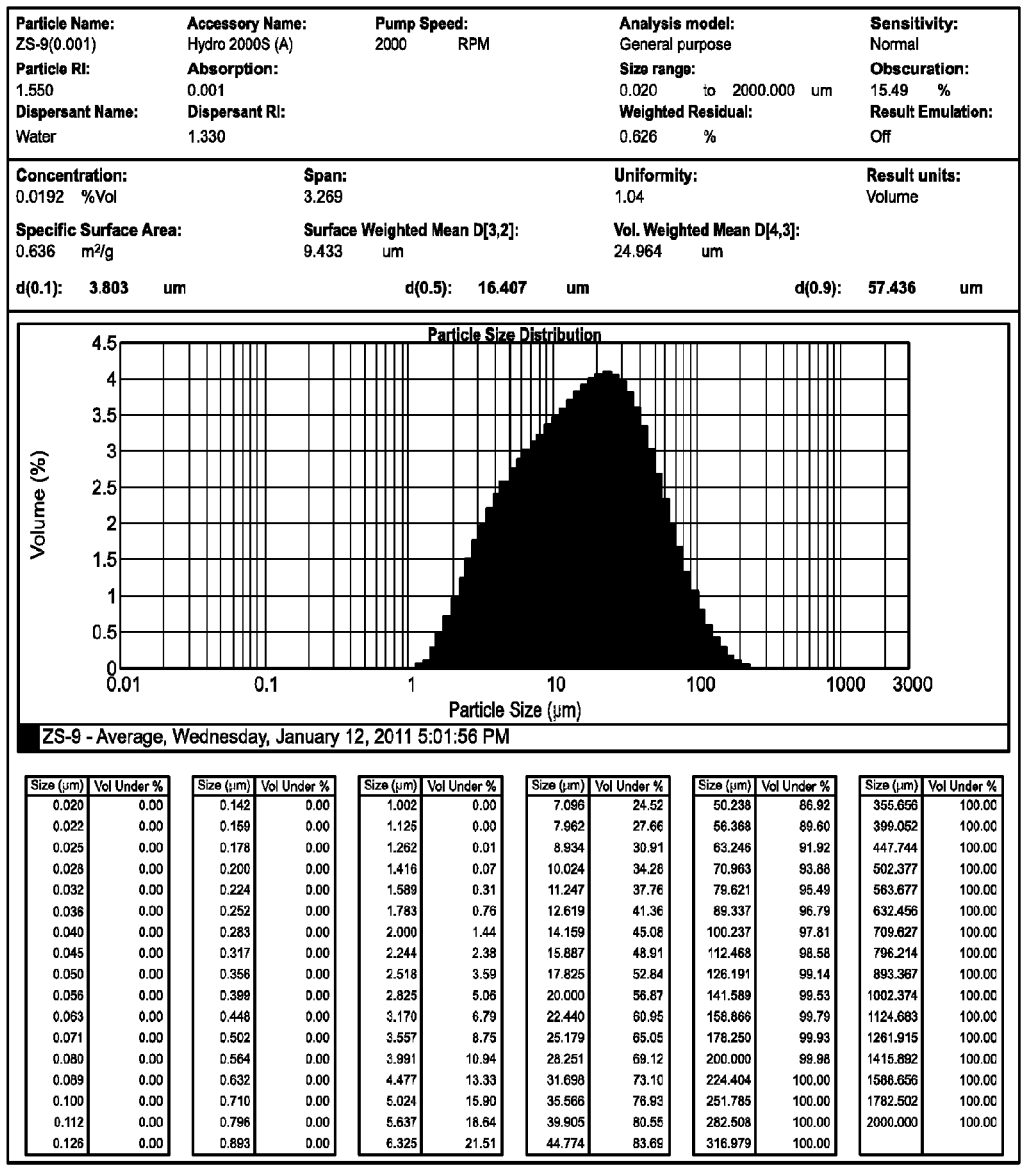
Fig. 2 (ZS-9 lot 5332-04310-A)

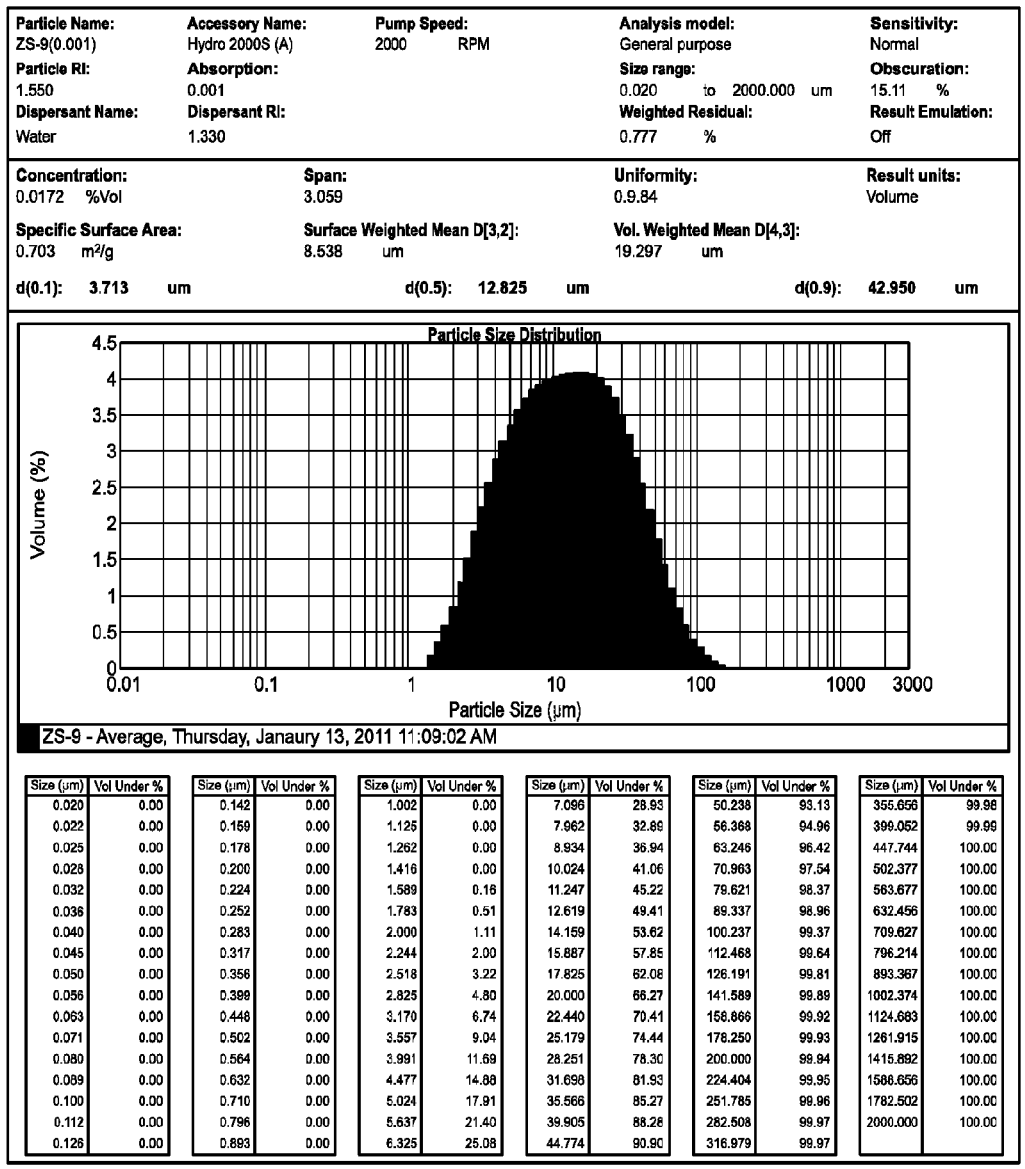
Fig. 3 (ZS-9 lot 5332-15410-A)

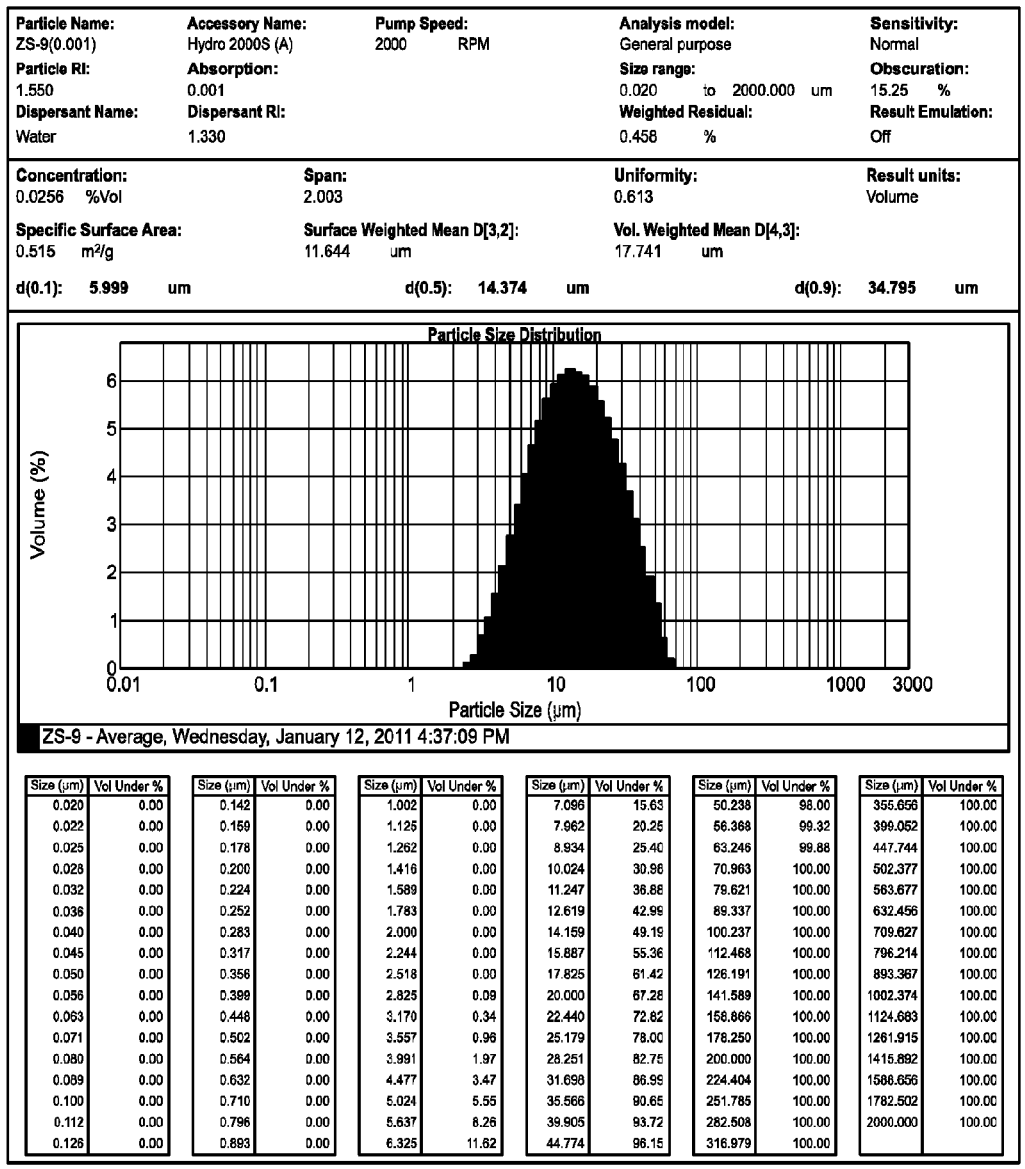
Fig. 4 (ZS-9 preclinical lot)

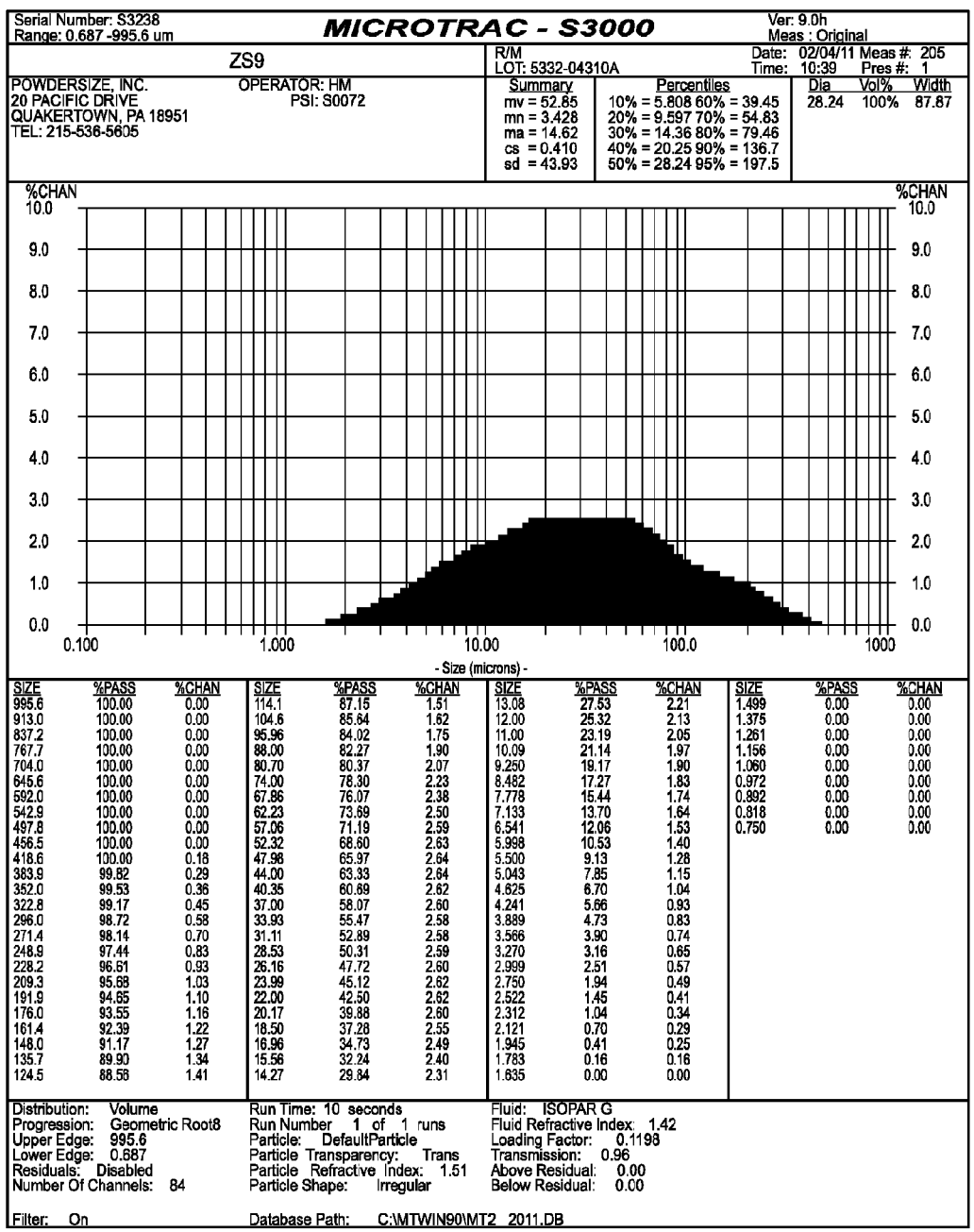
Fig. 5 (lot 5332-04310A w/o screening)

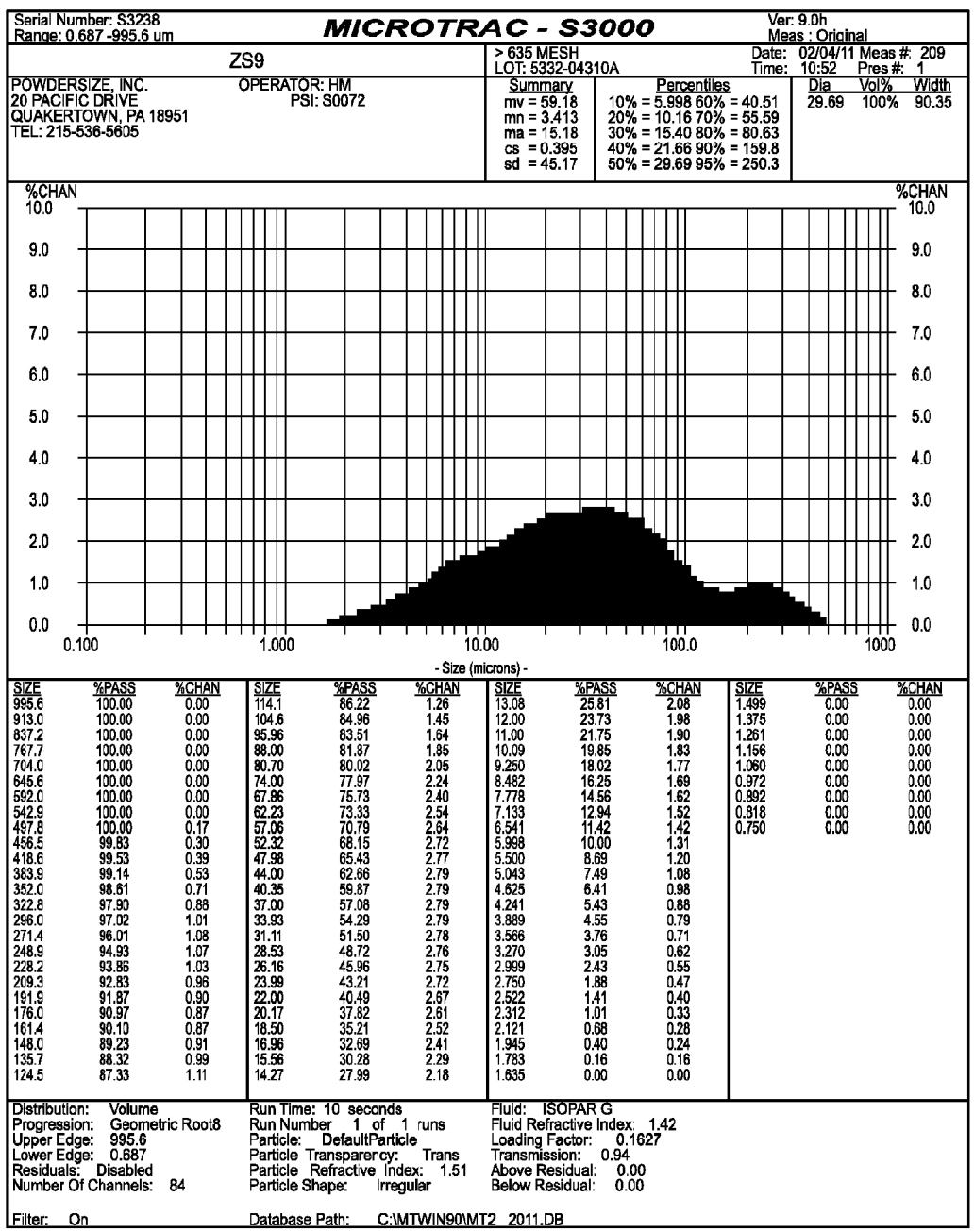
Fig. 6 (lot 5332-04310A 635 mesh)

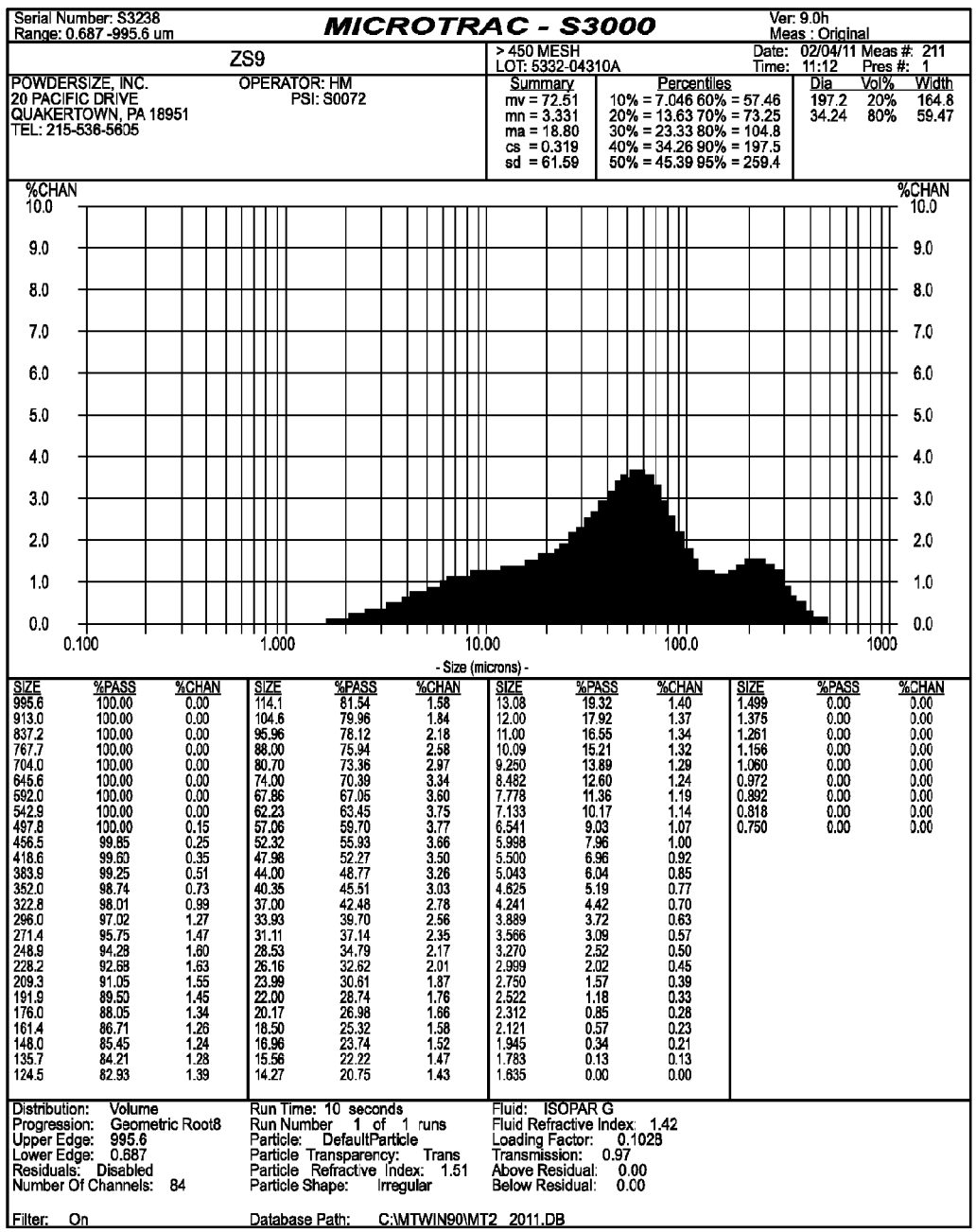
Fig. 7 (lot 5332-04310A 450 mesh)

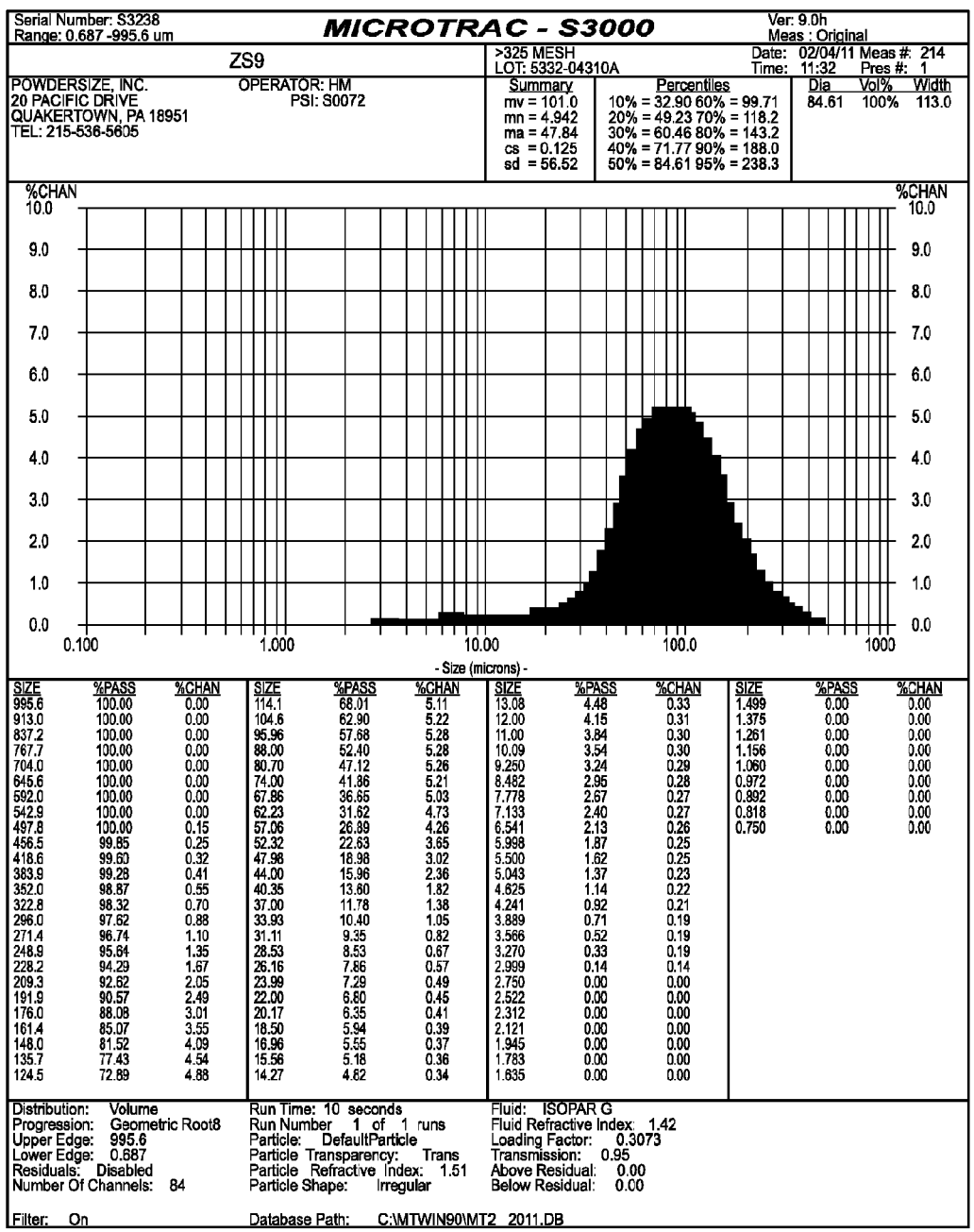
Fig. 8 (lot 5332-04310A 325 mesh)

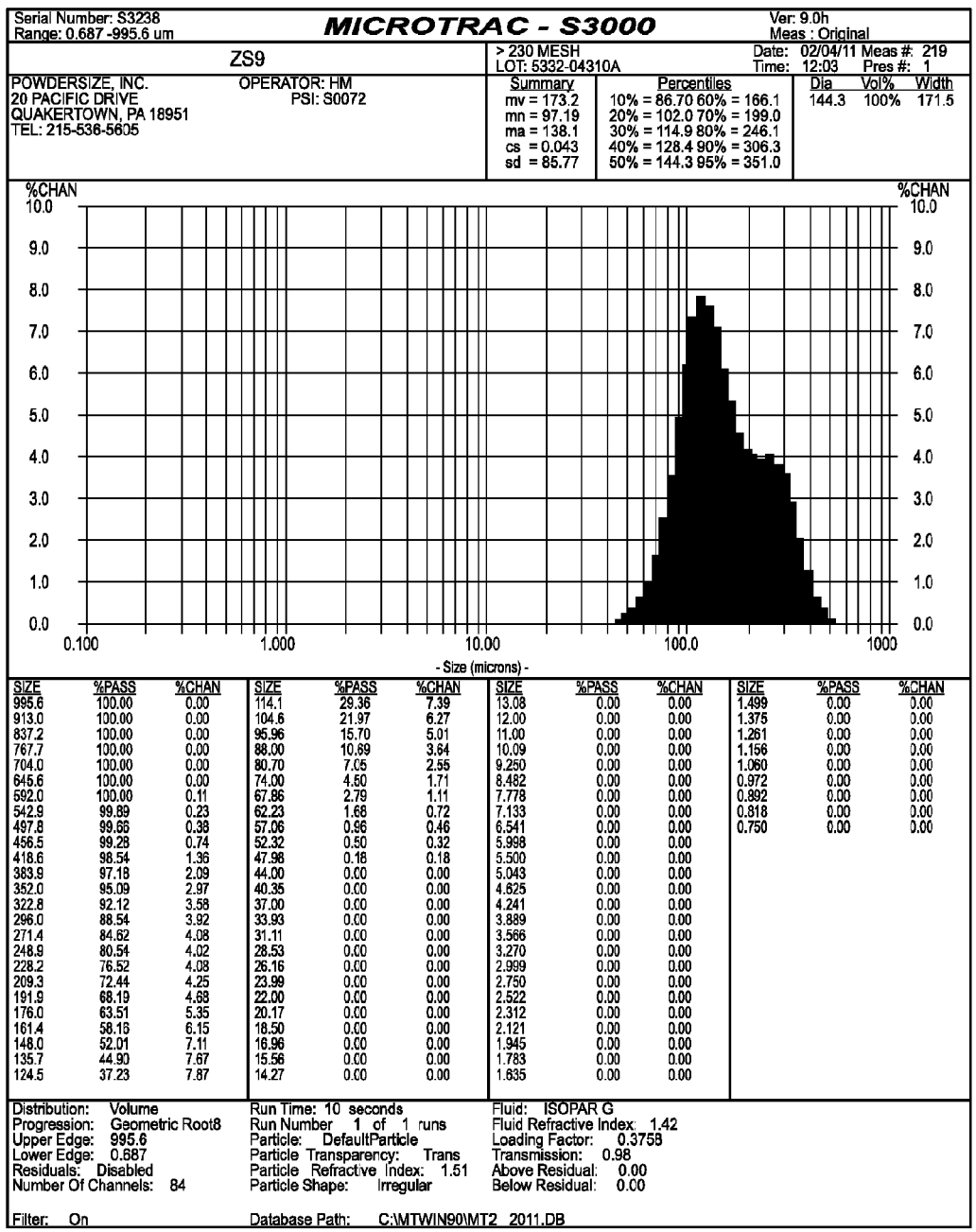
Fig. 9 (lot 5332-04310A 230 mesh)

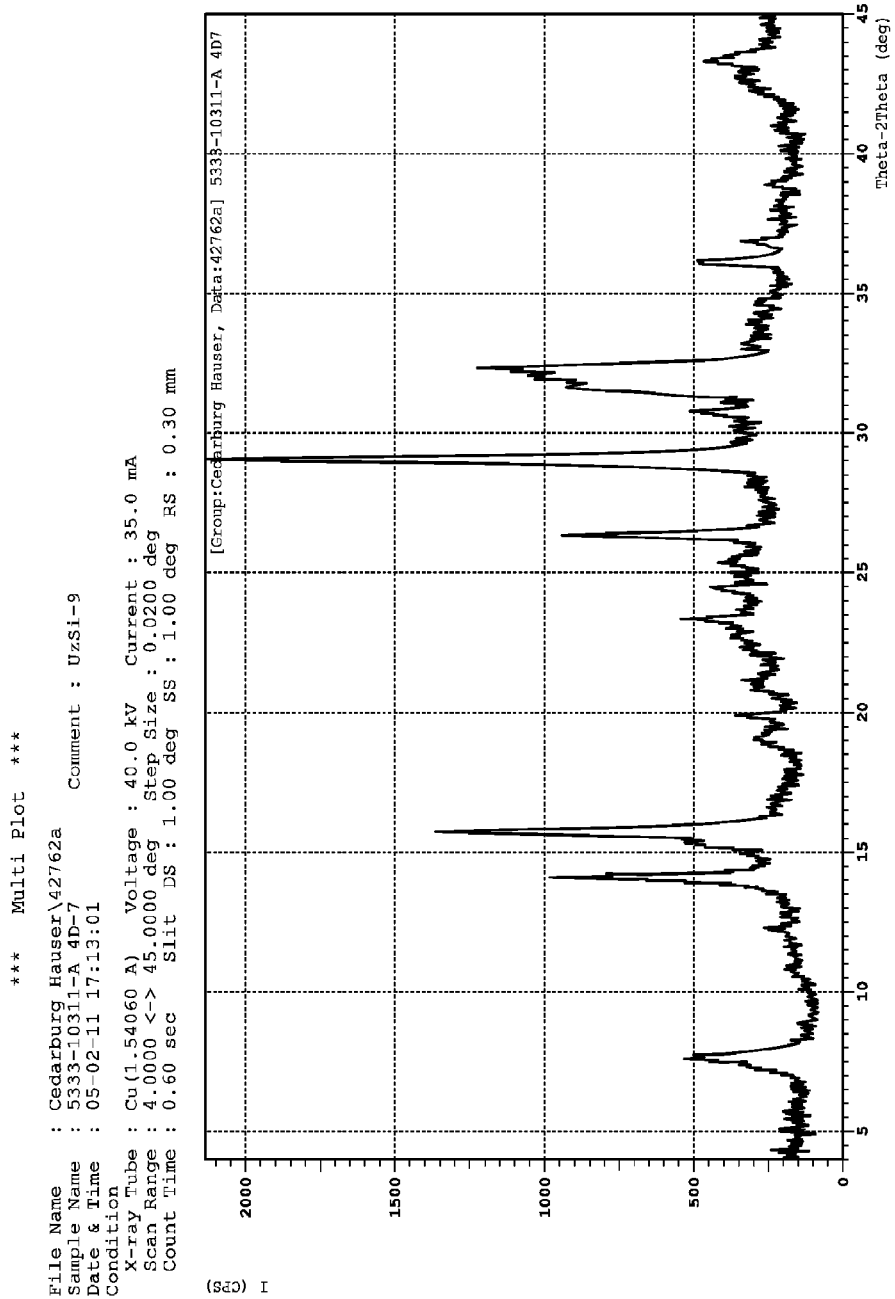
Fig. 10: XRD plot for ZS-9 prepared in accordance with Example 12.

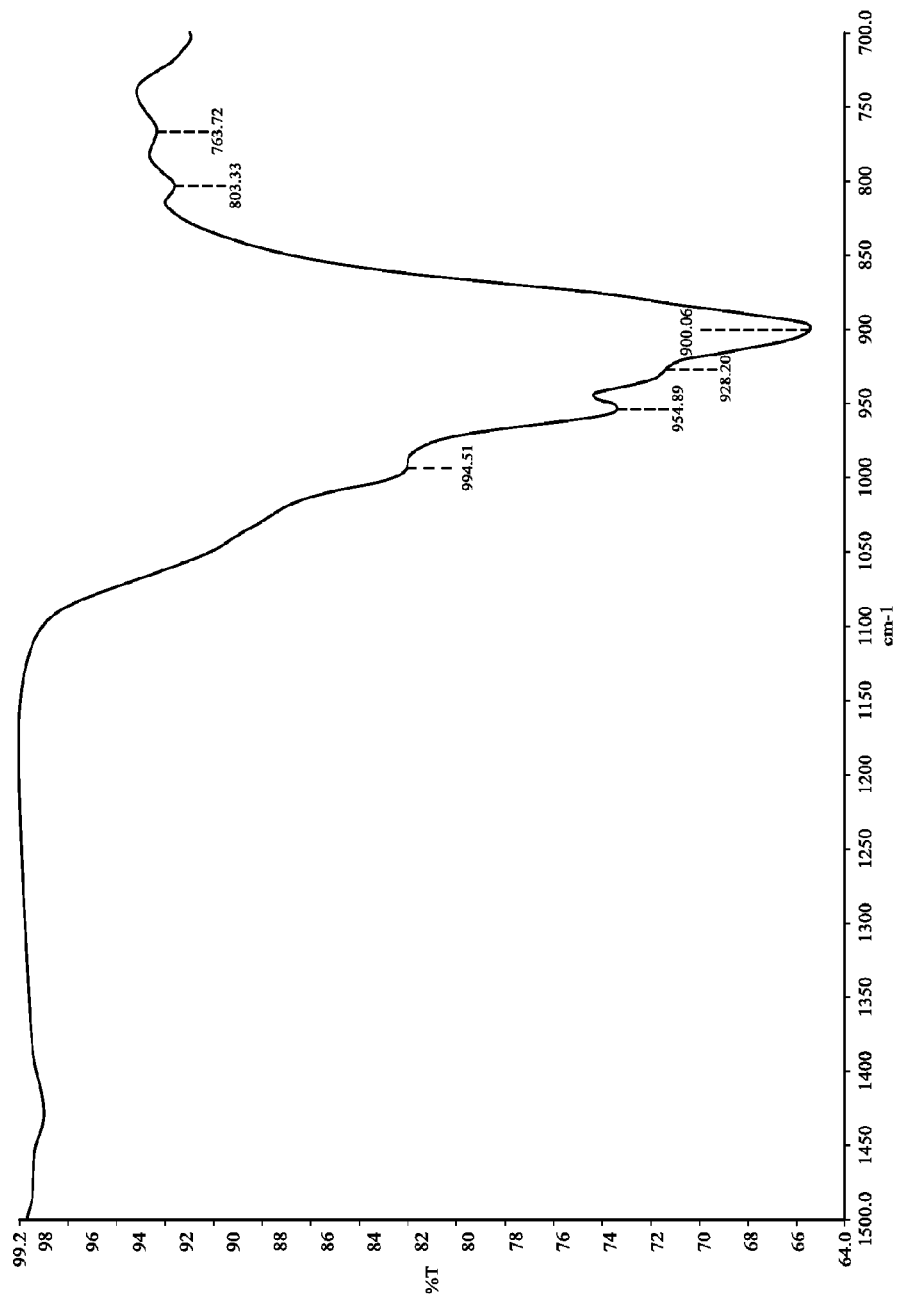
Fig. 11: FTIR plot for ZS-9 prepared in accordance with Example 12.

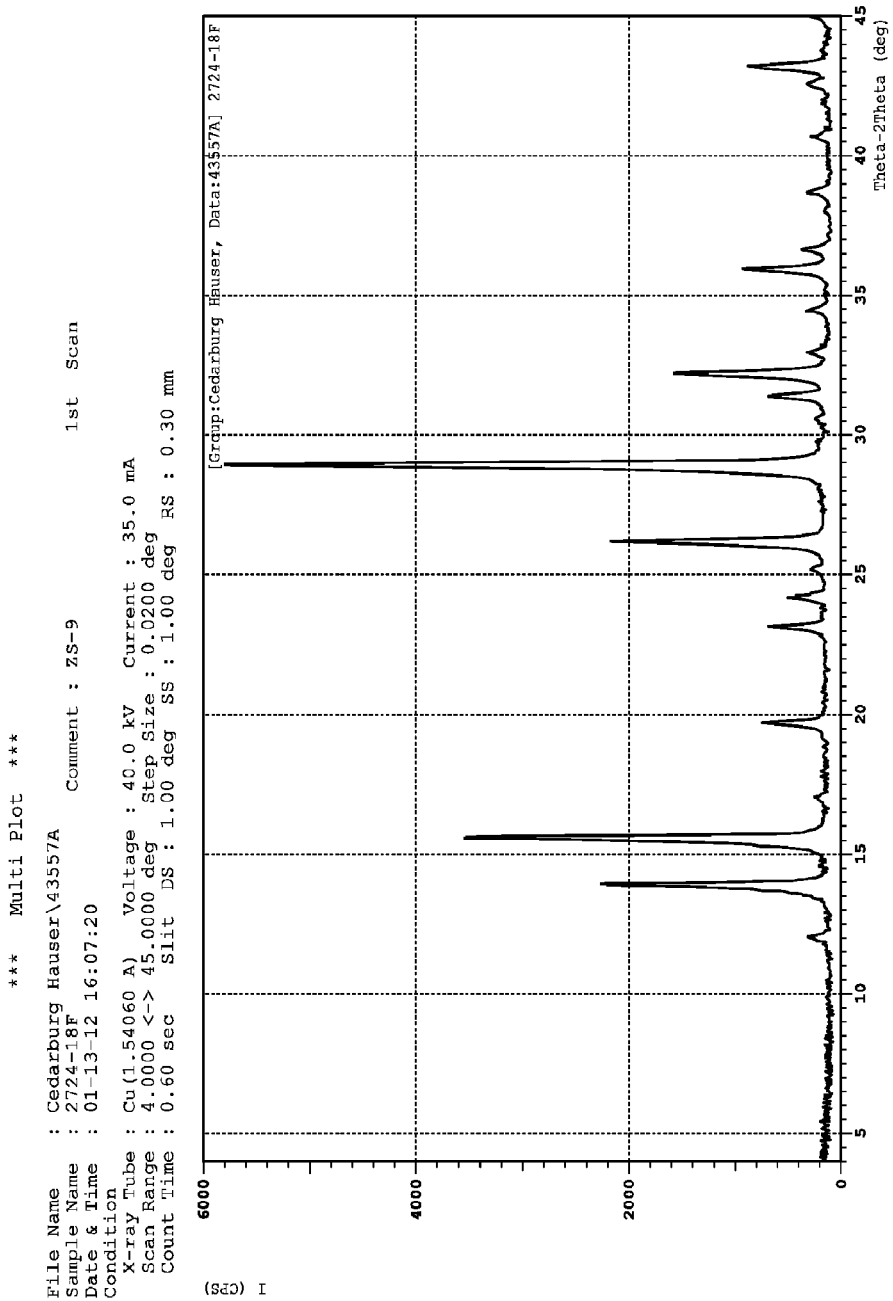
Fig. 12: XRD plot for ZA09 prepared in accordance with Example 14.

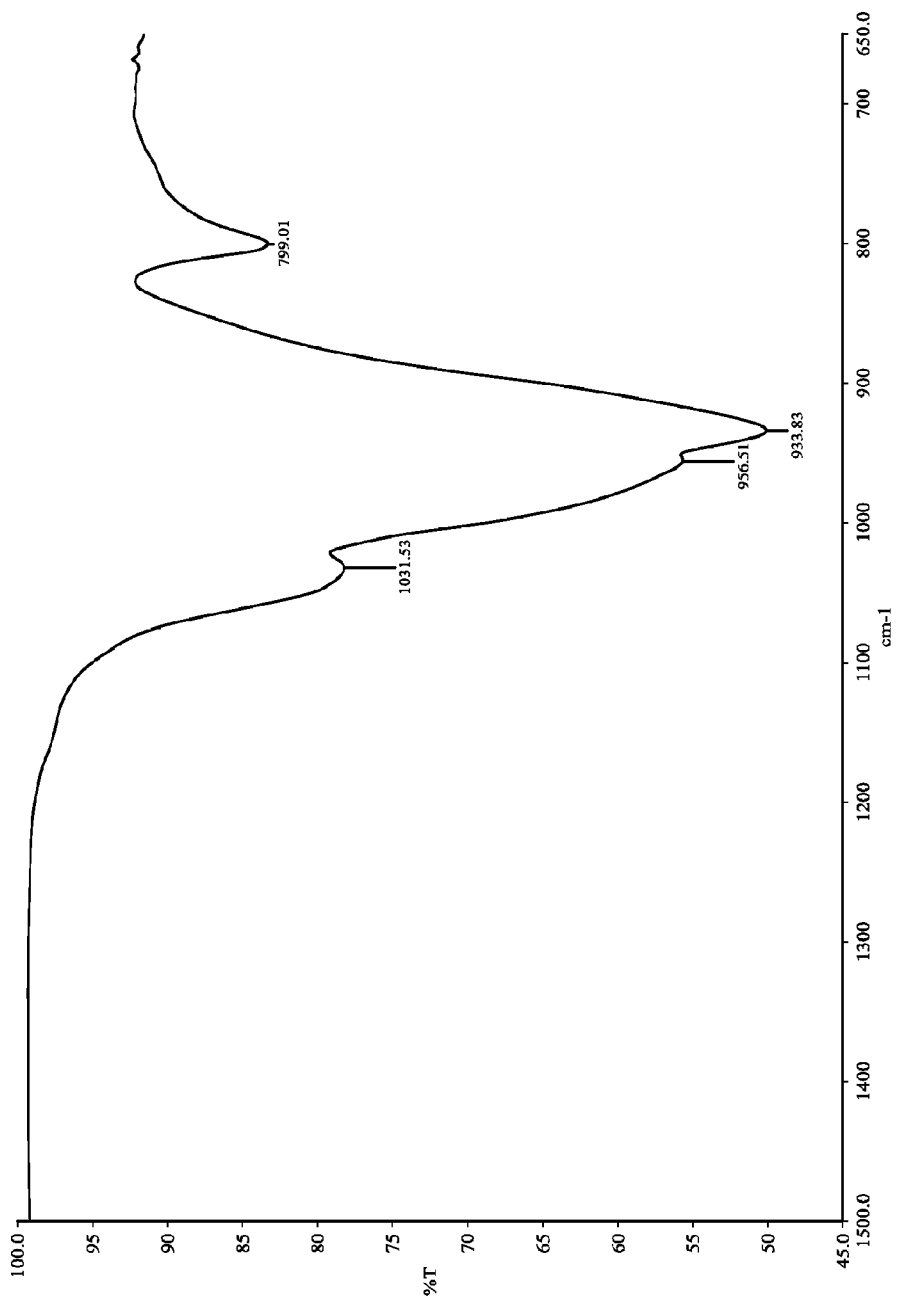
Fig. 13: FTIR plot for ZS09 prepared in accordance with Example 14.

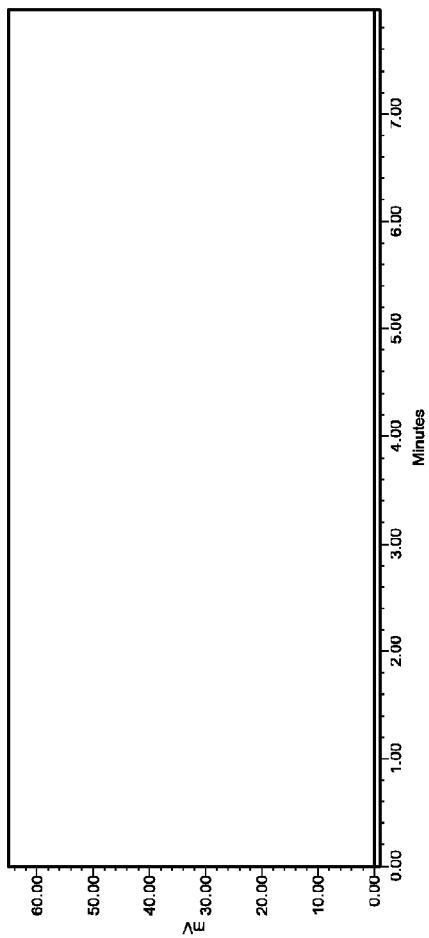
Fig. 14: Example of the Blank Solution Chromatogram
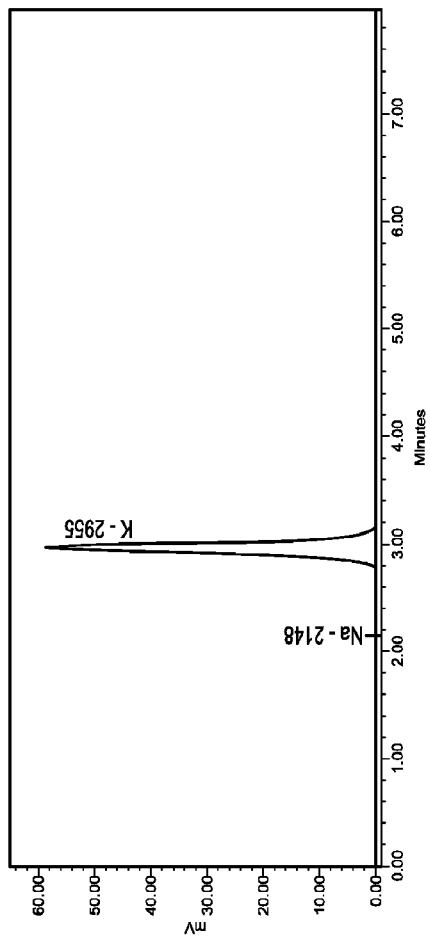
Fig. 15: Example of the Assay Standard Solution Chromatogram.

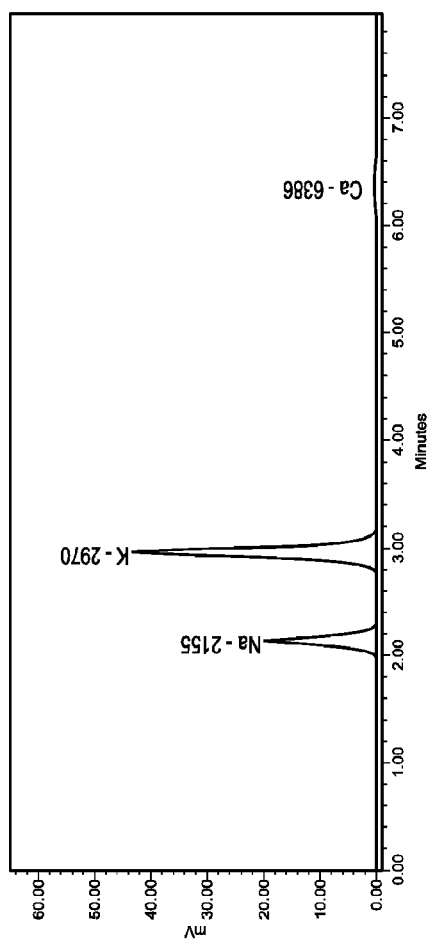
Fig. 16: Exemplary Sample Chromatogram.

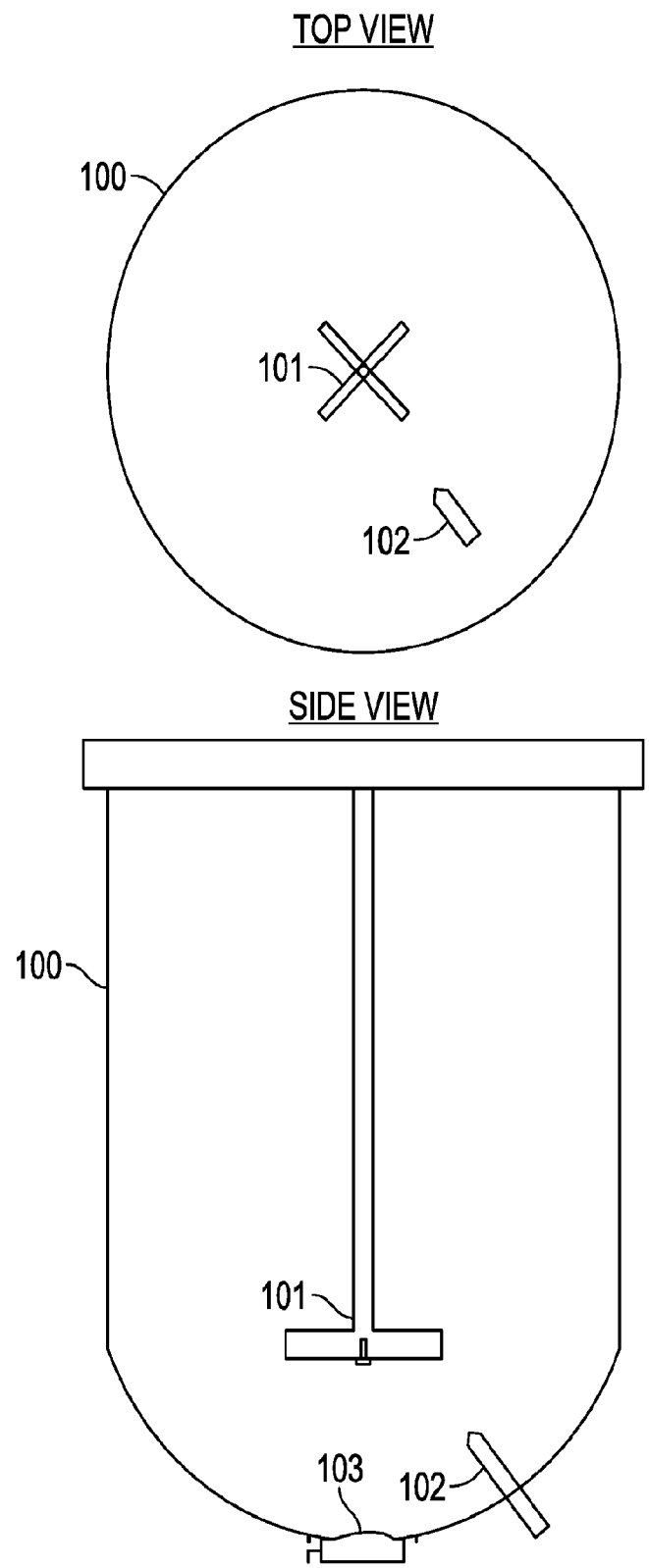
Fig. 17: 200-L reaction vessel with standard agitator arrangement.

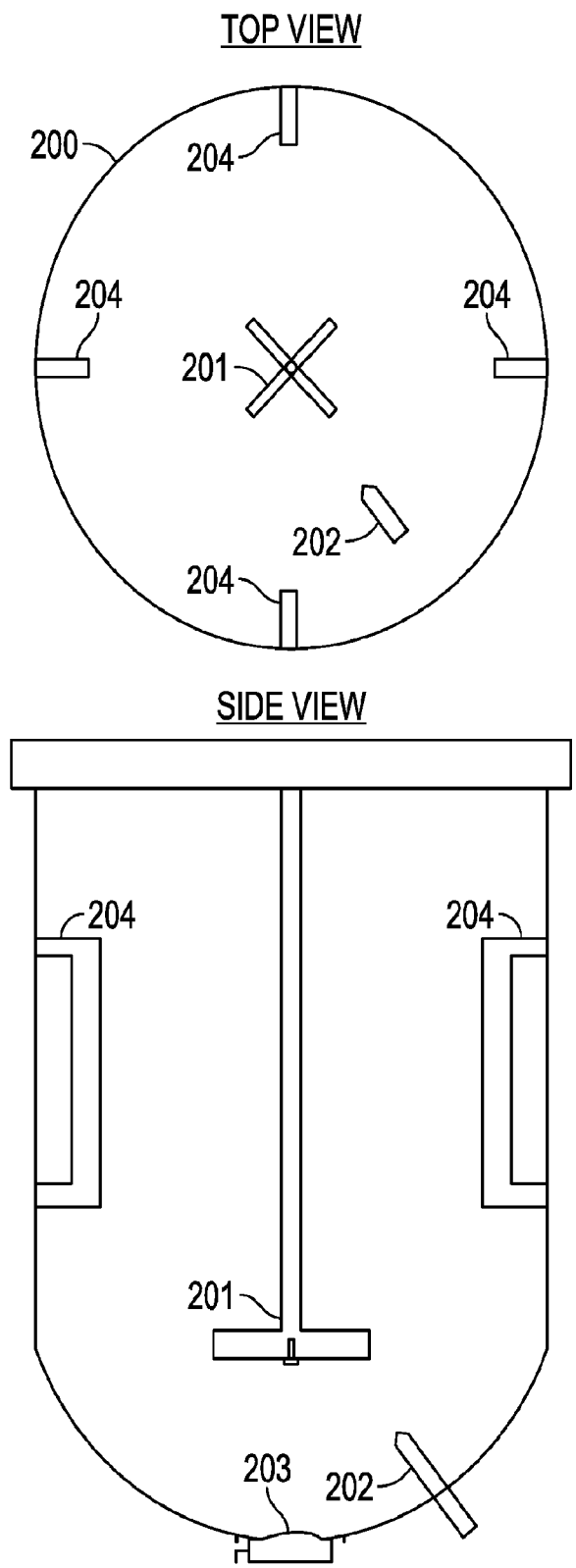
Fig. 18: 200-L reaction vessel with baffles for production of enhanced ZS-9

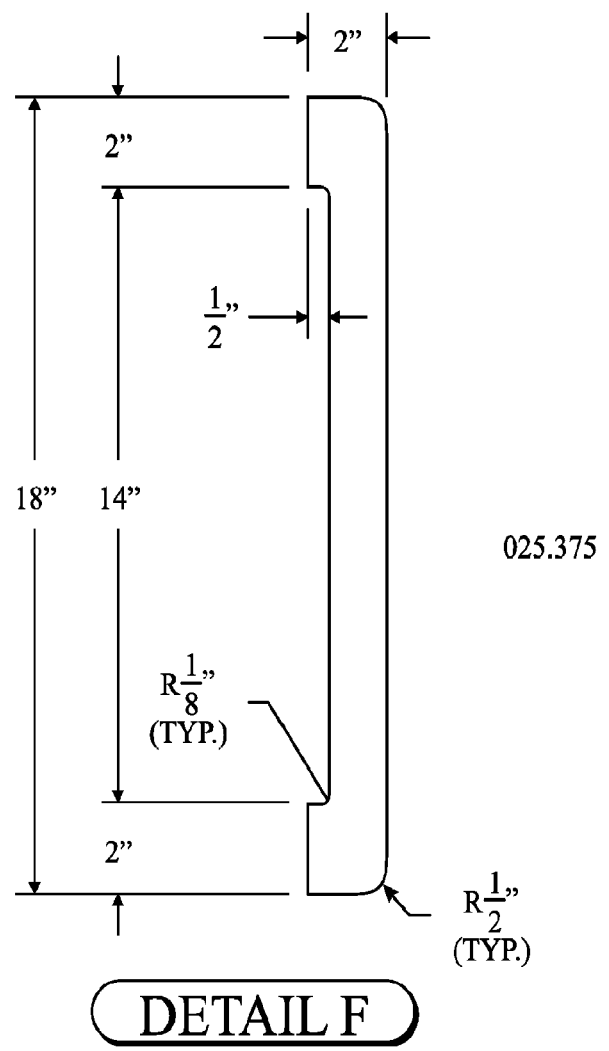
Fig. 19: Detail of baffle design for 200-L reaction vessel for production of enhanced ZS-9

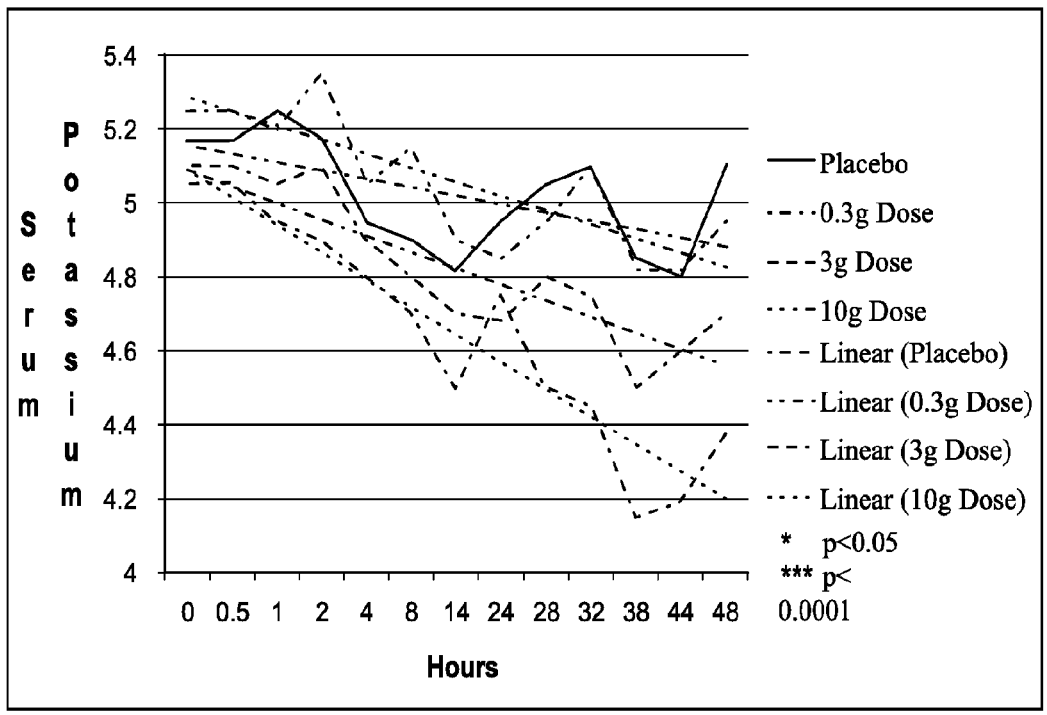
Fig. 20: Serum K levels in the first 48 hours after ingestion of Placebo or ZS
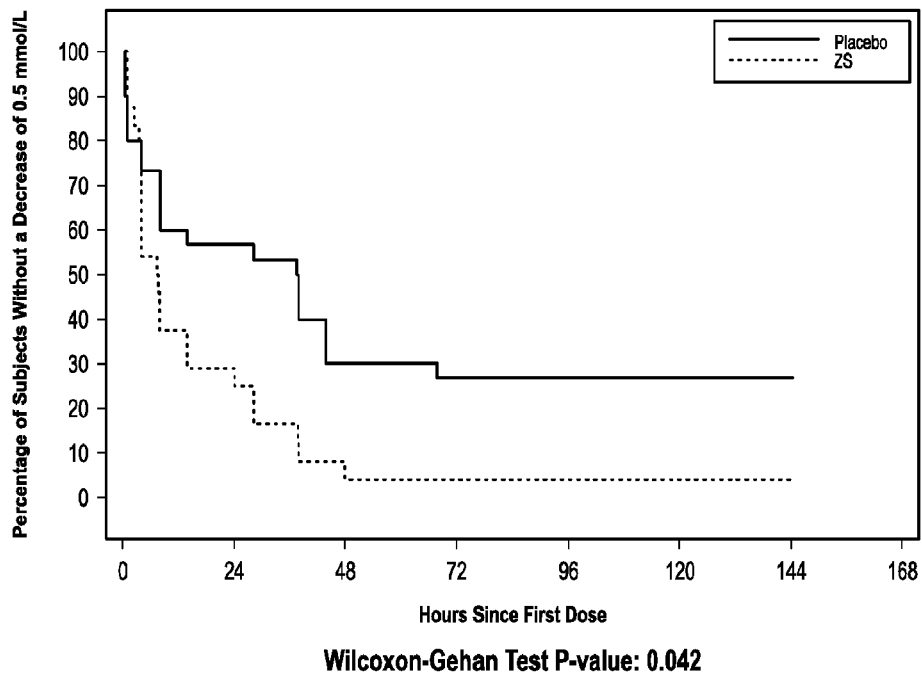
Fig. 21: Time of serum K decrease of placebo vs. ZS at 10 g tib.

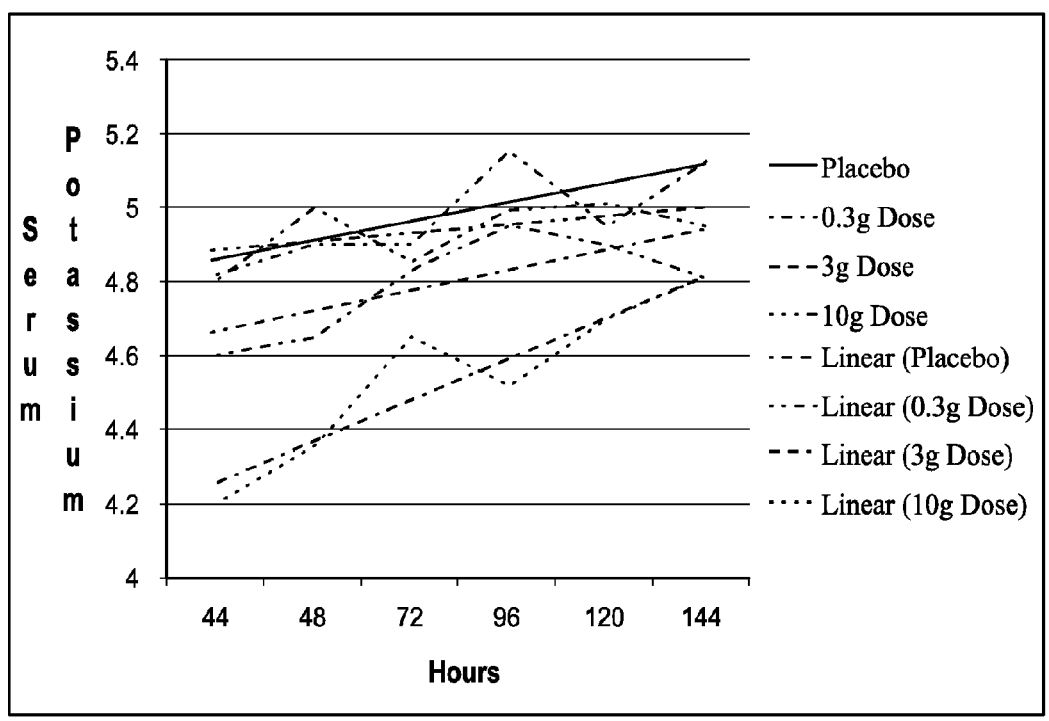
Fig. 22: The rate of serum K increase following ZS administration

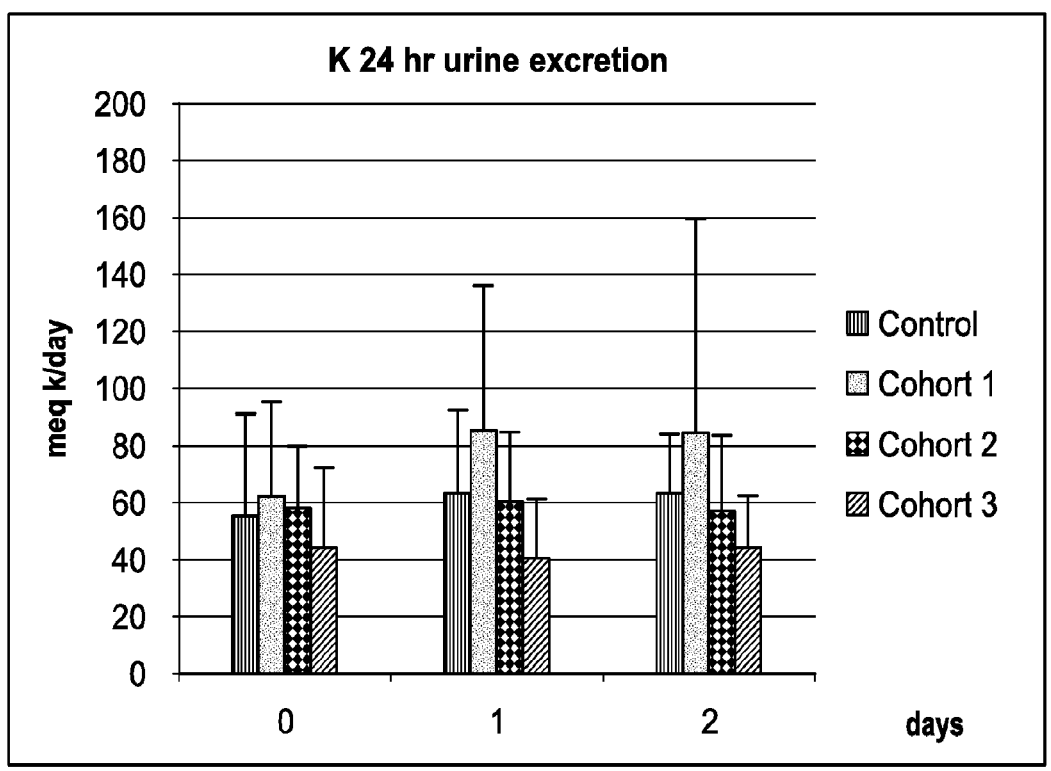
Fig. 23: Rate of urine K excretion

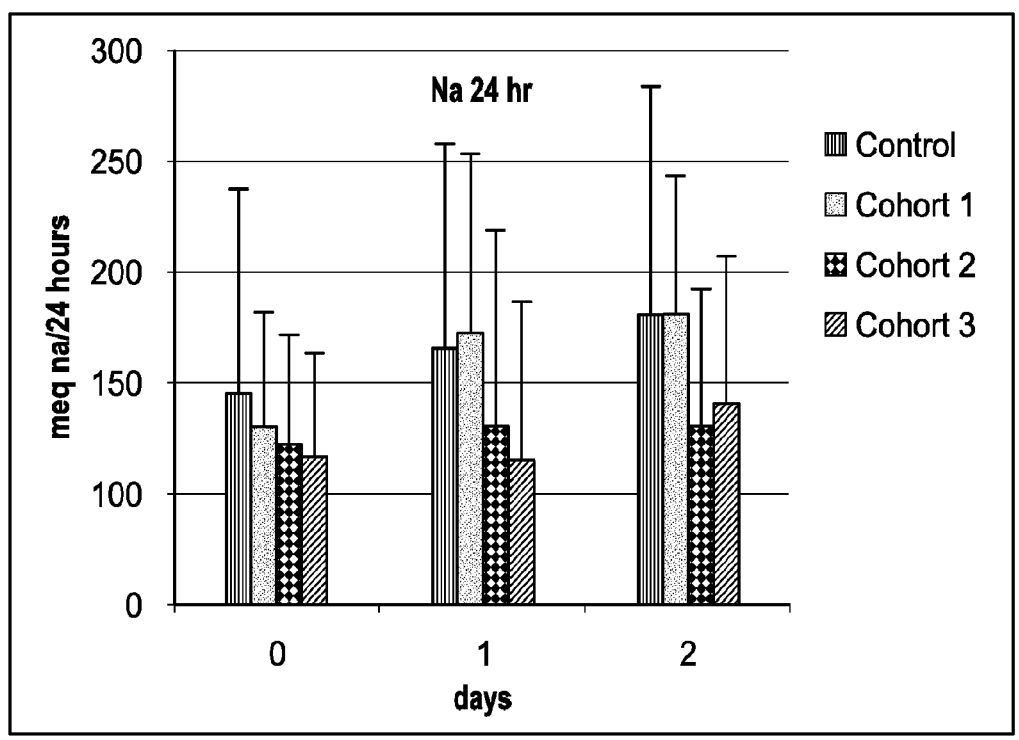
Fig. 24: Daily urinary sodium excretion

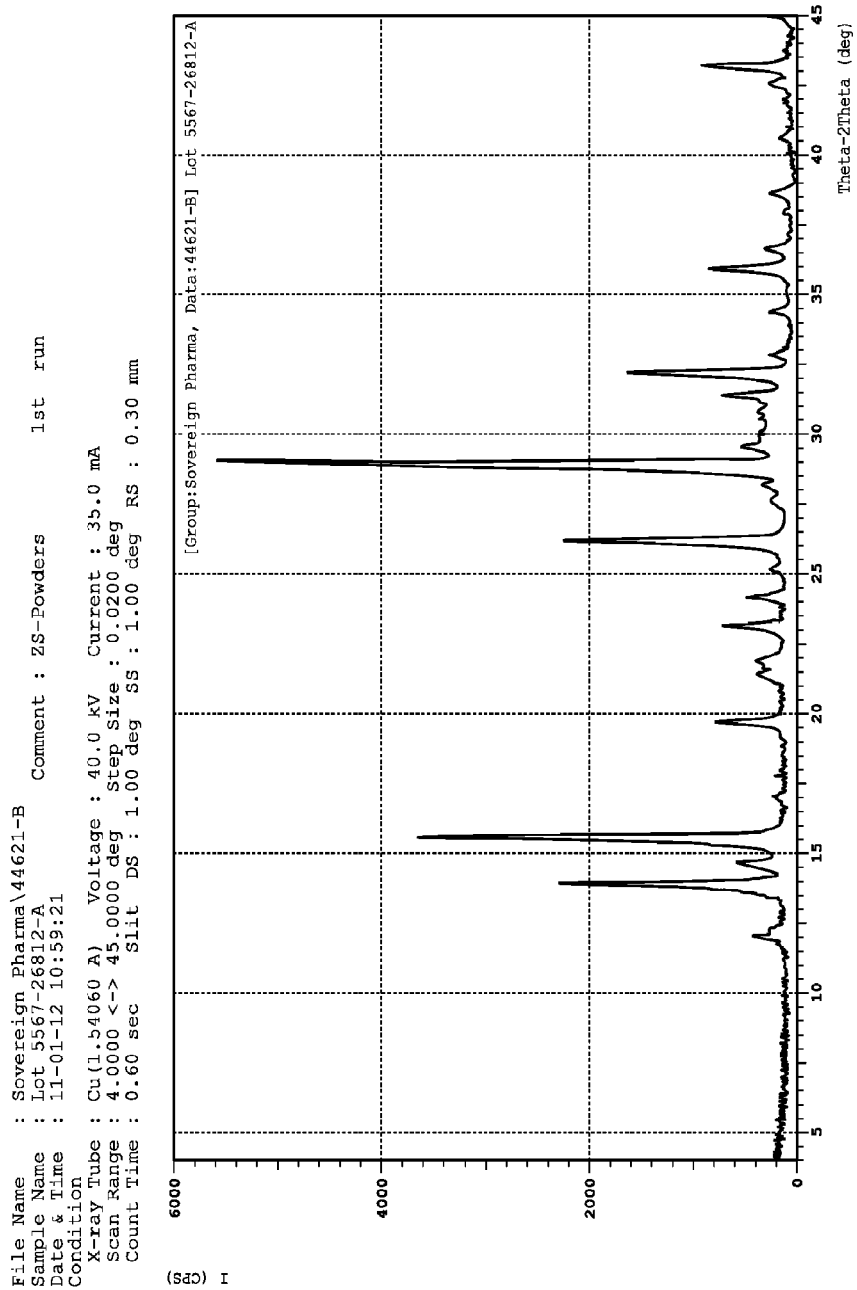
Fig. 25: XRD plot for H-ZS-9 prepared according to Example 20 batch 5602-26812

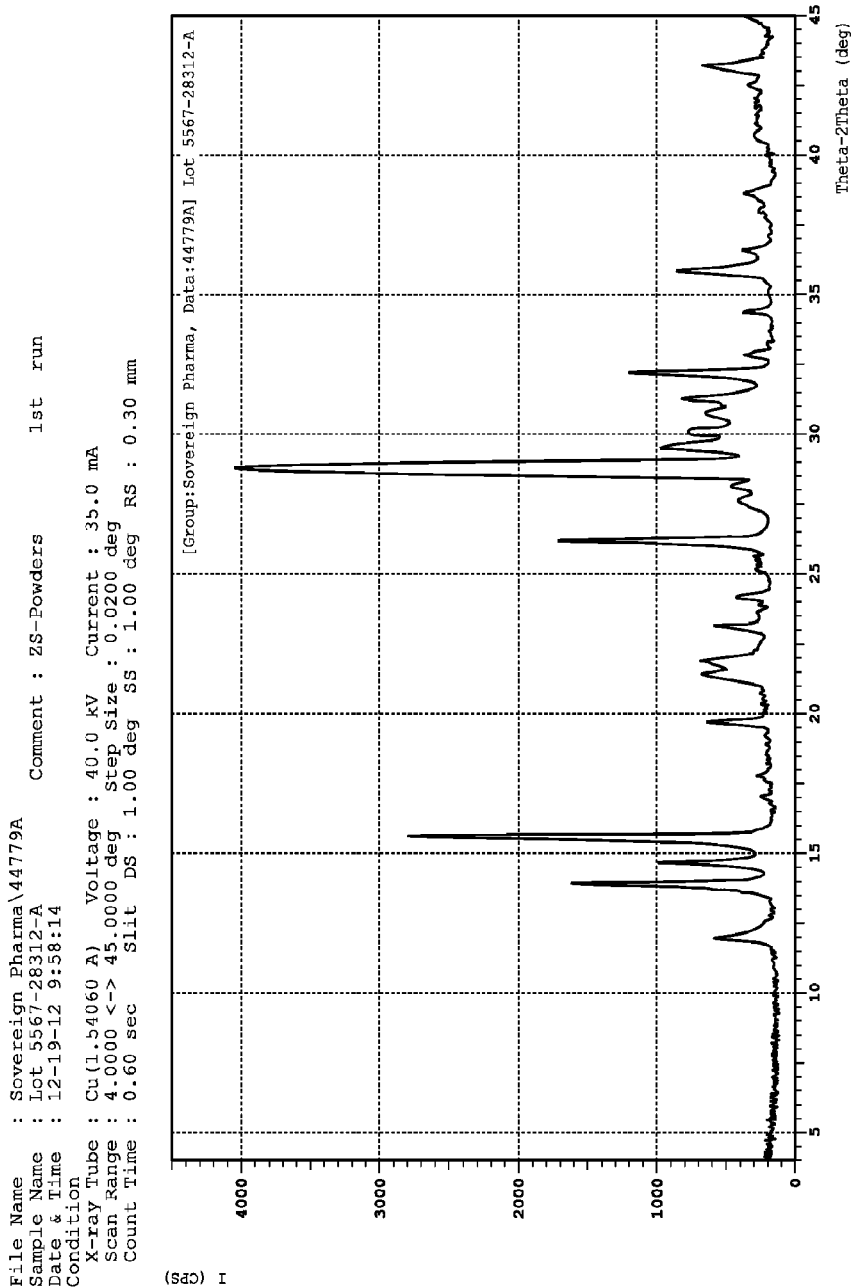
Fig. 26: XRD plot for H-ZS-9 prepared in according to Example 20 batch 5602-28312

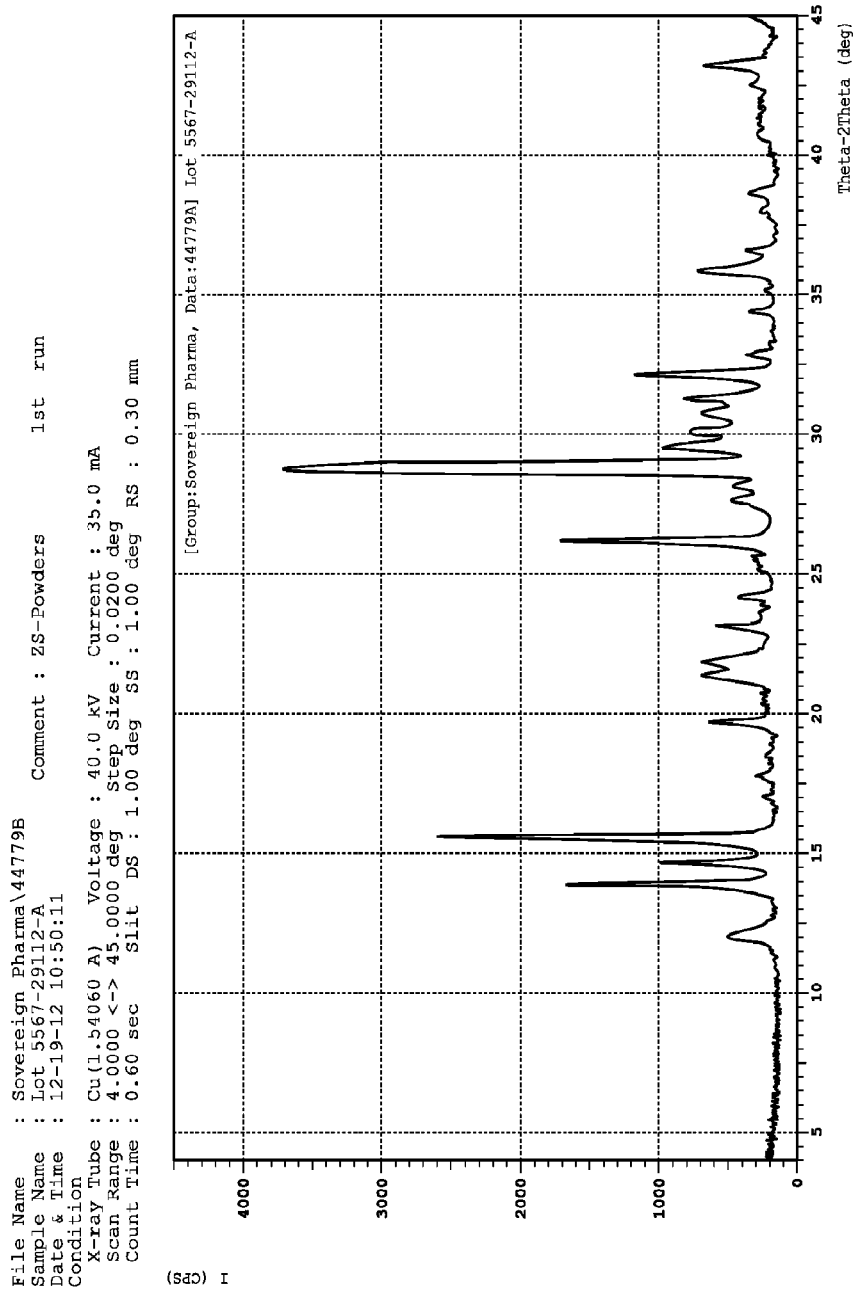
Fig. 27: XRD plot for H-ZS-9 prepared in according to Example 20 batch 5602-29112

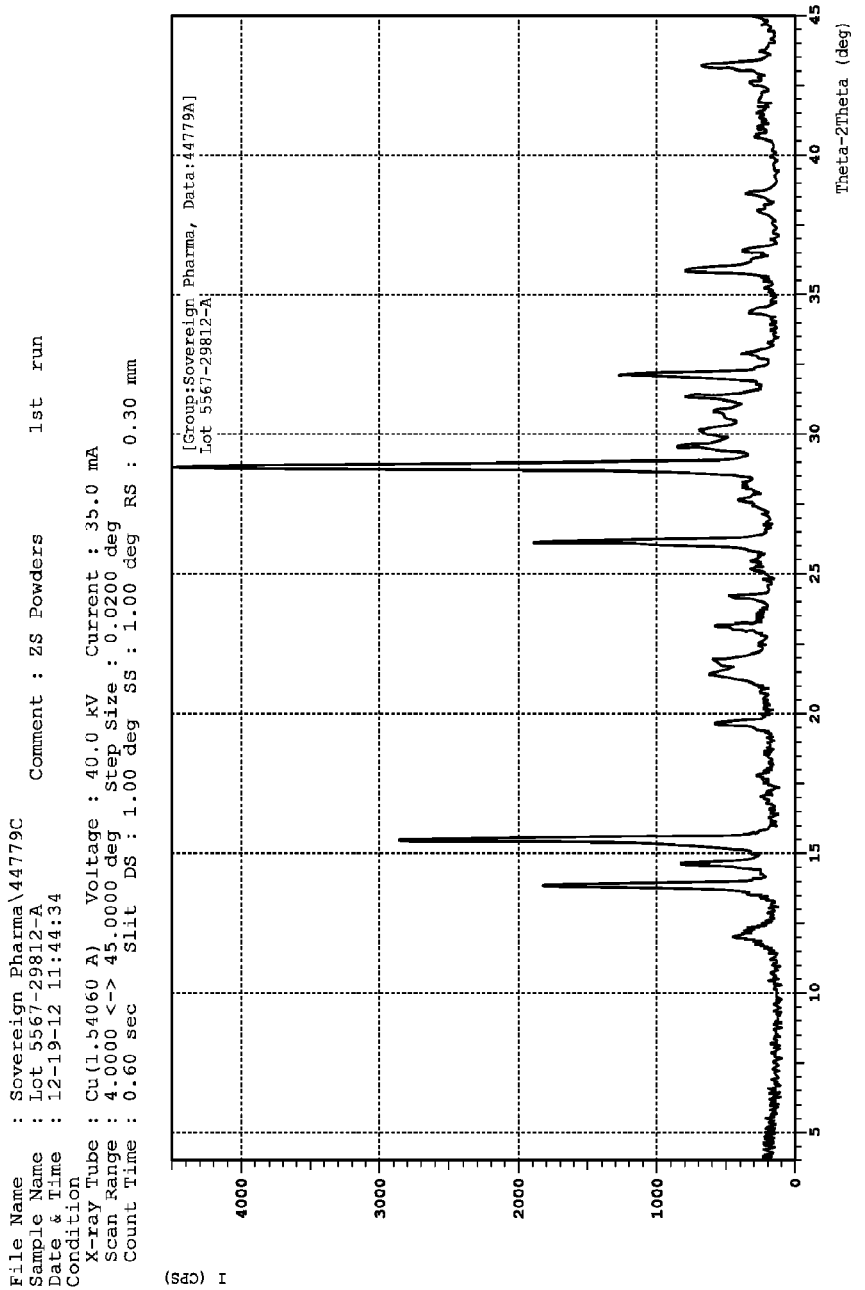
Fig. 28: XRD plot for H-ZS-9 prepared according to Example 20 batch 5602-29812.

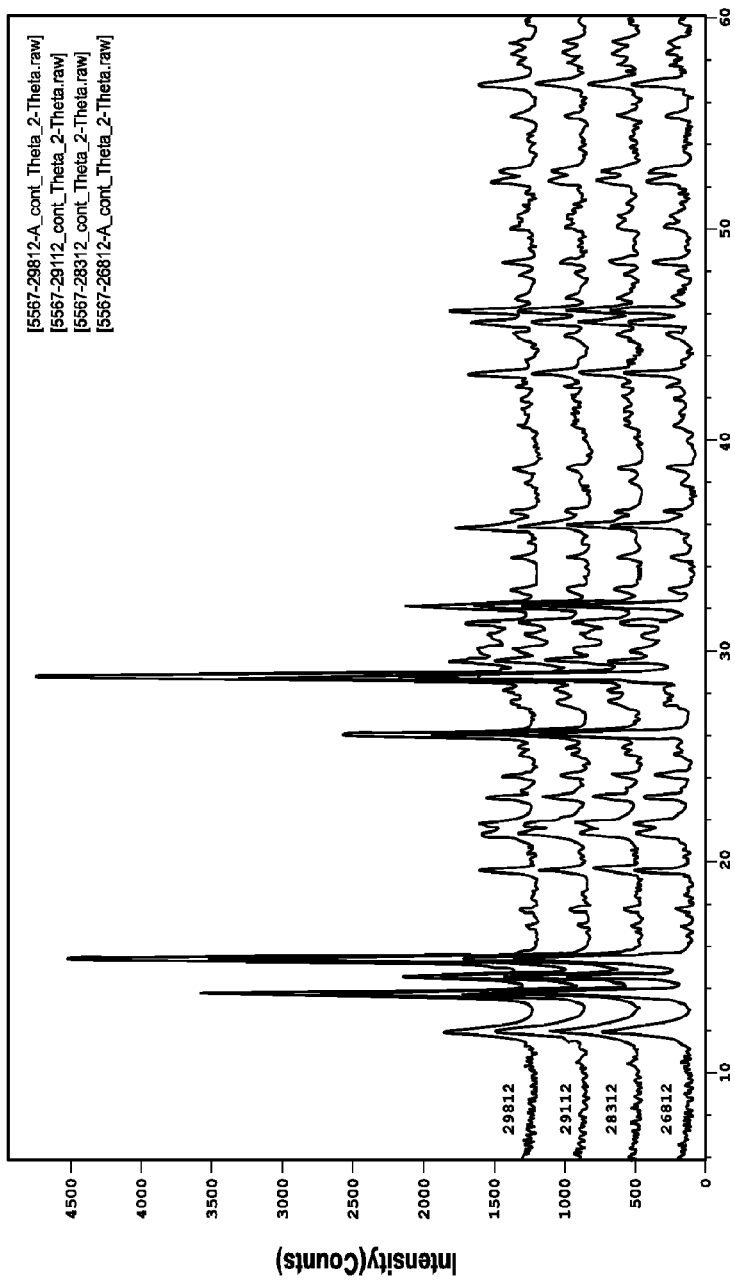
Fig. 29: XRD data for ZS crystals produced accoridng to Example 20.

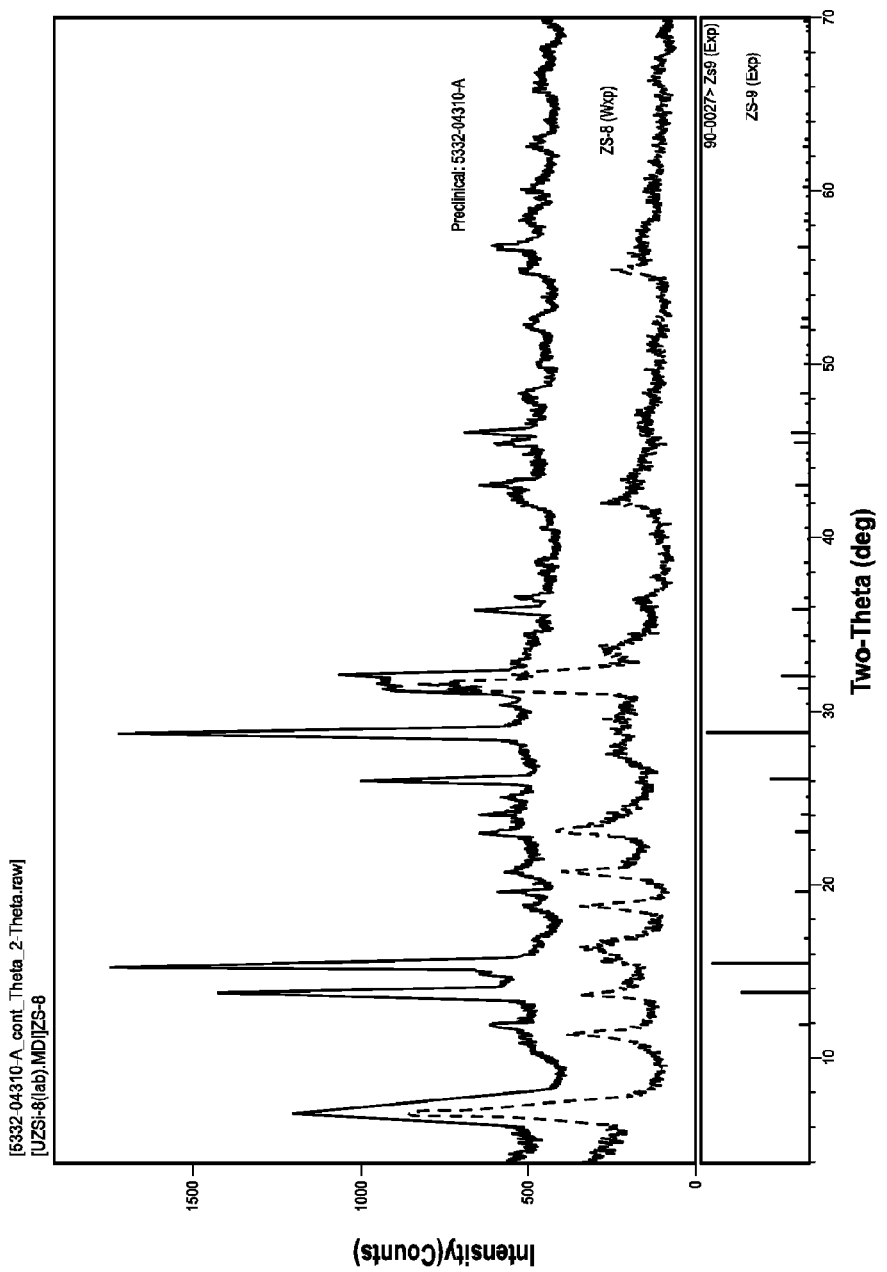
Fig. 30: XRD data ZS-8 impurities.

MICROPOROUS ZIRCONIUM SILICATE AND DIURETICS FOR THE REDUCTION OF POTASSIUM AND TREATMENT OF CHRONIC KIDNEY AND/OR CHRONIC HEART DISEASE

CROSS-REFERENCE TO RELATED APPLICATIONS

This application is a Continuation of U.S. patent application Ser. No. 14/782,288, filed Oct. 2, 2015, which is a National Stage entry of International Application No. PCT/US2014/032815, filed Apr. 3, 2014, which claims priority to U.S. Provisional Application No. 61/808,897, filed Apr. 5, 2013, U.S. Provisional Application No. 61/914,362, filed Dec. 10, 2013, and U.S. Provisional Application No. 61/930,331, filed Jan. 22, 2014, the disclosures of which are hereby incorporated by reference in their entirety.

BACKGROUND OF THE INVENTION

Field of the Invention

The present invention relates to combination therapy and co-therapy methods for the treatment of diseases and/or disorders associated with excess cation levels using microporous zirconium silicate and diuretic compounds. The present invention can be used in the treatment of various disorders associated with excess potassium, including but not limited to hyperkalemia. The present invention can also be used in the treatment of chronic kidney and chronic heart disease. The invention provides a safe way to lower potassium levels in patients prone to or at risk to develop high potassium levels due to the use of therapies that include diuretics. The invention mitigates the negative systemic effects of such therapies without incurring the risk of hyperkalemia. The invention also relates to treatment of other conditions including hyperphosphatemia that can occur either alone or in connection with hyperkalemia, chronic kidney disease, and/or chronic heart disease.

Description of the Related Art

Acute hyperkalemia is a serious life threatening condition resulting from elevated serum potassium levels. Potassium is a ubiquitous ion, involved in numerous processes in the human body. It is the most abundant intracellular cation and is critically important for numerous physiological processes, including maintenance of cellular membrane potential, homeostasis of cell volume, and transmission of action potentials. Its main dietary sources are vegetables (tomatoes and potatoes), fruit (oranges, bananas) and meat. The normal potassium levels in plasma are between 3.5-5.0 mmol/L with the kidney being the main regulator of potassium levels. The renal elimination of potassium is passive (through the glomeruli) with active reabsorption in the proximal tubule and the ascending limb of the loop of Henle. There is active excretion of potassium in the distal tubules and the collecting duct, both of these processes are controlled by aldosterone.

Increased extracellular potassium levels result in depolarization of the membrane potential of cells. This depolarization opens some voltage-gated sodium channels, but not enough to generate an action potential. After a short period of time, the open sodium channels inactivate and become refractory, increasing the threshold to generate an action potential. This leads to impairment of the neuromuscular-, cardiac- and gastrointestinal organ systems, and this impairment is responsible for the symptoms seen with hyperkalemia. Of greatest concern is the effect on the cardiac system, where impairment of cardiac conduction can lead to fatal cardiac arrhythmias such as asystole or ventricular fibrillation. Because of the potential for fatal cardiac arrhythmias, hyperkalemia represents an acute metabolic emergency that must be immediately corrected.

Hyperkalemia may develop when there is excessive production of serum potassium (oral intake, tissue breakdown). Ineffective elimination, which is the most common cause of hyperkalemia, can be hormonal (as in aldosterone deficiency), pharmacologic (treatment with ACE-inhibitors or angiotensin-receptor blockers) or, more commonly, due to reduced kidney function or advanced cardiac failure. The most common cause of hyperkalemia is renal insufficiency, and there is a close correlation between degree of kidney failure and serum potassium ("S-K") levels. In addition, a number of different commonly used drugs cause hyperkalemia, such as ACE-inhibitors, angiotensin receptor blockers, potassium-sparing diuretics (e.g. amiloride), NSAIDs (such as ibuprofen, naproxen, celecoxib), heparin and certain cytotoxic and/or antibiotic drugs (such as cyclosporin and trimethoprim). Finally, beta-receptor blocking agents, digoxin or succinylcholine are other well-known causes of hyperkalemia. In addition, advanced degrees of congestive heart disease, massive injuries, burns or intravascular hemolysis cause hyperkalemia, as can metabolic acidosis, most often as part of diabetic ketoacidosis.

Symptoms of hyperkalemia are somewhat non-specific and generally include malaise, palpitations and muscle weakness or signs of cardiac arrhythmias, such as palpitations, brady-tachycardia or dizziness/fainting. Often, however, the hyperkalemia is detected during routine screening blood tests for a medical disorder or after severe complications have developed, such as cardiac arrhythmias or sudden death. Diagnosis is obviously established by S-K measurements.

Treatment depends on the S-K levels. In milder cases (S-K between 5-6.5 mmol/l), acute treatment with a potassium binding resin (Kayexalate®), combined with dietary advice (low potassium diet) and possibly modification of drug treatment (if treated with drugs causing hyperkalemia) is the standard of care; if S-K is above 6.5 mmol/l or if arrhythmias are present, emergency lowering of potassium and close monitoring in a hospital setting is mandated. The following treatments are typically used:

Kayexalate®, a resin that binds potassium in the intestine and hence increases fecal excretion, thereby reducing S-K levels. However, as Kayexalate® has been shown to cause intestinal obstruction and potential rupture. Further, diarrhea needs to be simultaneously induced with treatment. These factors have reduced the palatability of treatment with Kayexalate®.

Insulin IV (+glucose to prevent hypoglycemia), which shifts potassium into the cells and away from the blood.

Calcium supplementation. Calcium does not lower S-K, but it decreases myocardial excitability and hence stabilizes the myocardium, reducing the risk for cardiac arrhythmias.

Bicarbonate. The bicarbonate ion will stimulate an exchange of K+ for Na+, thus leading to stimulation of the sodium-potassium ATPase.

Dialysis (in severe cases).

The only commercial pharmacologic modality that actually increases elimination of potassium from the body is Kayexalate®; however, due to the need to induce diarrhea, Kayexalate® cannot be administered on a chronic basis, and even in the acute setting, with the accompanying need to induce diarrhea, combined with only marginal efficacy and a foul smell and taste, reduces its usefulness.

The use of ZS or titanium silicate microporous ion exchangers to remove toxic cations and anions from blood or dialysate is described in U.S. Pat. Nos. 6,579,460, 6,099,737, and 6,332,985, each of which is incorporated herein in their entirety. Additional examples of microporous ion exchangers are found in U.S. Pat. Nos. 6,814,871, 5,891,417, and 5,888,472, each of which is incorporated herein in their entirety.

The inventors have found that known ZS compositions may exhibit undesirable effects when utilized in vivo for the removal of potassium in the treatment of hyperkalemia. Specifically, the administration of ZS molecular sieve compositions has been associated with an incidence of mixed leukocyte inflammation, minimal acute urinary bladder inflammation and the observation of unidentified crystals in the renal pelvis and urine in animal studies, as well as an increase in urine pH. Further, known ZS compositions have had issues with crystalline impurities and undesirably low cation exchange capacity.

The inventors disclosed novel ZS molecular sieves to address the problem associated with existing hyperkalemia treatments, and novel methods of treatment for hyperkalemia utilizing these novel compositions. See U.S. patent application Ser. No. 13/371,080 (U.S. Pat. Application Pub. No. 2012-0213847 A1). In addition, the present inventors have disclosed novel processes for producing ZS absorbers with an improved particles-size distribution that can be prepared with methods avoid and/or reduce the need to screen ZS crystals. See U.S. Provisional Application No. 61/658,117. Lastly, the present inventors have disclosed novel divalent cation (e.g., calcium and/or magnesium) loaded forms of ZS that are particularly beneficial for treating patients with hypocalcemia who are suffering from hyperkalemia. See U.S. Provisional Application No. 61/670,415. The calcium loaded forms of ZS disclosed in the '415 provisional may include magnesium in addition or as a substitute for calcium. Each of these disclosures is incorporated herein by reference in its entirety.

The inventors previously disclosed that delivery of ZS in the treatment of hyperkalemia can be improved by the use of novel dosage forms. See U.S. Provisional Application Nos. 61/716,956 filed Oct. 22, 2012 and 61/800,182 filed Mar. 15, 2013. Specifically, the inventors have found that specific dosages of the ZS, when administered to a subject suffering from elevated levels of potassium, are capable of significantly decreasing the serum potassium levels in patients with hyperkalemia to normal levels. The inventors have also found that these specific dosages are capable of sustaining the lower potassium levels in patients for an extended period of time.

The role of aldosterone in kidney function has been extensively studied. See Remuzzi et al., "The role of renin-angiotensin-aldosterone system in the progression of chronic kidney disease," Kidney Intl, Vol. 68 Supp. 99, pp. S57-S65 (2005); Zhang et al., "Aldosterone induces epithelial-mesenchymal transition via ROS of mitochondrial origin," Am J Physiol Renal Physiol 293 (2007); Ponda et al., "Aldosterone Antagonism in Chronic Kidney Disease," Clin J Am Soc Nephol 1:668-677 (2006); U. Wenzel, "Aldosterone and Progression of Renal Disease," Current Opinion in Nephrology and Hypertension 17:44-50 (2008); Remuzzi et al., "The Aggravating Mechanisms of Aldosterone on Kidney Fibrosis," J Am Soc Nephrol 19:1459-1462 (2008); Navaneethan et al., "Aldosterone Antagonists for Preventing the Progression of Chronic Kidney Disease: A Systematic Review and Meta-analysis," Am Soc Neph (2008); Briet et al., "Aldosterone: effects on the kidney and cardiovascular system," Nature Reviews: Nephrology 6:261-273 (2010); R Toto, "Aldosterone blockade in chronic kidney disease: can it improve outcome?" Current Opinion in Nephrology and Hypertension 19:444-449 (2010); Turner et al., "Treatment of chronic kidney disease," Kidney Int'l 81:351-362 (2012). As noted by Turner et al., recognition of the deleterious effects of aldosterone has led to attempts to selectively block it using the mineralocorticoid receptor blockers. A large number of animal studies support this approach, and human studies have shown a reduction in proteinuria when aldosterone blockade was added to an ACE inhibitor or ARB. However, this approach has frequently led to hyperkalemia. Thus, there exists a need to treat CKD by lowering aldosterone levels in a way that leads to improved GFR without the onset of hyperkalemia.

The role of aldosterone in cardiovascular disease (CVD) has been extensively studied. Rocha et al., "Selective Aldosterone Blockade Prevents Angiotensin II/Salt-Induced Vascular Inflammation in the Rat Heart," Endocrinology 143 (12):4828-4836 (2002); Rocha et al., "Aldosterone Induces a Vascular Inflammatory Phenotype in the Rat Heart," Am J Phsiol Heat Circ Physiol 283:H1802-H1810 (2002); Briet et al., "Aldosterone: effects on the kidney and cardiovascular system," Nature Reviews: Nephrology 6:261-273 (2010); Tomaschitz et al., "Plasma aldosterone levels are associated with increased cardiovascular mortality: the Ludwigshafen Risk and Cardiocascular Health (LURIC) study," European Heart Journal 31:1237-1247 (2010). Notably, CVD is well known to be common and often fatal in people with CKD. As discussed by Tomachitz et al., plasma aldosterone levels are associated with increased cardiovascular morality. Accordingly, reduction of aldosterone levels without side effects associated with aldo blockers would be desirably in the treatment of patients diagnosed with CKD and/or CVD.

Patients suffering from moderate to severe heart failure and/or renal failure are often administered a combination therapy of ACE inhibitors or ARB and a diuretic (e.g., potassium sparing). The administration of this combination has been shown to increase the risk of developing hyperkalemia, especially in patients with diabetes mellitus and renal impairment. Horn and Hansten, "Hyperkalemia Due to Drug Interactions," Pharmacy Times, pp. 66-67, January 2004; Desai "Hyperkalemia Associated with Inhibitors of the Renin-Angiotensin-Aldosterone System: Balancing Risk and Benefit," Circulation, 118:1609-1611 (2008) Therefore, there is a need to provide patients who are currently on this combination therapy with a means of lower the serum potassium levels without halting the treatment.

SUMMARY OF THE EMBODIMENTS OF THE INVENTION

The present inventors have discovered that administration of preferred forms of microporous zirconium silicate is associated with an improved GFR and when co administered with therapies that include diuretics desirably reduced the risk of developing hyperkalemia. These data demonstrate that CKD and/or CVD may be treated by administration of microporous zirconium silicate along with standard therapies that include diuretic according to the present invention.

In one embodiment, the present invention involves administration of a suitable dose of microporous zirconium silicate to a patient who has been diagnosed with chronic kidney disease. In another embodiment, the present invention involves administration of a suitable dose of microporous zirconium silicate to a patient who has been diagnosed with cardiovascular disease or after a myocardial infarction. In one aspect of this embodiment, the patient is diagnosed with both CKD and CVD.

The dosage of the composition may range from approximately 1-20 grams of ZS, preferably 8-15 grams, more preferably 10 grams. In another embodiment, the composition is administered at a total dosage range of approximately 1-60 gram, preferably 24-45 grams, more preferably 30 grams. The composition comprises a microporous structure composed of $ZrO_3$ octahedral units and at least one $SiO_2$ tetrahedral units and $GeO_2$ tetrahedral units. These structures have the empirical formula:

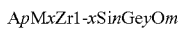

$A_pM_xZr_{1-x}Si_nGe_yO_m$ where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$. The germanium can substitute for the silicon, zirconium or combinations thereof. Since the compositions are essentially insoluble in bodily fluids (at neutral or basic pH), they can be orally ingested in order to remove toxins in the gastrointestinal system.

The compositions preferably have an elevated cation exchange capacity, particularly potassium exchange capacity. The elevated cation exchange capacity is achieved by a specialized process and reactor configuration that lifts and more thoroughly suspends crystals throughout the reaction as described in U.S. patent application Ser. No. 13/371,080 (U.S. Pat. Application Pub. No. 2012-0213847 A1). In an embodiment of the invention, the improved ZS-9 crystal compositions (i.e., compositions where the predominant crystalline form is ZS-9) had a potassium exchange capacity of greater than 2.5 meq/g, more preferably between 2.7 and 3.7 meq/g, more preferably between 3.05 and 3.35 meq/g. ZS-9 crystals with a potassium exchange capacity of 3.1 meq/g have been manufactured on a commercial scale and have achieved desirable clinical outcomes. It is expected that ZS-9 crystals with a potassium exchange capacity of 3.2 meq/g will also achieve desirable clinical outcomes and offer improved dosing forms. The targets of 3.1 and 3.2 meq/g may be achieved with a tolerance of ±15%, more preferably ±10%, and most preferably ±5%. Higher capacity forms of ZS-9 are desirable although are more difficult to produce on a commercial scale. Such higher capacity forms of ZS-9 have elevated exchange capacities of greater than 3.5 meq/g, more preferably greater than 4.0 meq/g, more preferably between 4.3 and 4.8 meq/g, even more preferably between 4.4 and 4.7 meq/g, and most preferably approximately 4.5 meq/g. ZS-9 crystals having a potassium exchange capacity in the range of between 3.7 and 3.9 meq/g were produced in accordance with Example 14 below.

In one embodiment, the composition exhibits median particle size of greater than 3 microns and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts has a diameter of less than 3 microns.

The median and average particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

In one embodiment, the composition exhibiting the median particle size and fraction of particles in the composition having a diameter less than 3 micron described above also exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible.

In one embodiment, the invention involves administering to a CKD and/or a CVD patient an individual pharmaceutical dosage comprising the composition in capsule, tablet, or powdered form. In another embodiment of the invention, the pharmaceutical product is packaged in a kit in individual unit dosages sufficient to maintain a lowered serum potassium level. The dosage may range from approximately 1-60 grams per day or any whole number or integer interval therein. Such dosages can be individual capsules, tablets, or packaged powdered form of 1.25-20 grams of the ZS, preferably 2.5-15 grams of ZS, more preferably 5-10 grams of ZS. In another embodiment, the ZS may be a single unit dose of approximately 1.25-45 gram capsule, tablet or powdered package. In another embodiment, the product may be consumed once a day, three times daily, every other day, or weekly.

In one embodiment, the invention involves administering to a CKD and/or CVD patient a combination comprising a therapy that includes diuretic and a zirconium silicate. In another embodiment, the zirconium silicate can be a ZS-9 as described herein. In yet another embodiment, the diuretic can be a loop diuretic, a thiazine diuretic and/or a potassium sparing diuretic. In still another embodiment, a method of treating a CKD and/or CVD comprises administering therapies that include diuretics and a zirconium silicate of the present invention. In another embodiment, the treatment of CKD and/or CVD using diuretics and zirconium silicate may further comprise angiotensin converting enzyme inhibitors (ACE) or angiotensin receptor blockers (ARB).

BRIEF DESCRIPTION OF THE DRAWINGS

FIG. 2 shows particle size distribution of ZS-9 lot 5332-04310-A in accordance with Example 8.

FIG. 3 shows particle size distribution of ZS-9 lot 5332-15410-A in accordance with Example 8.

FIG. 4 shows particle size distribution of ZS-9 preclinical lot in accordance with Example 8.

FIG. 5 shows particle size distribution of lot 5332-04310A w/o screening in accordance with Example 9.

FIG. 6 shows particle size distribution of lot 5332-04310A 635 mesh in accordance with Example 9.

FIG. 7 shows particle size distribution of lot 5332-04310A 450 mesh in accordance with Example 9.

FIG. 8 shows particle size distribution of lot 5332-04310A 325 mesh in accordance with Example 9.

FIG. 9 shows particle size distribution of lot 5332-04310A 230 mesh in accordance with Example 9.

FIG. 10: XRD plot for ZS-9 prepared in accordance with Example 12.

FIG. 11: FTIR plot for ZS-9 prepared in accordance with Example 12.

FIG. 12: XRD plot for ZS-9 prepared in accordance with Example 14.

FIG. 13: FTIR plot for ZS-9 prepared in accordance with Example 14.

FIG. 14: Example of the Blank Solution Chromatogram

FIG. 15: Example of the Assay Standard Solution Chromatogram.

FIG. 16: Exemplary Sample Chromatogram.

FIG. 17: Reaction vessel with standard agitator arrangement.

FIG. 18: Reaction vessel with baffles for production of enhanced ZS-9

FIG. 19: Detail of baffle design for 200-L reaction vessel for production of enhanced ZS-9

FIG. 20: Treatment Period of ZS-9 in comparison to placebo over 48 hours after ingestion.

FIG. 21: Comparison of time of serum K decrease.

FIG. 22: Comparison of serum K increase following treatment.

FIG. 23: Rate of K excretion in urine.

FIG. 24: Daily urinary sodium excretion.

FIG. 25: XRD plot for H-ZS-9 prepared according to Example 20 batch 5602-26812

FIG. 26: XRD plot for H-ZS-9 prepared according to Example 20 batch 5602-28312

FIG. 27: XRD plot for H-ZS-9 prepared according to Example 20 batch 5602-29112

FIG. 28: XRD plot for H-ZS-9 prepared according to Example 20 batch 5602-29812

FIG. 29: XRD data for ZS crystals produced according to Example 20.

FIG. 30: XRD data showing ZS-8 impurities.

DETAILED DESCRIPTION OF THE EMBODIMENTS OF THE INVENTION

Figure 1:
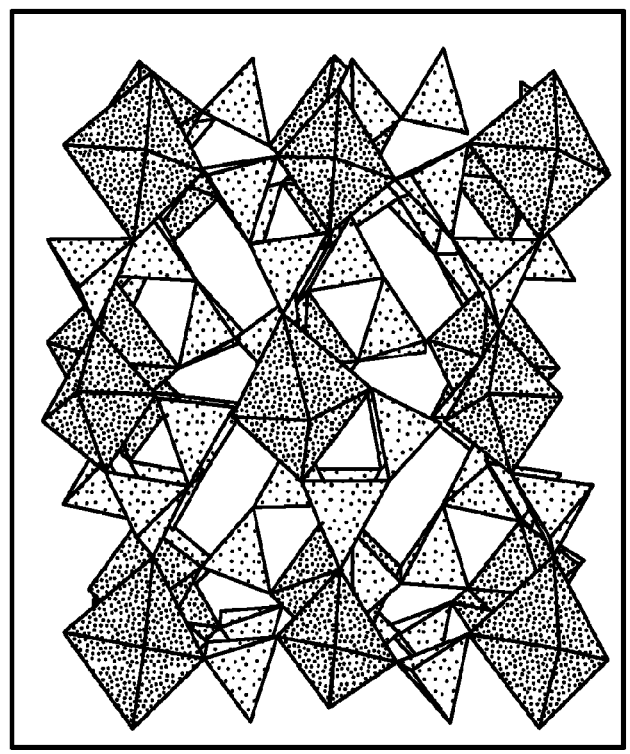
FIG. 1 is a polyhedral drawing showing the structure of microporous ZS Na2.19ZrSi3.01O9.11.2.71H2O (MW 420.71)

The inventors have discovered novel ZS molecular sieve absorbers that address problems of adverse effects in the therapeutic use of molecular sieve absorbers, e.g., for the treatment of hyperkalemia. ZS has a microporous framework structure composed of $ZrO_2$ octahedral units and $SiO_2$ tetrahedral units. FIG. 1 is a polyhedral drawing showing the structure of microporous ZS Na2.19ZrSi3.0109.11.2.71H2O (MW 420.71) The dark polygons depict the octahedral zirconium oxide units while the light polygons depict the tetrahedral silicon dioxide units. Cations are not depicted in FIG. 1.

The microporous exchanger of the invention has a large capacity and strong affinity, i.e., selectivity, for potassium or ammonium. Eleven types of ZS are available, ZS-1 through ZS-11, each having various affinities to ions have been developed. See e.g., U.S. Pat. No. 5,891,417. UZSi-9 (otherwise known as ZS-9) is a particularly effective ZS absorber for absorbing potassium and ammonium. These ZS have the empirical formula:

$$A_pM_xZr_{1-x}Si_nGe_yO_m. \quad (I)$$

where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and 1≤n+y≤12. The germanium can substitute for the silicon, zirconium or combinations thereof. It is preferred that x and y are zero or both approaching zero, as germanium and other metals are often present in trace quantities. Since the compositions are essentially insoluble in bodily fluids (at neutral or basic pH), they can be orally ingested in order to remove toxins in the gastrointestinal system. The inventors of the present invention have noted that ZS-8 has an increased solubility as compared to other forms of ZS (i.e., ZS-1-ZS-7, and ZSi-9-ZS-11). The presence of soluble forms of ZS including ZS-8 are undesirable since soluble forms of ZS may contribute to elevated levels of zirconium and/or silicates in the urine. Amorphous forms of ZS may also be substantially soluble. Therefore, it is desirable to reduce the proportion of amorphous material to the extent practicable.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

Generally, the hydrothermal process used to prepare the zirconium metallate or titanium metallate ion exchange compositions of this invention involves forming a reaction mixture which in terms of molar ratios of the oxides is expressed by the formulae:

$$aA_2O:bMO_{q/2}:1-bZrO_2:cSiO_2:dGeO_2:eH_2O$$

where "a" has a value from about 0.25 to about 40, "b" has a value from about 0 to about 1, "q" is the valence of M, "c" has a value from about 0.5 to about 30, "d" has a value from about 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture, it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water, acid or dilute acid and dried. Numerous drying techniques can be utilized including vacuum drying, tray drying, fluidized bed drying. For example, the filtered material may be oven dried in air under vacuum.

To allow for ready reference, the different structure types of the ZS molecular sieves and zirconium germanate molecular sieves have been given arbitrary designations of ZS-1 where the "1" represents a framework of structure type "1". That is, one or more ZS and/or zirconium germanate molecular sieves with different empirical formulas can have the same structure type.

The X-ray patterns presented in the following examples were obtained using standard X-ray powder diffraction techniques and reported in U.S. Pat. No. 5,891,417. The radiation source was a high-intensity X-ray tube operated at 45 Kv and 35 ma. The diffraction pattern from the copper K-alpha radiation was obtained by appropriate computer based techniques. Flat compressed powder samples were continuously scanned at 2° (2θ) per minute. Interplanar spacings (d) in Angstrom units were obtained from the position of the diffraction peaks expressed as 2θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of $100 \times I/I_o$, the above designations are defined as w=0-15; m=15-60; s=60-80 and vs=80-100.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The crystalline compositions of the instant invention may be characterized by their X-ray powder diffraction patterns and such may have one of the X-ray patterns containing the d-spacings and intensities set forth in the following Tables. The x-ray pattern for ZS-1, ZS-2, ZS-6, ZS-7, ZS-8, and ZS-11 as reported in U.S. Pat. No. 5,891,417, is as follows:

TABLE 1

ZS X-Ray powder diffraction patterns

| d(Å) | I |
|---|---|
| ZS-1 | |
| 7.7-8.6 | m |
| 6.3-7.0 | m |
| 5.5-6.3 | s |
| 4.7-5.5 | m |
| 3.2-4.0 | m |
| 2.6-3.4 | vs |
| ZS-2 | |
| 5.8-6.6 | m |
| 4.2-5.0 | w |
| 3.9-4.6 | m |
| 2.9-3.7 | m |
| 2.5-3.3 | vs |
| 2.3-3.0 | s |
| ZS-6 | |
| 6.1-6.9 | m |
| 4.4-5.1 | m |
| 3.4-4.2 | m |
| 3.3-4.1 | m |
| 2.3-3.1 | vs |
| 2.2-3.0 | w |
| ZS-7 | |
| 6.8-7.6 | vs |
| 5.6-6.4 | m |
| 3.7-4.5 | m |
| 3.6-4.4 | m |
| 2.6-3.4 | s-vs |
| 2.5-3.3 | m |
| 2.4-3.2 | vs |
| ZS-8 | |
| 12.0-13.2 | vs |
| 3.9-4.7 | m |
| 2.8-3.6 | m |
| 2.3-3.1 | m |
| 2.2-3.0 | w |
| 2.1-2.9 | w |
| ZS-11 | |
| 6.0-6.8 | w-m |
| 5.5-6.3 | m |
| 5.4-6.2 | vs |
| 5.2-6.0 | m |
| 2.7-3.5 | s |
| 2.5-3.3 | m |

The x-ray diffraction pattern for the high-purity, high KEC ZS-9 as made in accordance with Example 14 herein (XRD shown in FIG. 12), had the following characteristics d-spacing ranges and intensities:

TABLE 2

ZS-9

| d(Å) | I |
|---|---|
| 5.9-6.7 | m |
| 5.3-6.1 | m-s |
| 2.7-3.5 | vs |
| 2.0-2.8 | w-m |
| 1.6-2.4 | w |

The formation of ZS involves the reaction of sodium silicate and zirconium acetate in the presence of sodium hydroxide and water. The reaction has typically been conducted in small reaction vessels on the order of 1-5 Gallons. The smaller reaction vessels have been used to produce various crystalline forms of ZS including ZS-9. The inventors recognized that the ZS-9 being produced in these smaller reactors had an inadequate or undesirably low cation exchange capacity ("CEC").

The inventors have discovered that the use and proper positioning of a baffle-like structure in relation to the agitator within the crystallization vessel produces a ZS-9 crystal product exhibiting crystalline purity (as shown by XRD and FTIR spectra) and an unexpectedly high potassium exchange capacity. In smaller scale reactors (5-gal), cooling coils were positioned within the reactor to provide a baffle-like structure. The cooling coils were not used for heat exchange. Several types of cooling coils are available and the different designs may have some effect on the results presented herein, but the inventors used serpentine-type coils which snake along the inside wall of the reactor vessel.

The inventors found that the crystallization reaction used to produce ZS-9 particularly benefitted from baffles that when they are properly positioned relative to the agitator. The inventors initially produced ZS-9 with significant levels of undesirable ZS-11 impurity. See FIGS. 10-11. This incomplete reaction is believed to have resulted from significant amounts of solids remaining near the bottom of the reaction vessel. These solids near the bottom of the vessel remain even with conventional agitation. When properly positioned, the baffles and agitator improved the reaction conditions by creating forces within the reactor that lift the crystals within the vessel allowing for the necessary heat transfer and agitation to make a high purity form of ZS-9. In one embodiment, the baffles in combination with the agitator may be configured such that it provides sufficient lift throughout the entire volume regardless of the size of the reactor used. For example, if the reactor size is enlarged (e.g., 200 liter reactor) and the reaction volume is increased, the baffles will also be resized to accommodate the new reactor volume. FIGS. 12-13 show XRD and FTIR spectra of high purity ZS-9 crystals. As shown in Table 3 below, these crystals exhibit significantly higher levels of potassium exchange capacity ("KEC") than the less pure ZS-9 compositions. In an embodiment of the invention, the ZS-9 crystals had a potassium exchange capacity of between 2.7 and 3.7 meq/g, more preferably between 3.05 and 3.35 meq/g. ZS-9 crystals with a potassium exchange capacity of 3.1 meq/g have been manufactured on a commercial scale and have achieved desirable clinical outcomes. It is expected that ZS-9 crystals with a potassium exchange capacity of 3.2 meq/g will also achieve desirable clinical outcomes and offer improved dosing forms. The targets of 3.1 and 3.2 meq/g may be achieved with a tolerance of ±15%, more preferably ±10%, and most preferably ±5%. Higher capacity forms of ZS-9 are desirable although are more difficult to produce on a commercial scale. Such higher capacity forms of ZS-9 have elevated exchange capacities of greater than 3.5 meq/g, preferably greater than 4.0 meq/g, more preferably between 4.3 and 4.8 meq/g, even more preferably between 4.4 and 4.7 meq/g, and most preferably approximately 4.5 meq/g. ZS-9 crystals having a potassium exchange capacity in the range of between 3.7 and 3.9 meq/g were produced in accordance with Example 14 below.

Another unexpected benefit that came from using the reactor having a standard agitator in combination with baffles is that the high crystalline purity, high potassium exchange capacity ZS-9 crystals could be produced without utilizing any seed crystals. Prior attempts at making homogenous crystals having high crystalline purity of a single crystalline form have utilized seed crystals. The ability to eliminate the use of seed crystals was therefore an unexpected improvement relative to prior art processes.

As stated the microporous compositions of this invention have a framework structure of octahedral $ZrO_3$ units, at least one of tetrahedral $SiO_2$ units and tetrahedral $GeO_2$ units, and optionally octahedral $MO_3$ units. This framework results in a microporous structure having an intracrystalline pore system with uniform pore diameters, i.e., the pore sizes are crystallographically regular. The diameter of the pores can vary considerably from about 3 angstroms and larger.

As synthesized, the microporous compositions of this invention will contain some of the alkali metal templating agent in the pores. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. It is understood that the A' cation is different from the A cation. The methods used to exchange one cation for another are well known in the art and involve contacting the microporous compositions with a solution containing the desired cation (usually at molar excess) at exchange conditions. Typically, exchange conditions include a temperature of about 25° C. to about 100° C. and a time of about 20 minutes to about 2 hours. The use of water to exchange ions to replace sodium ions with hydronium ions may require more time, on the order of eight to ten hours. The particular cation (or mixture thereof) which is present in the final product will depend on the particular use and the specific composition being used. One particular composition is an ion exchanger where the A' cation is a mixture of $Na^+$, $Ca^{+2}$ and $H^+$ ions.

When ZS-9 is formed according to these processes, it can be recovered in the Na-ZS-9 form. The sodium content of Na-ZS-9 is approximately 12 to 13% by weight when the manufacturing process is carried out at pH greater than 9. The Na-ZS-9 is unstable in concentrations of hydrochloric acid (HCl) exceeding 0.2 M at room temperature, and will undergo structural collapse after overnight exposure. While ZS-9 is slightly stable in 0.2 M HCl at room temperature, at 37° C. the material rapidly loses crystallinity. At room temperature, Na-ZS-9 is stable in solutions of 0.1M HCl and/or a pH of between approximately 6 to 7. Under these conditions, the Na level is decreased from 13% to 2% upon overnight treatment.

The conversion of Na-ZS-9 to H-ZS-9 may be accomplished through a combination of water washing and ion exchange processes, i.e., ion exchange using a dilute strong acid, e.g., 0.1 M HCl or by washing with water. Washing with water will decrease the pH and protonate a significant fraction of the ZS, thereby lowering the weight fraction of Na in the ZS. It may be desirable to perform an initial ion exchange in strong acid using higher concentrations, so long as the protonation of the ZS will effectively keep the pH from dropping to levels at which the ZS decomposes. Additional ion exchange may be accomplished with washing in water or dilute acids to further reduce the level of sodium in the ZS. The ZS made in accordance with the present invention exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible. When protonated (i.e., low sodium) ZS is prepared in accordance with these techniques, the potassium exchange capacity is lowered relative to the un-protonated crystals. The ZS prepared in this way has a potassium exchange capacity of greater than 2.8. In a preferred aspect, the potassium exchange capacity is within the range of 2.8 to 3.5 meq/g, more preferably within the range of 3.05 and 3.35 meq/g, and most preferably about 3.2 meq/g. A potassium exchange capacity target of about 3.2 meq/g includes minor fluctuations in measured potassium exchange capacity that are expected between different batches of ZS crystals.

It has been found that when ZS crystals produced under optimal crystalline conditions are protonated, the protonation can result in a loss in cation exchange capacity. The inventors have discovered during scale up of the manufacturing process for ZS-9 that where crystallization conditions are less than optimal, the protonation of the produced ZS crystals results in an increased cation exchange capacity relative to the unprotonated form. The suboptimal crystallization conditions result for challenges of maintaining thorough agitation in a larger reaction vessel. For example, when increasing the size of the reaction vessel from a 50 gallons to 125 gallons, ZS-9 crystals with a crystalline impurities were produced. However, assessment of the KEC values for the protonated H-ZS-9 crystals utilizing this new method provided for greater than expected KEC's of greater than 3.1 meq/g, more preferably in the range of 3.2 to 3.5 meq/g.

The ion exchanger in the sodium form, e.g., Na-ZS-9, is effective at removing excess potassium ions from a patient's gastrointestinal tract in the treatment of hyperkalemia. When the sodium form is administered to a patient, hydronium ions replace sodium ions on the exchanger leading to an unwanted rise in pH in the patient's stomach and gastrointestinal tract. Through in vitro tests it takes approximately twenty minutes in acid to stabilize sodium ion exchanger.

The hydronium form typically has equivalent efficacy as the sodium form for removing potassium ions in vivo while avoiding some of the disadvantages of the sodium form related to pH changes in the patient's body. For example, the hydrogenated form has the advantage of avoiding excessive release of sodium in the body upon administration. This can mitigate edema resulting from excessive sodium levels, particularly when used to treat acute conditions. Further, patient who are administered the hydronium form to treat chronic conditions will benefit from the lower sodium levels, particularly patients at risk for congestive heart failure. Further, it is believed that the hydronium form will have the effect of avoiding an undesirable increase of pH in the patient's urine.

The present inventors have found that ZS compositions lacking added calcium can serve to withdraw excess calcium from patients which makes these compositions useful in the treatment of hyperkalemia in hypercalcemic patents as well as for the treatment of hypercalcemia. The calcium content of compositions prepared according to the process described in U.S. Provisional Application 61/670,415, incorporated by reference in its entirety, is typically very low—i.e., below 1 ppm. The present inventors have found that treatment of hyperkalemia with these compositions is also associated with removal of significant quantities of calcium from the patient's body. Therefore, these compositions are particularly useful for the treatment of hypercalcemic patients or hypercalcemic patients suffering from hyperkalemic.

The compositions of the present invention may be prepared by pre-loading the above-described ZS compositions with calcium ions. The pre-loading of the compositions with calcium results in a composition that will not absorb calcium when administered to patients. As an alternative, the ZS compositions may also be pre-loaded with magnesium.

The pre-loading of ZS with calcium (and/or magnesium) is accomplished by contacting the ZS with a dilute solution of either calcium or magnesium ions, preferably having a calcium or magnesium concentration range of about 10-100 ppm. The pre-loading step can be accomplished simultaneously with the step of exchanging hydronium ions with sodium ions as discussed above. Alternatively, the pre-loading step can be accomplished by contacting ZS crystals at any stage of their manufacture with a calcium or magnesium containing solution. Preferably, the ZS compositions comprise calcium or magnesium levels ranging from 1 to 100 ppm, preferably from 1 to 30 ppm, and more preferably between 5 and 25 ppm.

The pre-loading of ZS does not result in a reduction in potassium absorption capacity and therefore does not detract from the use of these compositions in the treatment of hyperkalemia. It is believed that due to their size, calcium and/or magnesium ions do not fully penetrate the pores of the ZS. Rather, the loaded calcium or magnesium remains only on the surface of the ZS. This added calcium or magnesium results in a composition that does not absorb calcium or magnesium from the patient's body and therefore is preferred for clinical use in the treatment of hyperkalemia.

In another embodiment, protonated ZS may be linked to hydroxyl-loaded anion exchanger such as zirconium oxide (OH—ZO), which help in the removal of sodium, potassium, ammonium, hydrogen and phosphate. Without being bound to a theory, the hydrogen released from the protonated ZS and hydroxide released from OH—ZO combine to form water, thus diminishing the concentration of "counter-ions" which diminish binding of other ions. The binding capacity of the cation and anion exchangers should be increased by administering them together. ZS of this form are useful for the treatment of many different types of diseases. In one embodiment, the compositions are used to remove sodium, potassium, ammonium, hydrogen and phosphate from the gut and from the patient with kidney failure.

The ZS-9 crystals have a broad particle size distribution. It has been theorized that small particles, less than 3 microns in diameter, could potentially be absorbed into a patient's bloodstream resulting in undesirable effects such as the accumulation of particles in the urinary tract of the patient, and particularly in the patent's kidneys. The commercially available ZS are manufactured in a way that some of the particles below 1 micron are filtered out. However, it has been found that small particles are retained in the filter cake and that elimination of particles having a diameter less than 3 microns requires the use of additional screening techniques.

The inventors have found that screening can be used to remove particles having a diameter below 3 microns and that removal of such particles is beneficial for therapeutic products containing the ZS compositions of the invention. Many techniques for particle screening can be used to accomplish the objectives of the invention, including hand screening, air jet screening, sifting or filtering, floating or any other known means of particle classification. ZS compositions that have been subject to screening techniques exhibit a desired particle size distribution that avoids potential complications involving the therapeutic use of ZS. In general, the size distribution of particles is not critical, so long as excessively small particles are removed. The ZS compositions of the invention exhibit a median particle size greater than 3 microns, and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts have a diameter of less than 3 microns. The median particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

The particle screening can be conducted before, during, or after an ion exchange process such as described above whereby the sodium content of the ZS material is lowered below 12%. The lowering of sodium content to below 3% can occur over several steps in conjunction with screening or can occur entirely before or after the screening step. Particles having a sodium content below 3% may be effective with or without screening of particles sizes as described herein.

In addition to screening or sieving, the desired particle size distribution may be achieved using a granulation or other agglomeration technique for producing appropriately sized particles.

In another embodiment, the ZS compositions may further comprise atoms or molecules attached onto their surfaces to produced grafted crystals. The grafted atoms or molecules are attached to the surface of the ZS, preferably through stable covalent bonds. In one embodiment, an organosilicate moiety is grafted onto the surface of the ZS composition through reacting active groups such as silanols (Si—O—H) on the surface of crystals. This may be accomplished, for example by using aprotic solvents. In another embodiment, an alkoxysilane may be grafted and would require the use of a corresponding alcohol to perform the reaction. Identifying free silanol groups on the surface can done through, for example by, Infrared spectroscopy. In another embodiment, if the material to graft lacks of the active groups on their surface, acid washes can be used to promote their formation. Following successful grafting, the ZS compositions may further comprise tagging the composition with radioactive isotopes, such as but not limited to C or Si. In an alternative embodiment, the ZS compositions may also comprise non-exchangeable atoms, such as isotopes of Zr, Si, or O, which may be useful in mass-balance studies.

It is also within the scope of the invention that these microporous ion exchange compositions can be used in powder form or can be formed into various shapes by means well known in the art. Examples of these various shapes include pills, extrudates, spheres, pellets and irregularly shaped particles. It is also envisioned that the various forms can be packaged in a variety of known containers. These might include capsules, plastic bags, pouches, packets, sachets, dose packs, vials, bottles, or any other carrying device that is generally known to one of skill in the art.

The microporous ion exchange crystals of this invention may be combined with other materials to produce a composition exhibiting a desired effect. The ZS compositions may be combined with foods, medicaments, devices, and compositions that are used to treat a variety of diseases. For example, the ZS compositions of the present invention may be combined with toxin reducing compounds, such as charcoal, to expedite toxin and poison removal. In another embodiment, the ZS crystals may exist as a combination of two or more forms of ZS of ZS-1 to ZS-11. In one embodiment, the combination of ZS may comprise ZS-9 and ZS-11, more preferably ZS-9 and ZS-7, even more preferably ZS-9, ZS-11, and ZS-7. In another embodiment of the present invention, the ZS composition may comprise a blend or mixture of ZS-9, wherein ZS-9 is present at greater than at least 40%, more preferably greater than at least 60%, even more preferably greater than or equal 70%, where the remainder may comprise mixtures of other forms of ZS crystals (i.e., ZS-1 to ZS-11) or other amorphous forms. In another embodiment, the blend of ZS-9 may comprise greater than about between 50% to 75% ZS-9 crystals and greater than about 25% to about 50% ZS-7 crystals with the remainder being other forms of ZS crystals, wherein the remainder of the ZS crystals does not include ZS-8 crystals.

As stated, these compositions have particular utility in adsorbing various toxins from fluids selected from bodily fluids, dialysate solutions, and mixtures thereof. As used herein, bodily fluids will include but not be limited to blood and gastrointestinal fluids. Also by bodily is meant any mammalian body including but not limited to humans, cows, pigs, sheep, monkeys, gorillas, horses, dogs, etc. The instant process is particularly suited for removing toxins from a human body.

The zirconium metallates can also be formed into pills or other shapes which can be ingested orally and pickup toxins in the gastrointestinal fluid as the ion exchanger transits through the intestines and is finally excreted. In one embodiment, the ZS compositions may be made into wafer, a pill, a powder, a medical food, a suspended powder, or a layered structure comprising two or more ZS. In order to protect the ion exchangers from the high acid content in the stomach, the shaped articles may be coated with various coatings which will not dissolve in the stomach, but dissolve in the intestines. In one embodiment, the ZS may be shaped into a form that is subsequently coated with an enteric coating or embedded within a site specific tablet, or capsule for site specific delivery.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium, sodium and magnesium sodium, calcium and hydronium ions, sodium, magnesium, and hydronium ions, or sodium calcium, magnesium, and hydronium ions. The relative amount of sodium and calcium can vary considerably and depends on the microporous composition and the concentration of these ions in the blood. As discussed above, when sodium is the exchangeable cation, it is desirable to replace the sodium ions with hydronium ions thereby reducing the sodium content of the composition.

ZS crystals as described in related U.S. application Ser. No. 13/371,080, which is incorporated by reference in its entirety, have increased cation exchange capacities or potassium exchange capacity. These increased capacity crystals may also be used in accordance with the present invention. The dosage utilized in formulating the pharmaceutical composition in accordance to the present invention will be adjusted according to the cation exchange capacities determined by those of skill in the art. Accordingly, the amount of crystals utilized in the formulation will vary based on this determination. Due to its higher cation exchange capacity, less dosage may be required to achieve the same effect.

The compositions of the present invention may be used in the treatment of diseases or conditions relating to elevated serum potassium levels. These diseases may include for example chronic or acute kidney disease, chronic, acute or sub-acute hyperkalemia. To those patients suffering from diseases or conditions with elevated serum potassium levels, the product of the present invention is administered at specific potassium reducing dosages. The administered dose may range from approximately 1.25-15 grams (~18-215 mg/Kg/day) of ZS, preferably 8-12 grams (~100-170 mg/Kg/day), more preferably 10 grams (~140 mg/Kg/day) three times a day. In another embodiment, the total administered dose of the composition may range from approximately 15-45 gram (~215-640 mg/Kg/day), preferably 24-36 grams (~350-520 mg/Kg/day), more preferably 30 grams (~400 mg/Kg/day). When administered to a subject, the composition of the present invention is capable of decreasing the serum potassium levels to near normal levels of approximately 3.5-5 mmol/L. The molecular sieves of the present product is capable of specifically removing potassium without affecting other electrolytes, (i.e., no hypomagnesemia or no hypocalcemia). The use of the present product or composition is accomplished without the aid of laxatives or other resins for the removal of excess serum potassium.

Acute hyperkalemia requires an immediate reduction of serum potassium levels to normal or near normal levels. Molecular sieves of the present invention which have a KEC in the range of approximately 1.3-2.5 meq/g would be capable of lowering the elevated levels of potassium to within normal range in a period of about 1-8 hours after administration. In one embodiment, the product of the present invention is capable of lowering the elevated levels in about at least 1, 2, 4, 6, 8, 10 hours after administration. The dose required to reduce the elevated potassium levels may be in the range of about 5-15 grams, preferably 8-12 grams, more preferably 10 grams. Molecular sieves having a higher KEC in the range of approximately 2.5-4.7 meq/g would be more efficient in absorbing potassium. As a result, the dose required to reduce the elevated potassium levels may be in the range of about 1.25-6 grams. The schedule of dose administration may be at least once daily, more preferably three times a day.

The treatment of chronic and sub-acute hyperkalemia will require maintenance dosing to keep potassium levels near or within normal serum potassium levels. As such, the administration of the product of the present invention will be lower than that prescribed to patients suffering from acute hyperkalemia. In one embodiment, compositions comprising molecular sieves having KEC in the range of approximately 2.5-4.7 meq/g will be scheduled for a dose in the range of approximately 1-5 grams, preferably 1.25-5 grams, preferably 2.5-5 grams, preferably 2-4 grams, more preferably 2.5 grams. Compositions comprising molecular sieves having a KEC in the range of approximately 2.5-4.7 meq/g will receive less and will be scheduled for a dose in the range of approximately 0.4-2.5 grams, preferably 0.8-1.6 grams, preferably 1.25-5 grams, preferably 2.5-5 grams, more preferably 1.25 grams. Compliance in this subset of patients is a major factor in maintaining normal potassium levels. As such, dosing schedule will therefore be an important consideration. In one embodiment, the dose will be given to patients at least three times a day, more preferably once a day.

One preferred aspect of the invention is its use of microporous zirconium silicate in the treatment of chronic kidney disease and/or chronic heart disease. The use of therapies comprising diuretics is common place in the treatment of chronic kidney disease and/or chronic heart disease. Prior attempts to treat these conditions by using therapies comprising diuretics led to undesirable effects such as hyperkalemia. The inventors have observed that administration of microporous zirconium silicate to patients suffering from chronic kidney disease and being administered therapies that included diuretics, experienced significant reduction in potassium levels without the negative effects. These negative effects were observed when therapies comprising diuretics were used in connection with ACE inhibitors and ARB therapy. The inventors have also unexpectedly observed that systemic aldosterone reduction is achieved through administration of microporous zirconium silicate without the negative effects of the aldosterone blockers.

These observations demonstrate that zirconium silicate according to the present invention will be effective in treating patients suffering from chronic kidney disease. Administration of microporous zirconium silicate to these patients currently on therapies that include diuretics reduces the risk of developing hyperkalemia and also reduces aldosterone without inducing hyperkalemia. The zirconium silicate can be administered alone or in combination with existing treatments that include diuretics or diuretics and ACE inhibitors and/or ARB therapy. Given the separate mechanism of action of zirconium silicate and ACE/ARB therapy, the administration of microporous zirconium silicate in conjunction with these therapies is expected to improve the effects upon the renin-angiotensin-aldosterone system (RAAS) and further mitigate the negative effects of aldosterone on CKD and CVD. The different mechanisms and independent aldosterone-lowering ability of microporous zirconium silicate are expected to result in at least additive and possibly synergistic interaction between the combined therapies.

In another embodiment, the diuretics may include any diuretic selected from the three general classes of thiazine or thiazine-like, loop diuretics, or potassium sparing diuretics. In one preferred embodiment, the diuretic is potassium sparing diuretic, such as spironolactone, eplerenone, canrenone (e.g., canrenoate potassium), prorenone (e.g., prorenoate potassium), and mexrenone (mextreoate potassium), amiloride, triamterene, or benzamil. The following are examples of possible diuretics that can be used in combination with microporous zirconium silicate according to the invention furosemide, bumetanide, torsemide, etacrynic acid, etozoline, muzolimine, piretanide, tienilic acid, bendroflumethiazide, chlorthiazide, hydrochlorthiazide, hydroflumethiazide, cyclopenthiazide, cyclothiazide, mebutizide, hydroflumethiazide, methyclothiazide, polythiazide, trichlormethiazide, chlorthalidone, indapamide, metolazone, quinethazone, clopamide, mufruside, clofenamide, meticrane, xipamide, clorexidone, fenquizone.

The following are examples of ACE inhibitors that can be used in combination with microporous zirconium silicate according to the invention: sulfhydryl-containing agents including captopril or zofenopril; dicarboxylate-containing agents including enalapril, ramipril, quinapril, perindopril, lisinopril, benazepril, imidapril, zofenopril, trandolapril; phosphate-containing agents including fosinopril; and naturally-occuring ACE inhibitors including casokinins and lactokinins. The following are examples of ARBs that can be used in combination with microporous zirconium silicate according to the present invention: valsartan, telmisartan, losartan, irbesartan, azilsartan, and olmesartan. Combinations of the above are particularly desirable. For example, a preferred method of treating CKD and/or CVD includes administration of microporous zirconium silicate, ramapril (ACE inhibitor) and telmisartan (ARB). For example, the invention may involve administration of microporous zirconium silicate in conjunction with combination therapy of ramapril/telmisartan to a patient diagnosed with chronic kidney disease. The ACE inhibitors and ARBs may be administered at their standard dose rates for the treatment of CKD, and in some instances at lower doses depending on the degree of synergy between the ACE inhibitor/ARBs in combination with microporous zirconium silicate.

Another approach to treating CKD and/or CVD involves administering microporous zirconium silicate with an aldosterone antagonist, i.e., an anti-mineralocorticoid. These agents are often used in adjunctive therapy for the treatment of chronic heart failure. Based on the observations of the inventor regarding the effects of microporour zirconium silicate on aldosterone, the combination of microporous zirconium silicate with an aldosterone antagonist may provide for additive and/or synergistic activity. Suitable aldosterone antagonists include spironolactone, eplerenone, canrenone (e.g., canrenoate potassium), prorenone (e.g., prorenoate potassium), and mexrenone (mextreoate potassium). The composition or product of the present invention may be formulated in a manner that is convenient for administration. For example, the composition of the present invention may be formulated as a tablet, capsule, powder, granule, crystal, packet, or any other dose form that is generally known to one of skill in the art. The various forms can be formulated as individual dosages comprising between 5-15 grams, preferably 8-12 grams, or more preferably 10 grams for multiple administrations per day, week or month; or they may be formulated as a single dosage comprising between 15-45 grams, preferably 24-36 grams, or more preferably 30 grams. In an alternative embodiment, the individual dosage form can be at least greater than 1, 2, 3, 4, 5, 6, 7, 8, 9, 10, 20, 30, or 40 grams. If the dosage form is tablet, it may be formulated as a granule, granule-like, or as an extended release form. Capsules may be formulated for administration three times a day, as a sprinkle, an extended release sprinkle, or a dose pack. Powders may be formulated for reconstitution, contained in plastic bags or packets. Those of skill in the art will recognize that the above description of dosage forms is not limiting and that other dosage forms for solids may be used to administer the product or composition of the present invention.

Surprisingly, the administration of the composition of the present invention at the specifically described dosing of approximately 10 grams (~140 mg/Kg/day) three times a day (i.e., 30 grams (~400 mg/Kg/day) total) is capable of reducing potassium levels in the serum for an extended duration of time. The inventors have found that when the product or composition of the present invention is administered at a dosage of approximately 10 grams three times a day, the effects of lowering serum potassium levels to within normal levels is sustained for 5 days after 2 days of acute therapy. It was expected, however, that the product of the present invention would be expelled in a relatively quick manner.

The ZS of the present invention may be modified and/or combined with other drugs or treatments if multiple conditions or diseases are present in a subject. For example, in one embodiment a subject may present with both hyperkalemia and chronic kidney disease, in which Na-ZS compositions may be used. In another embodiment, the ZS compositions used to treat chronic kidney disease may further comprise sodium bicarbonate in combination with protonated forms of the ZS. In another embodiment, subjects presenting with hyperkalemia and chronic heart failure may require the use of protonated ZS compositions. In another embodiment, the treatment of hyperkalemia and chronic heart disease will require no more than 10% sodium present in the ZS, more preferably less than 2% sodium.

In other embodiments of the invention, the ZS described herein may be further combined with activated carbon. The activated carbon has the effect of attracting organic molecules circulating within the system of a subject. See, e.g., HSGD Haemosorbents for Medical Device Applications, Nikolaev V. G. Presentation, London. As such, the combination of activated carbon with a ZS will act as a combination product having the ability to remove both excess potassium, and organic molecules. The activated carbon will comprise a multiplicity of adsorption pores of ranging from about 8 angstroms to about 800 angstroms in diameter, preferably at least about 50 angstroms in diameter. The ZS combined with activated carbon of the present invention will be useful in the treatment of many diseases and/or conditions requiring the removal of excess organic materials, such as but not limited to, lipids, proteins, and toxins. For example, the carbon containing ZS compositions of the present invention will be useful in the removal of pyrimidines, methylguanidines, guanidines, o-hydroxyhippuric acid, p-hydroxyhippuric acid, parathormone, purines, phenols, indols, pesticides, carcinogenic heterocyclic amines, conjugates of ascorbic acids, trihalomethanes, dimethylarginine, methylamines, organic chloramines, polyamines, or combinations thereof. The activated carbon combined with ZS will also be useful in adsorbing elevated levels of bile acids, albumin, ammonia, creatinine and bilirubin. To further improve the adsorption of activated carbon with coated ZS, the composition may be further coated with an albumin layer, a lipid layer, a DNA layer, a heparin layer, resulting in additional adsorption efficiencies ranging from about 12% to about 35%.

The activated carbon and ZS compositions will be useful in treating a subject presenting with multiple diseases or conditions, such as hyperkalemia, acute and chronic esogastritis, acute and chronic intestinal catarrhus, hyperacid gastritis, summer diarrhea, catarrhal jaundice, food related toxicoinfections, kidney disease, dysentery, choloera, typhoid, intestinal bacilli-carrier, heartburn, nausea, acute viral hepatitis, chronic active hepatitis and cirrhosis, concomitant hepatitis, mechanical jaundice, hepato-renal failure, hepatic coma, or combinations thereof.

In another embodiment, the ZS compositions described herein may be used in a variety of methods comprising administering to a subject in need thereof a composition described herein to remove excess levels of potassium. In another embodiment of the present invention, the method may include the administration of a combination of the ZS described herein and may further comprise additional compositions to aid in the removal of potassium while simultaneously removing other substances, such as but not limited to toxins, proteins, or ions, from the subject.

In order to more fully illustrate the invention, the following examples are set forth. It is to be understood that the examples are only by way of illustration and are not intended as an undue limitation on the broad scope of the invention as set forth in the appended claims.

Example 1

A solution was prepared by mixing 2058 g of colloidal silica (DuPont Corp. identified as Ludox™ AS-40), 2210 g of KOH in 7655 g H$_2$O. After several minutes of vigorous stirring 1471 g of a zirconium acetate solution (22.1 wt. % ZrO$_2$) were added. This mixture was stirred for an additional 3 minutes and the resulting gel was transferred to a stainless steel reactor and hydrothermally reacted for 36 hours at 200° C. The reactor was cooled to room temperature and the mixture was vacuum filtered to isolate solids which were washed with deionized water and dried in air.

The solid reaction product was analyzed and found to contain 21.2 wt. % Si, 21.5 wt. % Zr, K 20.9 wt. % K, loss on ignition (LOI) 12.8 wt. %, which gave a formula of K$_{2.3}$ZrSi$_{3.2}$O$_{9.5}$*3.7H$_2$O. This product was identified as sample A.

Example 2

A solution was prepared by mixing 121.5 g of colloidal silica (DuPont Corp. identified as Ludox® AS-40), 83.7 g of NaOH in 1051 g H$_2$O. After several minutes of vigorous stirring 66.9 g zirconium acetate solution (22.1 wt. % ZrO$_2$) was added. This was stirred for an additional 3 minutes and the resulting gel was transferred to a stainless steel reactor and hydrothermally reacted with stirring for 72 hours at 200° C. The reactor was cooled to room temperature and the mixture was vacuum filtered to isolate solids which were washed with deionized water and dried in air.

The solid reaction product was analyzed and found to contain 22.7 wt. % Si, 24.8 wt. % Zr, 12.8 wt. % Na, LOI 13.7 wt. %, which gives a formula Na$_{2.0}$ZrSi$_{3.0}$O$_{9.0}$*3.5H$_2$O. This product was identified as sample B.

Example 3

A solution (60.08 g) of colloidal silica (DuPont Corp. identified as Ludox® AS-40) was slowly added over a period of 15 minutes to a stirring solution of 64.52 g of KOH dissolved in 224 g deionized H$_2$O. This was followed by the addition of 45.61 g zirconium acetate (Aldrich 15-16 wt. % Zr, in dilute acetic acid). When this addition was complete, 4.75 g hydrous Nb$_2$O$_5$ (30 wt. % LOI) was added and stirred for an additional 5 minutes. The resulting gel was transferred to a stirred autoclave reactor and hydrothermally treated for 1 day at 200° C. After this time, the reactor was cooled to room temperature, the mixture was vacuum filtered, the solid washed with deionized water and dried in air.

The solid reaction product was analyzed and found to contain 20.3 wt. % Si, 15.6 wt. % Zr, 20.2 wt. % K, 6.60 wt. % Nb, LOI 9.32 wt. %, which give a formula of K$_{2.14}$Zr$_{0.7}$Nb$_{0.29}$ Si$_3$O$_{9.2}$*2.32H$_2$O. Scanning Electron (SEM) of a portion of the sample, including EDAX of a crystal, indicated the presence of niobium, zirconium, and silicon framework elements. This product was identified as sample C.

Example 4

To a solution prepared by mixing 141.9 g of NaOH pellets in 774.5 g of water, there were added 303.8 g of sodium silicate with stirring. To this mixture there were added dropwise, 179.9 g of zirconium acetate (15% Zr in a 10% acetic acid solution). After thorough blending, the mixture was transferred to a Hastalloy™ reactor and heated to 200° C. under autogenous pressure with stirring for 72 hours. At the end of the reaction time, the mixture was cooled to room temperature, filtered and the solid product was washed with a 0.001 M NaOH solution and then dried at 100° C. for 16 hours. Analysis by x-ray powder diffraction showed that the product was pure ZS-11.

Example 5

To a container there was added a solution of 37.6 g NaOH pellets dissolved in 848.5 g water and to this solution there were added 322.8 g of sodium silicate with mixing. To this mixture there were added dropwise 191.2 g of zirconium acetate (15% Zr in 10% acetic acid). After thorough blending, the mixture was transferred to a Hastalloy™ reactor and the reactor was heated to 200° C. under autogenous conditions with stirring for 72 hours. Upon cooling, the product was filtered, washed with 0.001 M NaOH solution and then dried at 100° C. for 16 hours. X-ray powder diffraction analysis showed the product to be ZS-9 (i.e., a composition that is predominately ZS-9 crystalline form).

Example 6

Approximately 57 g (non-volatile-free basis, lot 0063-58-30) of Na-ZS-9 was suspended in about 25 mL of water. A solution of 0.1N HCl was added gradually, with gentle stirring, and pH monitored with a pH meter. A total of about 178 milliliters of 0.1 N HCl was added with stirring, the mixture filtered then further rinsed with additional 1.2 liters 0.1 N HCl washes. The material was filtered, dried and washed with DI water. The pH of the resulting material was 7.0. The H-ZS-9 powder resulting from this three batch-wise ion exchange with 0.1 N HCl has <12% Na.

As illustrated in this example, batch-wise ion exchange with a dilute strong acid is capable of reducing the sodium content of a NA-ZS-9 composition to within a desired range.

Example 7

Approximately 85 gram (non-volatile-free basis, lot 0063-59-26) of Na-ZS-9 was washed with approximately 31 Liters of DI water at 2 Liter increments over 3 days until the pH of the rinsate reached 7. The material was filtered, dried and washed with DI water. The pH of the resulting material was 7. The H-ZS-9 powder resulting from batch-wise ion exchange and water wash has <12% Na.

As illustrated in this example, water washing is capable of reducing the sodium content of a NA-ZS-9 composition to within a desired range.

Example 8

Separate batches of ZS-9 crystals were analyzed using light scatter diffraction techniques. The particle size distribution and other measured parameters are shown in FIGS. 2-4. The d(0.1), d(0.5), and d(0.9) values represent the 10%, 50%, and 90% size values. The cumulative particle size distribution is shown in FIG. 4-6. As can be seen from the following figures, the cumulative volume of particles having a diameter below 3 microns ranges from approximately 0.3% to approximately 6%. In addition, different batches of ZS-9 have different particle size distributions with varying levels of particles having a diameter of less than 3 microns.

Example 9

Crystals of ZS-9 were subject to screening to remove small diameter particles. The resulting particle size distribution of the ZS-9 crystals screened using different size screens was analyzed. As illustrated in the following figures, the fraction of particles having a diameter below 3 microns can be lowered and eliminated using an appropriate mesh size screen. Without screening, approximately 2.5% percent of the particles had a diameter of below 3 microns. See FIG. 5. Upon screening with a 635 mesh screen, the fraction of particles having a diameter below 3 microns was reduced to approximately 2.4%. See FIG. 6. Upon screening with a 450 mesh screen, the fraction of particles having a diameter below 3 microns was reduced further to approximately 2%. See FIG. 7. When a 325 mesh screen is used, the fraction of particles having a diameter below 3 microns is further reduced to approximately 0.14%. See FIG. 8. Finally, a 230 mesh screen reduces the fraction of particles below 3 microns to 0%. See FIG. 9.

The screening techniques presented in this example illustrate that particle size distributions may be obtained for ZS-9 that provide little or no particles below 3 microns. It will be appreciated that ZS-9 according to Example 5 or H-ZS-9 according to Examples 6 and 7 may be screened as taught in this example to provide a desired particle size distribution. Specifically, the preferred particle size distributions disclosed herein may be obtained using the techniques in this example for both ZS-9 and H-ZS-9.

Example 10

A 14-Day repeat dose oral toxicity study in Beagle Dogs with Recovery was conducted. This GLP compliant oral toxicity study was performed in beagle dogs to evaluate the potential oral toxicity of ZS-9 when administered at 6 h intervals over a 12 h period, three times a day, in food, for at least 14 consecutive days. In the Main Study ZS-9 was administered to 3/dogs/sex/dose at dosages of 0 (control), 325, 650 or 1300 mg/kg/dose. An additional 2 dogs/sex/dose, assigned to the Recovery Study, received 0 or 1300 mg/kg/dose concurrently with the Main study animals and were retained off treatment for an additional 10 days. A correction factor of 1.1274 was used to correct ZS-9 for water content. Dose records were used to confirm the accuracy of dose administration.

During the acclimation period (Day −7 to Day −1) dogs were trained to eat 3 portions of wet dog chow at 6 h intervals. During treatment the requisite amount of test article (based on the most recently recorded body weight) was mixed with ~100 g of wet dog food and offered to the dogs at 6 h intervals. Additional dry food was offered following consumption of the last daily dose. Each dog received the same amount of wet dog feed. Body weights were recorded at arrival and on Days −2, −1, 6, 13 and 20. Clinical observations were performed twice daily during the acclimation, treatment and recovery periods. Wet and dry food consumption was measured daily during the treatment period. Blood and urine samples for analysis of serum chemistry, hematology, coagulation and urinalysis parameters were collected pretest (Day −1) and Day 13. Ophthalmologic examinations were performed pretest (Day −6/7) and on Day 7 (females) or 8 (males). Electrocardiographic assessments were performed pretest (Day −1) and on Day 11. At study termination (Day 14—Main Study and Day 24—Recovery Study), necropsy examinations were performed, protocol specified organ weights were weighed, and selected tissues were microscopically examined.

Oral administration of 325, 650 and 1300 mg ZS-9/kg/dose with food, three times a day at 6 h intervals over a 12-hour period for 14 days was well tolerated. Clinical signs were limited to the observation of white material, presumed to be test article, in the feces of some dogs at the 325 mg/kg/dose and in all animals receiving ≥650 mg/kg/dose during the second week of treatment. There were no adverse effects on body weight, body weight change, food consumption, hematology and coagulation parameters or ophthalmoscopic and ECG evaluations.

There were no macroscopic findings associated with administration of ZS-9. Microscopically, minimal to mild focal and/or multifocal inflammation was observed in the kidneys of treated animals but not in Control animals. The lesions had similar incidence and severity at 650 and 1300 mg/kg and were less frequent and severe at 325 mg/kg. In some dogs the inflammation was unilateral rather than bilateral and in some cases was associated with inflammation in the urinary bladder and origin of the ureter. Taken together these observations suggest that factors other than direct renal injury, such as alterations in urine composition of ZS-9-treated dogs may have resulted in increased susceptibility to subclinical urinary tract infections, even though no microorganisms were observed in these tissues. In recovery animals the inflammation was completely resolved in females and partly resolved in males suggesting that whatever the cause of the inflammation it was reversible following cessation of dosing.

The increased incidence of mixed leukocyte inflammation observed in Beagle dogs treated with ZS-9 is summarized below.

| Summary of Inflammation in Kidneys Terminal Necropsy (TN): Day 14 | | | | | | | | | |
|---|---|---|---|---|---|---|---|---|---|
| | | Dose | | | | | | | |
| | | 0 mg/kg | | 325 mg/kg | | 650 mg/kg | | 1,300 mg/kg | |
| | | Sex | | | | | | | |
| | | M | F | M | F | M | F | M | F |
| Number of Animals | | 3 | 3 | 3 | 3 | 3 | 3 | 3 | 3 |
| Left Kidney | Incidence | 0/3 | 0/3 | 0/3 | 2/3 | 2/3 | 3/3 | 3/3 | 3/3 |
| | minimal | 0/3 | 0/3 | 0/3 | 2/3 | 2/3 | 2/3 | 3/3 | 1/3 |
| | mild | 0/3 | 0/3 | 0/3 | 0/3 | 0/3 | 1/3 | 0/3 | 2/3 |
| Right Kidney | Incidence | 0/3 | 0/3 | 1/3 | 1/3 | 2/3 | 3/3 | 2/3 | 2/3 |
| | minimal | 0/3 | 0/3 | 1/3 | 1/3 | 2/3 | 1/3 | 2/3 | 0/3 |
| | mild | 0/3 | 0/3 | 0/3 | 0/3 | 0/3 | 2/3 | 0/3 | 2/3 |
| Both Kidneys | Incidence | 0/6 | 0/6 | 1/6 | 3/6 | 4/6 | 6/6 | 5/6 | 5/6 |
| | minimal | 0/6 | 0/6 | 1/6 | 3/6 | 4/6 | 3/6 | 5/6 | 1/6 |
| | mild | 0/6 | 0/6 | 0/6 | 0/6 | 0/6 | 3/6 | 0/6 | 4/6 |
| Sum of Severity Scores | | 0 | 0 | 2 | 3 | 4 | 9 | 5 | 9 |
| | | 0 | | 5 | | 13 | | 14 | |
| Mean Group Severity Scores | | 0.00 | | 0.83 | | 2.17 | | 2.33 | |

Minimal acute urinary bladder inflammation and unidentified crystals were also observed in the renal pelvis and urine of females dosed at 650 mg/kg/dose as summarized below

| Summary of Crystals observed at the 650 mg/kg/dose | | | |
|---|---|---|---|
| Animal No | 4420 | 4421 | 4422 |
| Unidentified crystals in urine | + | − | + |
| Crystals in renal pelvis | − | + | − |
| Urinary bladder acute inflammation | + | + | − |

Crystals were not identified in group 2 or 4 females or in any ZS-9 treated males.

In both studies it was noted that urinary pH was elevated compared to control and it was postulated that the change in urinary pH and/or urinary composition affected urine solute solubility resulting in crystal formation that caused urinary tract irritation and/or increased susceptibility to urinary tract infections (UTIs).

The description of the urinary crystals (long thin spiky clusters) coupled with the particle size profile and insolubility of test article make it very unlikely that these crystals are ZS-9.

Example 11

Crystals of ZS-9 are prepared and designated "ZS-9 Unscreened." Screening in accordance with the procedures of Example 10 is conducted on a sample of ZS-9 crystals and the screened sample is designated "ZS-9>5 µm." Another sample of Crystals of ZS-9 undergo an ion exchange in accordance with the procedures of Example 6 above and are then screened in accordance with the procedures of Example 10. The resulting H-ZS-9 crystals are designated "ZS-9+>5 µm."

The following 14-day study is designed to show the effect of particle size and particle form on the urinary pH and presence of crystals in the urine. The compounds above are administered to beagles orally by mixing with wet dog food. The regimen is administered 3 times a day at 6 hour intervals over a 12 hour period in the following manner:

Study Design

| Group | mg/kg/dose* | Female |
|---|---|---|
| Control | 0 | 3 |
| ZS-9 Unscreened | 600 | 3 |
| ZS-9 >5 µm | 600 | 3 |
| ZS-9 + >5 µm | 600 | 3 |
| ZS-9 Unscreened | 100 | 3 |
| ZS-9 >5 µm | 100 | 3 |
| ZS-9 + >5 µm | 100 | 3 |
| NaHCO$_3$ | 50 | 3 |

*uncorrected for water
ZS-9+ = pH neutral crystal

| | |
|---|---|
| Total number of dogs | 24 females |
| Age | 5 months of age on arrival |
| Acclimation | ≥10 days |
| Test Article Formulation | Mixed with wet dog food |
| Test article administration | Within 30 minutes of administration |
| Dose Formulation Analysis | Dose records will be used to confirm dosing. Weight of any remaining wet food will be recorded. |

The following table outlines the observations, toxicokinetic evaluation, laboratory investigation (hematology, urinalysis), and terminal procedures.

| OBSERVATIONS | |
|---|---|
| Mortality & Signs of ill health or reaction to treatment | Twice daily (after treatment and evening) including feces assessment |
| Detailed Exam | During acclimation, weekly on study |
| Body Weights | Arrival, Day −1, Day 7 and 14 |
| Food Consumption | Daily (Wet and Dry food) |
| Ophthalmoscopy | None |

-continued

| TOXICOKINETIC (FOR POTENTIAL ZR ANALYSIS) | |
|---|---|
| 3 X 1 ml whole blood/sample with sample weights recorded | Day −1: Pre-dose<br>Day 13: Pre-dose and 4 h post 2$^{nd}$ dose |

| LABORATORY INVESTIGATIONS | |
|---|---|
| Hematology/Clinical chemistry (see list) | Pretreatment and during Weeks 1 and 2 on study |
| Urinalysis (see list) | Pretreatment and during Weeks 1 and 2 on study (Metabolic cage, urine sample to be kept cool)<br>Remaining urine aliquoted and retained frozen for possible future Zr analysis |

| Terminal Procedures | |
|---|---|
| Necropsy | All Animals regardless of mode of death.<br>All tissues collected into NBF (see list) |
| Histopathology | Urinary tract only (Kidney and bladder) |

During this study in female dogs, the test articles, ZS-9 unscreened, ZS-9>5 µm, and ZS-9+>5 µm, were administered three times daily at 6 hour intervals over a 12-hour period for 14 consecutive days via dietary consumption utilizing a wet food vehicle. The dose levels were 100 or 600 mg/kg/dose.

All animals survived the 14-day administration period. There were no test article-related changes in mortality, body weight, body weight gain, organ weights, macroscopic findings, or on clinical chemistry or blood gas parameters. ZS-9 related findings were limited to an increase in the fractional excretion of sodium and an increase in urinary pH in animals receiving screened or unscreened ZS-9 at a dose of 6000 mg/kg/dose, and decreases in the fractional excretion of potassium and the urinary urea nitrogen/creatinine ratio in animals dosed at 600 mg/kg/dose ZS-9 unscreened, ZS-9>5 µm, and ZS-9+>5 µm.

Statistically significant increases in urinary pH compared to Control in animals treated with 600 mg/kg/dose of ZS-9 unscreened and ZS-9>5 µm, that was not observed at the 100 mg/kg/dose or in animals treated with 600 mg/kg/dose of ZS-9+>5 µm. Mean urinary pH in these animals increased from 5.33 to ~7.67 on Day 7 and from 5.83 to 7.733 on Day 13. The lack of effect on urinary pH in animals treated with 600 mg/kg/dose of protonated ZS-9 (ZS-9+>5 µm) suggests that the increase in the urinary pH in animals treated with the higher dose of sodium loaded ZS-9 (ZS-9 unscreened and ZS-9>5 µm) was a result of gastrointestinal hydrogen absorption.

All differences found in urine volume and specific gravity were considered within an acceptable range for normal biological and/or procedure-related variability. There were some variations between treatment groups among biochemical (protein, ketones, etc.) and microscopic (crystals, blood cells, etc.) urinary components that were also considered within an acceptable range for biological and/or procedure-related variability. Triple phosphate crystals (magnesium ammonium phosphate) were observed in most animals at all study intervals, rarely calcium oxalate dihydrate crystals were also observed in a few animals. Both of these crystal types are considered a normal finding in dogs. No patterns were observed to suggest that any of the crystals observed were treatment or test article-related in any animal. No unidentified crystals were observed in the urinary sediment of any animal.

On Days 7 and 13 the fractional excretion of sodium was increased relative to predose intervals in all groups including controls. Animals receiving 600 mg/kg/dose ZS-9 unscreened, ZS-9>5 μm, and ZS-9+>5 μm tended to have increases that were slighter greater (up to 116% relative to controls) than those seen in other treatment groups or among the control animals. The increases observed in these three groups occasionally reached magnitudes that were considered above expected ranges and were attributed to the test article. No discernible differences between the changes observed in these three groups could be identified. There was no difference in the fractional excretion of sodium in animals treated with 600 mg/kg/dose of the protonated ZS-9. These changes were attributed to the test article and were not considered toxicologically adverse.

Significant decreases in the fractional excretion of potassium, relative to Control, were observed in animals treated with 600 mg/kg/dose ZS-9 unscreened, ZS-9>5 μm, and ZS-9+>5 μm, and 100 mg/kg/dose ZS-9>5 μm on Days 7 and 13. Most of these values reached statistical significance relative to controls on Days 7 and 13. These decreases were attributed to the pharmacological effect of the test article.

On Days 7 and 13 urea nitrogen/creatinine ratio was mildly increased relative to predose intervals in all groups including controls. There were mild decreases in urea nitrogen/creatinine ratios on Days 7 and 13 in animals receiving 600 mg/kg/dose ZS-9 unscreened, ZS-9>5 μm, and ZS-9+>5 μm relative to controls (up to 26%). Most of the changes observed in these four groups reached statistical significance compared to controls for Days 7 and 13 although group mean values did not differ appreciably when compared to their respective pretest values. These findings were considered test article-related. Although there were occasional statistically significant differences among other endpoints, no test article-related effects on creatinine clearance, calcium/creatinine ratio, magnesium/creatinine ratio, or urine osmolality were identified in any treatment group.

Test article related microscopic findings in the kidney were observed at the 600 mg/kg/dose. The most common findings were minimal to mild mixed leukocyte infiltrates (lymphocytes, plasma cells, macrophages and/or neutrophils), and minimal to mild renal tubular regeneration (slightly dilated tubules lined by attenuated epithelial cells, epithelial cells with plump nucleus and basophilic cytoplasm). Minimal pyelitis (infiltration of neutrophils, lymphocytes and plasma cells in the submucosa of the renal pelvis) and minimal renal tubular degeneration/necrosis (tubules lined by hypereosinophilic cells with either pyknotic or karyorrhectic nucleus and containing sloughed epithelial cells and/or inflammatory cells in the lumen) were observed in ⅓ dogs receiving 600 mg/kg/dose ZS-9 unscreened and ⅓ dogs receiving 600 mg/kg/dose ZS-9>5 μm. Minimal pyelitis and mixed leukocyte infiltration in the urethra or ureter were also present in some dogs given ZS-9>5 μm.

The changes in the kidney were mostly present in the cortex and occasionally in the medulla with a random, focal to multifocal (up to 4 foci) distribution. These foci were variably sized, mostly irregular, occasionally linear (extending from the outer cortex to the medulla), and involved less than 5% of the kidney parenchyma in a given section. Most of these foci consisted of minimal to mild infiltration of mixed leukocytes with minimal to mild tubular regeneration, some foci had only minimal to mild tubular regeneration without the mixed leukocyte infiltrate. A few of these foci (two dogs given 600 mg/kg/dose ZS-9 unscreened and one dog given 600 mg/kg/dose ZS-9>5 μm) contained a small number of tubules with degeneration/necrosis. Pyelitis was present in four dogs (one given ZS-9 unscreened 600 mg/kg/dose and three given ZS-9>5 μm at 600 mg/kg/dose).

The infiltration of mixed leukocytes was also present in the submucosa of both ureters in dogs given 600 mg/kg/dose ZS-9>5 μm and the submucosa of the urethra in animals given 600 mg/kg/dose ZS-9 unscreened, 600 mg/kg/dose ZS-9>5 μm. The incidence and/or severity of mixed leukocyte infiltrates in the kidney parenchyma were higher in dogs with pyelitis compared to the dogs without pyelitis. The presence of pyelitis and/or the mixed leukocyte infiltrates in the urethra and ureters in some dogs and the multifocal, random distribution of kidney findings with inflammatory infiltrates are reminiscent of an ascending urinary tract infection and suggest that the kidney findings at the 600 mg/kg/dose are likely an indirect effect of the test article.

In dogs given ZS-9 unscreened at 600 mg/kg/dose, kidneys in two of the three dogs were affected with one or more of the aforementioned findings. All three dogs given ZS-9>5 μm at 600 mg/kg/dose had kidney lesions including pyelitis and mixed leukocyte infiltrates in the submucosa of urethra or ureters. Dogs given ZS-9+>5 μm at 600 mg/kg/dose, minimal mixed leukocyte infiltrate with tubular regeneration was present in only the left kidney in one dog while another dog had a few foci of minimal tubular regeneration.

Test article-related findings (direct or indirect) were not present in female dogs given ZS-9 unscreened at 100 mg/kg/dose (ZS-9, ZS-9>5 μm, ZS-9+>5 μm). An occasional focus or two of minimal tubular regeneration were present in three of the animals without an evidence of mixed leukocyte infiltrate or tubular degeneration/necrosis. Similar focus/foci of tubular regeneration were also present in a control female dog. The foci of tubular regeneration observed in female dogs given lower doses of ZS-9 unscreened were slightly smaller and were not associated with either mixed leukocyte infiltrates or tubular degeneration/necrosis. There was no evidence of crystals in any of the sections examined. Tubular mineralization in the papilla and glomerular lipidosis are background findings in beagle dogs and were not considered test article-related.

ZS-9 unscreened, ZS-9>5 μm, and ZS-9+>5 μm at the 600 mg/kg/dose had minimal to mild mixed leukocyte infiltrates in the kidney sometimes associated with minimal to mild renal tubular regeneration, and occasionally minimal renal tubular degeneration/necrosis, minimal mixed leukocyte infiltrates in ureter and/or urethra and minimal pyelitis in dogs dosed with ZS-9 unscreened and ZS-9>5 μm.

The lack of increased urinary pH in dogs treated with 600 mg/kg/dose ZS-9+>5 μm coupled with the reduced incidence of microscopic findings in these dogs and dogs treated with 600 mg/kg/dose ZS-9 unscreened supplemented with potassium suggest that elevated urinary pH and/or removal of potassium due to the pharmacological action of the test article, may have increased susceptibility to the background insult from urinary crystals and bacteria.

Based on these results, the no-observable-effect-level (NOEL) was 100 mg/kg/dose ZS-9 unscreened, ZS-9>5 μm, and ZS-9+>5 μm. The no-observable-adverse-effect-level (NOAEL) was established for ZS-9 unscreened at 600 mg/kg/dose, screened ZS-9 (ZS-9>5 μm) at 600 mg/kg/dose, and screened and protonated ZS-9 (ZS-9+>5 μm) at 600 mg/kg/dose.

Example 12

ZS-9 crystals were prepared by reaction in a standard 5-G crystallization vessel.

The reactants were prepared as follows. A 22-L Morton flask was equipped with an overhead stirrer, thermocouple, and an equilibrated addition funnel. The flask was charged with deionized water (3.25 L). Stirring was initiated at approximately 100 rpm and sodium hydroxide (1091 g NaOH) was added to the flask. The flask contents exothermed as the sodium hydroxide dissolved. The solution was stirred and cooled to less than 34° C. Sodium silicate solution (5672.7 g) was added. To this solution was added zirconium acetate solution (3309.5 g) over 43 minutes. The resulting suspension was stirred for another 22 minutes. Seed crystals of ZS-9 (223.8 g) were added to the reaction vessel and stirred for approximately 17 minutes.

The mixture was transferred to a 5-G Parr pressure vessel with the aid of deionized water (0.5 L). The vessel had smooth walls and a standard agitator. The reactor did not have a cooling coil present. The vessel was sealed and the reaction mixture was stirred at approximately 275-325 rprn and heated to 185+/−10° C. over 4 hours, then held at 184-186° C. and soaked for 72 hours. Finally, the reactants were then cooled to 80° C. over 12.6 hours. The resulting white solid was filtered with the aid of deionized water (18 L). The solids were washed with deionized water (125 L) until the pH of the eluting filtrate was less than 11 (9.73). The wet cake was dried in vacuo (25 inches Hg) for 48 hours at 95-105° C. to give 2577.9 g (107.1%) of ZS-9 as a white solid.

The XRD plot of the ZS-9 obtained in this example is shown in FIG. 10. The FTIR plot of this material is shown in FIG. 11. These XRD and FTIR spectra are characterized by the presence of absorption peaks typically associated with the ZS-11 crystalline form. In addition, the peaks that are associated with ZS-9 exhibit significant spreading due to crystal impurities (e.g. the presence of ZS-11 crystals in a ZS-9 composition). For example, the FTIR spectra shows significant absorption around 764 and 955 cm$^{-1}$. The XRD plot for this example exhibits significant noise and poorly defined peaks at 2-theta values of 7.5, 32, and 42.5.

Example 13

In this example ZS-9 crystals were protonated.

To a 100 L reaction vessel deionized water is charged (15.1 L) with vacuum and agitation (60-100 rpm). ZS-9 crystals (2.7 kg) were added to the 100 L vessel containing deionized water and allowed to reaction for a period of 5-10 minutes. Initial pH readings were recorded.

In a separate 50 L carboy, a hydrochloric acid solution is prepared comprising the steps of charging the carboy with deionized water (48 L) followed by hydrochloric acid (600 ml). To the 100 L reaction vessel, the hydrochloric acid solution is charged over a period of 1.5-2 hours. Hydrochloric acid solution was added to the reaction mixture until the pH reached a range of approximately 4.45-4.55. The reaction mixture was continually mixed for an additional period of 30-45 minutes. If the pH was greater than 4.7, additional hydrochloride solution was added until the pH was in the range of approximately 4.45-4.55. The reaction was allowed to stir for an additional 15-30 minutes.

The protonated ZS-9 crystals were filtered through Buchner funnel fitted with a 2 micron stainless steel mesh screen of approximately 18 inches in diameter. The filter cake formed was rinsed three times with approximately 6 L of deionized water to remove any excess hydrochloric acid. The filter cake containing the protonated crystals were dried in an vacuum oven at approximately 95-105° C. for a period of 12-24 hours. Drying was continued until the percent difference in net weight loss is less than 2% over greater than a 2 hour period. Once the product achieved appropriate dryness, the crystals were samples for quality.

Example 14

High capacity ZS-9 crystals were prepared in accordance with the following representative example.

The reactants were prepared as follows. A 22-L Morton flask was equipped with an overhead stirrer, thermocouple, and an equilibrated addition funnel. The flask was charged with deionized water (8,600 g, 477.37 moles). Stirring was initiated at approximately 145-150 rpm and sodium hydroxide (661.0 g, 16.53 moles NaOH, 8.26 moles Na2O) was added to the flask. The flask contents exothermed from 24° C. to 40° C. over a period of 3 minutes as the sodium hydroxide dissolved. The solution was stirred for an hour to allow the initial exotherm to subside. Sodium silicate solution (5,017 g, 22.53 mole SO2, 8.67 moles Na2O) was added. To this solution, by means of the addition funnel, was added zirconium acetate solution (2,080 g, 3.76 moles Zr02) over 30 min. The resulting suspension was stirred for an additional 30 min.

The mixture was transferred to a 5-G Parr pressure vessel Model 4555 with the aid of deionized water (500 g, 27.75 moles). The reactor was fitted with a cooling coil having a serpentine configuration to provide a baffle-like structure within the reactor adjacent the agitator. The cooling coil was not charged with heat exchange fluid as it was being used in this reaction merely to provide a baffle-like structure adjacent the agitator.

The vessel was sealed and the reaction mixture was stirred at approximately 230-235 rprn and heated from 21° C. to 140-145° C. over 7.5 hours and held at 140-145° C. for 10.5 hours, then heated to 210-215° C. over 6.5 hours where the maximum pressure of 295-300 psi was obtained, then held at 210-215° C. for 4 1.5 hours. Subsequently, the reactor was cooled to 45° C. over a period of 4.5 hours. The resulting white solid was filtered with the aid of deionized water (1.0 KG). The solids were washed with deionized water (40 L) until the pH of the eluting filtrate was less than 11 (10.54). A representative portion of the wet cake was dried in vacuo (25 inches Hg) overnight at 100° C. to give 1,376 g (87.1%) of ZS-9 as a white solid.

The XRD plot of the ZS-9 obtained is shown in FIG. 12. The FTIR plot of this material is shown in FIG. 13. These XRD and FTIR spectra, when compared to those for Example 12 (FIGS. 10-11), exhibited well-delineated peaks without spreading and the absence of peaks associated with crystalline forms other than ZS-9 (e.g., ZS-11 peaks). This example illustrates how the presence of a baffle-like structure within the reactor drastically and unexpectedly improves the quality of the thus obtained crystals. Although not wishing to be bound by theory, the inventors understand that baffles provide added turbulence which lifts the solids (i.e., crystals) and results in a more even suspension of crystals within the reaction vessel while the reaction is ongoing. This improved suspension allows for more complete reaction to the desired crystalline form and reduces the presence of unwanted crystalline forms of ZS in the end product.

Example 15

The KEC of ZS (ZS-9) was determined according to the following protocol.

This test method used a HPLC capable of gradient solvent introduction and cation exchange detection. The column was an IonPac CS12A, Analytical (2×250 mm). The flow rate was 0.5 mL/minute with a run time of approximately 8 minutes. The column temperature was set to 35° C. The injection volume was 10 µL and the needle wash was 250 µL. The pump was operated in Isocratic mode and the solvent was DI water.

A stock standard was prepared by accurately weighing and recording the weight of about 383 mg of potassium chloride (ACS grade), which was transferred into a 100-rnL plastic volumetric flask. The material was dissolved and diluted to volume with diluent followed by mixing. The stock standard had a $K^+$ concentration of 2000 ppm (2 mg/mL). Samples were prepared by accurately weighing, recording, and transferring about 112 mg of ZS-9 into a 20 mL plastic vial. 20.0 mL of the 2000 ppm potassium stock standard solution was pipetted into the vial and the container was closed. The sample vials were placed onto a wrist action shaker and were shook for at least 2 hours but not more than 4 hours. The sample preparation solution was filtered through a 0.45 pm PTFE filter into a plastic container. 750 pL of the sample solution was transferred into a 100-mL plastic volumetric flask. The sample was diluted to volume with DI water and mixed. The initial $K^+$ concentration was 15 ppm (1 SpgImL).

The samples were injected into the HPLC. FIG. 14 shows an example of the blank solution chromatogram. FIG. 15 shows an example of the assay standard solution chromatogram. FIG. 16 shows an exemplary sample chromatogram. The potassium exchange capacity was calculated using the following formula:

$$KEC = \frac{\frac{(IC - FC) \times V}{Eq\ wt.}}{Wt_{SPL} \times \frac{(100\% - \%\ Water)}{100\%} \times \frac{1\ g}{1000\ mg}}$$

KEC is the potassium exchange capacity in mEq/g. The initial concentration of potassium (ppm) is IC. The final concentration of potassium (ppm) is FC. The equivalent weight (atomic weight/valence) is Eq wt. The volume (L) of standard in sample preparation is V. The weight of ZS-9 (mg) used for sample preparation is $Wt_{sp1}$. The percent (%) of water content (LOD) is % water.

Three samples of ZS-9 produced in accordance with the procedures of Example 12, i.e., in a reactor without baffles (e.g., internal cooling coil structure), were tested for potassium exchange capacity (KEC) in accordance with the above-referenced procedure. Likewise, three samples of ZS-9 produced in accordance with Example 14 in a reactor having cooling coils serving as baffles were tested in accordance with this procedure. The results in Table 3 below show that the procedure of Example 14 and the presence of baffles within the crystallization vessel resulted in a dramatic increase in the potassium exchange capacity.

TABLE 3

| Potassium Exchange Capacity (KEC) | | | |
|---|---|---|---|
| Example 12 (Without baffles) | | Example 14 (With baffles) | |
| Lot 5368-10311A | 2.3 meq/gm | Lot 2724-9A | 3.9 meq/gm |
| Lot 5368-12211A | 1.7 meq/gm | Lot 2724-13D | 3.8 meq/gm |
| Lot 5368-13811A | 1.8 meq/gm | Lot 2724-18F | 3.8 meq/gm |

The high capacity ZS prepared in accordance with Example 14 will, upon protonation using the techniques of Example 13, have a slightly lower potassium exchange capacity. The protonated ZS prepared in this way has been found to have a potassium exchange capacity of about 3.2 meq/g. Accordingly, the high capacity ZS has been found to increase the capacity of the protonated form prepared using this process. This demonstrates that protonated ZS can be prepared having a potassium exchange capacity within the range of 2.8 to 3.5 meq/g, more preferably within the range of 3.05 and 3.35 meq/g, and most preferably about 3.2 meq/g.

Example 16

The use of an internal cooling coil to provide a baffle-like structure within the reactor is only feasible for small reactors on the order of 5-gallons because larger reactors cannot be easily fitted with, and typically do not utilized, cooling coils.

The inventors have designed a reactor for larger-scale production of high purity, high-KEC ZS-9 crystals. Large-scale reactors typically utilize a jacket for achieving heat transfer to the reaction chamber rather than coils suspended within the reaction chamber. A conventional 200-L reactor 100 is shown in FIG. 17. The reactor 100 has smooth walls and an agitator 101 extending into the center of the reaction chamber. The reactor 100 also has a thermowell 102 and a bottom outlet valve 103. The inventors have designed an improved reactor 200, FIG. 18, which also has an agitator 201, thermowell 202, and bottom outlet valve 203. The improved reactor 200 has baffle structures 204 on its sidewalls, which in combination with the agitator 201 provide significant lift and suspension of the crystals during reaction and the creation of high purity, high KEC ZS-9 crystals. The improved reactor can also include a cooling or heating jacket for controlling the reaction temperature during crystallization in addition to the baffle structures 204. The details of an exemplary and non-limiting baffle design is shown in FIG. 19. Preferably the reactor has a volume of at least 20-L, more preferably 200-L or more, or within the range of 200-L to 30,000-L. In an alternative embodiment, the baffle design may be configured to extend the Example 17

The several dosages of ZS-9 were studied in the treatment of human subjects suffering from hyperkalemia. A total of 90 subjects were enrolled in the study. The study involved three stages with dose escalation of the ZS in each stage. The ZS-9 used in these studies was prepared in accordance with Example 12. The ZS-9 crystals of an appropriate size distribution were obtained by air fractionation to have a distribution of crystals where greater than or equal to 97% are larger than 3 microns. The screening is such that the ZS crystals exhibit a median particle size of greater than 3 microns and less than 7% of the particles in the composition have a diameter less than 3 microns. The ZS-9 crystals were determined to have a KEC of approximately 2.3 meq/g. The protonation is such that the ZS crystals exhibit a sodium content below 12% by weight. The study utilized 3 g silicified microcrystaline cellulose, which are indistinguishable from ZS as the placebo.

Each patient in the study received either a 3 g dose of either the placebo or ZS three times daily with meals. Both ZS and Placebo were administered as a powder in water suspension that was consumed during meals. Each stage of the study had a 2:1 ratio between the number of subjects in the ZS cohort and placebo. In stage I, 18 patients were randomized to receive three daily doses of 0.3 g ZS or placebo with meals. In Stage II, 36 patients were randomized to receive three daily doses of 3 g ZS or placebo with meals. In Stage III, 36 patients were randomized to receive three daily doses of 10 g ZS placebo with meals. Altogether there were 30 patients that received placebo and 60 patients that received various doses of ZS. Diet was essentially unrestricted, and patients were allowed to choose which food items they wished from a variety of local restaurants or the standard in-house diet of the clinic.

The screening value for potassium ("K") was established on day 0 by measuring serum K three times at 30-minute intervals and calculating the mean (time 0, 30 and 60 minutes). The baseline K level was calculated as the mean of these values and the serum K on day one just before ingestion of the first dose. If the screening K value was less than 5.0 meq/1 the subject was not included in the study.

On study Days 1-2, all subjects received the study drug 3 times daily in conjunction with meals starting at breakfast (there was a delay of the first meal until 1.5 hours after the first dose on Day 1). Serum K levels were evaluated 4 hours after each dose for 48 hours following the initiation of treatment. If K levels became normal, the subject was discharged from the clinic at 48 hours without further study drug treatment. If K levels were still elevated (K>5.0 meq/1), subjects received another 24 hours of study drug treatment and then were re-assessed and discharged at 72 hours or 96 hours. All subjects received a minimum of 48 hours of study drug treatment, but a few received up to 96 hours of study drug treatment. The primary efficacy endpoint of the study was the difference in the rate of change in potassium levels during the initial 48 hours of study drug treatment between the placebo treated subjects and the ZS treated subjects. Table 4 provides the p-values of the various cohorts at the 24 and 48 hour endpoints. Patients receiving 300 mg of the ZS three times daily had no statistical difference relative to placebo at either of the 24 and 48 hour endpoints. Patients receiving 3 grams of ZS demonstrated a statistical difference at only the 48 hour time period, suggesting that this particular dosing was relatively effective at lowering serum potassium levels. Unexpectedly, those patients receiving 10 grams of ZS three times daily demonstrated the greatest reduction in potassium levels in both concentration and in rate. The decrease in potassium was considerable in magnitude, with an approximate 0.5 meq/g reduction at the 3 gram dose and approximately 0.5-1 meq/g reduction at the 10 gram dosing.

TABLE 4

Primary endpoint: Serum potassium (mmol/l) exponential rate of change from 24 hours and 48 hours Intent-to-Treat Population (Primary endpoint at 48 hours)

| | Cohort 1 300 mg tid p-value | Cohort 2 3 g tid p-value | Cohort 3 10 g tid p-value |
|---|---|---|---|
| 24 hours | 0.7668 | 0.0737 | 0.1301 |
| 48 hours | 0.4203 | 0.0480 | <0.0001 |

Subjects were then followed for a total of 7 days (168 hours) with K measurements performed daily. 24 hour urine collections were performed on the day before the study (day 0) in all patients, and for as long as the patients ingested the test product. Table 5 provides the difference in the rate of change in serum potassium levels over 7 days of study between placebo treated subjects and the various cohorts. Patients receiving 300 mg of the drug had no statistically significant reduction in potassium levels relative to the placebo over the 7 day period. Patients receiving 3 grams of the drug had no statistically significant reductions in potassium levels after the initial 24 hour period. Patients receiving 3 grams of the drug had the most statistically significant reduction in serum potassium levels over the 7 day time course. These data suggests that when given at least 10 grams of ZS, an extended reduction of potassium is achieved, and that a single (i.e., 1 day) dose is suitable for significant reduction in potassium levels. It is also possible that dosages of 3, 4, or 5 grams may be effective at reducing the potassium levels when given once daily.

TABLE 5

Serum Potassium (mmol/l) over time in intent-to-treat population

| | Cohort 1 300 mg tid Unpaired t-test p-value | Cohort 2 3 gm tid Unpaired t-test p-value | Cohort 3 10 gm tid Unpaired t-test p-value |
|---|---|---|---|
| Baseline | | | |
| Day 1-30 Min Post $1^{st}$ | 0.566 | 0.604 | 0.356 |
| Day 1-1 Hr Post $1^{st}$ | 0.875 | 0.125 | 0.022 |
| Day 1-2 Hr Post $1^{st}$ (Fed Breakfast) | 0.231 | 0.688 | 0.160 |
| Day 1-4 Hr Post $1^{st}$ (Fed Lunch) | 0.640 | 0.774 | 0.232 |
| Day 1-4 Hr Post $2^{nd}$ | 0.219 | 0.415 | 0.072 |
| Day 1-4 Hr Post $3^{rd}$ | 0.603 | 0.365 | 0.025 |
| Day 2-0 Hr | 0.700 | 0.026 | 0.092 |
| Day 2-4 Hr Post $1^{st}$ | 0.675 | 0.136 | <0.001 |
| Day 2-4 Hr Post $2^{nd}$ | 0.891 | 0.044 | <0.001 |
| Day 2-4 Hr Post $3^{rd}$ | 0.783 | 0.064 | <0.001 |
| Day 2-20 Hr Post $1^{st}$ | 0.822 | 0.157 | <0.001 |
| Day 3-0 Hr | 0.914 | 0.074 | <0.001 |
| Day 4-0 Hr | 0.756 | 0.775 | 0.001 |
| Day 5-0 Hr | 0.404 | 0.595 | 0.001 |
| Day 6-0 Hr | 0.717 | 0.321 | 0.016 |
| Day 7-0 Hr | 0.217 | 0.476 | 0.065 |

Comparison of treatment groups demonstrated no significant difference in any parameters including: age, sex, weight, serum creatinine level, estimated Glomerular filtration rate ("GFR"), potassium levels, and cause of Chronic Kidney Disease ("CKD").

FIG. 20 shows changes in serum K in the first 48 hours after ingestion of the placebo, ZS at 0.3 g per dose (Cohort 1), ZS at 3 g per dose (Cohort 2) and ZS at 10 g per dose (Cohort 3). Slopes of K versus time for the patients administered ZS were significantly different from the placebo for Cohort 2 (0.5 meq/L/48 hours, P<0.05) and Cohort 3 (1 meq/L/48 hours P<0.0001).

The time to normalization of serum K was significantly less in Cohort 3 versus the placebo group (P=0.040). Results for the other Cohort groups were not significantly different from placebo. FIG. 21 compares the time to decrease of serum K by 0.5 meq/L for subjects administered ZS at the 10 g doses versus placebo. Time to decrease in serum K was significantly shorter in ZS administered subjects than in placebo (P=0.042).

The increase in serum K from 48 hours to 144 hours of the study was also examined after discontinuing the administration of the study drug. The rate of increase in serum K was roughly proportional to the rate of decrease in serum K during ingestion of the drug, as shown in FIG. 22.

Analysis of 24 hour urine K excretion demonstrated that there was a significant (P<0.002) decrease of approximately 20 meq/day in urinary K excretion for ZS at the 10 g dose, while excretion remained the same or increased in all other groups as shown in FIG. 23.

Analysis of the K/creatinine ratio in daily urine samples confirmed the same trends as in 24 hour urine K excretion. Cohort 3 had a downward trend in urinary K/creatinine ratio while the other Cohorts remained constant or increased. Separate analysis indicated no change in creatinine clearance or daily creatinine excretion in any of the groups during the study.

Analysis of the 24 hour urine samples also allowed calculation of the urinary daily sodium excretion. As shown in FIG. 24, sodium excretion was generally stable in all of the groups. Urinary sodium excretion appeared to rise more in Cohort 1 and Control patients than in Cohort 3 though there were no significant changes in any group.

Blood Urea Nitrogen ("BUN") was tested as a measure of the effect of ZS to bind ammonium which is generated by bacterial urease in the gut. There was a dose-related and statistically significant reduction in BUN from Study Day 2 to Study Day 7, mirroring that of serum K (p-values between 0.035 [Study Day 2] and <0.001 [Study Days 5-7]). This was also accompanied by a reduction in urine excretion of urea.

There was a statistically significant decrease in serum calcium that remained within the normal range (from 9.5 mg/dL to 9.05 mg/dL) at the 10 g three times daily dose of ZS (p-values from 0.047 to 0.001 on Study Days 2-6, but no subjects developed hypocalcemia; there were no significant changes in serum magnesium, serum sodium, serum bicarbonate or any other electrolytes at any dose level of ZS. There was a trend towards a reduction in serum creatinine, which became statistically significant on Study Day 6 (p=0.048). There were no dose-related changes in any other evaluated kidney parameters, including urinary sediment, estimated Glomerular filtration rate ("GFR") or the renal biomarkers NGAL and KIM-1.

This clinical trial, which was randomized and double-blind, demonstrates that ingestion of moderate amounts of ZS significantly decreases serum K levels in patients with Stage 3 CKD. No laxative agents were given with the ZS, so the removal of K was solely due to the binding of K in the gut by ZS, rather than due to effects of diarrhea.

Oral sodium polystyrene sulfonate ("SPS") therapy invariably causes sodium load to the patient. Sodium is released in 1:1 ratio of the binding of all cations (K, hydrogen, calcium, magnesium, etc.). ZS is loaded partly with sodium and partly with hydrogen, to produce a near physiologic pH (7 to 8). At this starting pH, there is little release of sodium and a some absorption of hydrogen during binding of K. Urinary excretion of sodium does not increase during ingestion of ZS and thus ZS use should not contribute to sodium excess in patients.

The rapidity of action of ZS on serum K and the effectiveness in diminishing K excretion in the urine is surprising at the maximum dose of about 10 g three times daily (about 30 g daily or about 0.4 g/kg/day). This also resulted in a fall in urinary K by the second day of about 40% from the baseline level. It thus appears that ZS is at least as effective in diminishing body K stores in humans as in animals, and possibly more so due to the high K concentration in human stool.

Another observation from this trial was the significant reduction in phosphate (11-12% lowered) over the course of the trial. These data imply that microporous zirconium silicate can be utilized in the treatment of hyperphosphatemia.

Example 18

High capacity ZS (ZS-9) is prepared in accordance with Example 14. The material is protonated in accordance with the techniques described in Example 13. The material has been screened such that the ZS crystals exhibit a median particle size of greater than 3 microns and less than 7% of the particles in the composition have a diameter less than 3 microns. The ZS crystals exhibit a sodium content below 12% by weight. The dosage form is prepared for administration to patients at a level of 5 g, 10 g, and 15 g per meal. The ZS in this example has an increased potassium exchange capacity of greater than 2.8. In a preferred aspect, the potassium exchange capacity is within the range of 2.8 to 3.5 meq/g, more preferably within the range of 3.05 and 3.35 meq/g, and most preferably about 3.2 meq/g. A potassium exchange capacity target of about 3.2 meq/g includes minor fluctuations in measured potassium exchange capacity that are expected between different batches of ZS crystals.

The ZS-9, when administered according to the protocol established in Example 17, will provide for a similar reduction in potassium serum levels. Because ZS-9 has an improved KEC, the dosing administered to the subject in need thereof will be lowered to account for the increased cation exchange capacity. Thus, to patients suffering from potassium levels elevated above the normal range, approximately 1.25, 2.5, 5, and 10 grams of the ZS-9 will be administered three times daily.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

Example 19

ZS (ZS-2) is prepared in accordance with known techniques of U.S. Pat. Nos. 6,814,871, 5,891,417, and 5,888,472, discussed above. The x-ray diffraction pattern for the ZS-2 has the following characteristics d-spacing ranges and intensities:

TABLE 6

| ZS-2 | |
| --- | --- |
| d(Å) | I |
| 5.8-6.6 | m |
| 4.2-5.0 | w |
| 3.9-4.6 | m |
| 2.9-3.7 | m |
| 2.5-3.3 | vs |
| 2.3-3.0 | s |

In one aspect of this example, the ZS-2 crystals are prepared using the reactor with baffles described in Example 14. The material is protonated in accordance with the techniques described in Example 13. The material has been screened such that the ZS crystals exhibit a median particle size of greater than 3 microns and less than 7% of the particles in the composition have a diameter less than 3 microns. The ZS crystals exhibit a sodium content below 12% by weight. The dosage form is prepared for administration to patients at a level of 5 g, 10 g, and 15 g per meal. The ZS-2 crystals prepared in accordance with this example are beneficial for reducing serum potassium and can be manufactured using the alternative techniques for making ZS-2. These alternative manufacturing techniques may provide advantages under certain circumstances.

Example 20

Several batches of protonated ZS crystals were prepared using the reactor described in Example 16.

The batches of the ZS crystals were generally prepared in accordance with the following representative example.

The reactants were prepared as follows. To a 200-L reactor, as shown in FIG. 17, sodium silicate (56.15 kg) was added and charged with deionized water (101.18 kg). Sodium hydroxide (7.36 kg) was added to the reactor and allowed to dissolve in the reactor in the presence of rapid stirring over a period of greater than 10 minutes until there was complete dissolution of the sodium hydroxide. Zirconium acetate (23 kg) was added to the reactor in the presence of continuous stirring and allowed to stir over a period of 30 minutes. The reactants were mixed at a rate 150 rpm with the reactor set to 210° C.±5° C. for a period of ≥60 hours.

After the reaction period, the reactor was cooled to 60° C.-80° C. and the slurry of reactants were filtered, washed and dried over a period of ≥4 hours at a temperature of approximately 100° C. To prepare the dried crystals for protonation, deionized water (46 L) was charged to re-slurry the crystals. A solution of 15% HCl (approximately 5 to 7 kg of the 15% HCl solution) was mixed with the slurry for a period of 25 to 35 minutes. Following the protonation reaction, the reactants were once again filter dried and washed with approximately ≥75 L of deionized water.

Exemplary details of several protonated ZS crystal batches produced utilizing the above described procedure are presented in Table 7:

TABLE 7

| | Lot Number | | | |
|---|---|---|---|---|
| | 5602-26812-A | 5602-28312-A | 5602-29112-A | 5602-29812-A |
| Yield (kg) | 16.60 | 16.65 | 16.61 | 16.14 |
| % Theoretical Yield | 95 | 94.5 | 94.7 | 92.2 |
| IP KEC | 3.35 | 2.9 | 2.46 | 2.92 |
| XRD highest | 28.9 | 28.9 | 28.9 | 28.9 |
| XRD 2nd highest | 15.5 | 15.5 | 15.5 | 15.5 |
| XRD 3rd highest | 26.2:13.9 | 26.1:13.9 | 26.2:26.2 | 26.2:26.2 |
| pH | 8.3 | 8.7 | 8.6 | 8.9 |
| % <3 um (2.50) | 0.4 | 1.27 | 1.52 | 3.08 |
| % <3 um (3.00) | 1.69 | 2.77 | 2.8 | 6.37 |
| Mean D(4,3) | 10.6 | 12.5 | 12.8 | 10.1 |
| KEC | 3.1 | 3.0 | 2.94 | 3.04 |

The XRD plot of the H-ZS-9 obtained above are provided in FIGS. 25-28. The XRD plots demonstrate that H-ZS-9 can be manufactured in commercially significant batch quantities having desired potassium exchange capacity. Lot 5602-26812-A attained the most uniform crystalline distribution. It was found that when crystallization conditions result in a highly uniform particle size distribution, the subsequent protonation step reduced the cation exchange capacity from 3.4 to 3.1 meq/g. In contrast, Lots 5602-28312-A, 5602-29112-A, and 5602-29812-A exhibited a less uniform particle size distribution. The less uniform particle size distribution resulted from increasing the fill ratio of the reactor. When fill ratios reached 80-90%, the particle size distributions became less uniform. Unexpectedly, however, the subsequent protonation of these lots resulted in a significant increase in the potassium exchange capacity. Because the reaction according to the invention can be run in a manner that increases potassium exchange capacity upon protonation, it is expected that higher capacity ZS-9 can be obtained in commercially significant quantities than otherwise would have been thought possible.

Phase quantification to determine the diffraction pattern of the various batches of protonated ZS crystal samples were also performed using the Rietveld method in a Rigaku MiniFlex600. Manufacturing procedures using the 200-L reactor produced the phase composition described in Table 8 and XRD data described in FIGS. 25-29.

TABLE 8

| Phase Composition (wt %) via Reitveld Analysis | | | | |
|---|---|---|---|---|
| Lot Number | ZS-9 | ZS-7 | ZS-8 | Amorphous Crystals |
| 5567-26812-A | 61.6 | 16.0 | | 22.3 |
| 5567-28312-A | 55.7 | 21.8 | | 22.5 |
| 5567-29112-A | 55.7 | 25.7 | | 18.6 |
| 5567-29812-A | 66.6 | 19.1 | | 14.3 |

The diffraction patterns for the batches produced provided a mixture of ZS-9 and ZS-7 crystals in additional to a series of amorphous crystals. It was found that ZS crystals made in the larger 200 L reactor according to the above processes resulted in no detectable levels of ZS-8 crystals and lower levels of amorphous material than previously produced. The absence of ZS-8 crystals is highly desirable due to the undesirably higher solubility of ZS-8 crystals and their attendant contribution to elevated levels of zirconium in urine. Specifically, levels of zirconium in the urine are typically around 1 ppb. Administration of zirconium silicate containing ZS-8 impurities has led to zirconium levels in the urine between 5 to 50 ppb. The presence of ZS-8 can be confirmed by XRD as shown in FIG. 30. The ZS-9 crystals according to this embodiment are expected to lower levels of zirconium in the urine by eliminating impurities of soluble ZS-8 and minimizing the amorphous content.

Example 21

The batches of protonated zirconium crystals described in Example 20 were used in studies to treat human subjects suffering from hyperkalemia. The ZS compositions were generally characterized as having a mixture of ZS-9 and ZS-7, where the ZS-9 was present at approximately 70% and the ZS-7 was present at approximately 28% (hereafter ZS-9/ZS-7). All of the characterized ZS-9/ZS-7 crystals lack detectable quantities of ZS-8 crystals. Subjects were administered the ZS-9/ZS-7 composition according the method described in Example 17. A summary of the results are provided in Table 9.

TABLE 9

Kidney Function Test using the ZS-9/ZS-7 composition

| Subject ID | Lab Test | Day 0 | Day 3 | Day 4 | Day 5 | Day 6 | Day 9 | Day 15 | Day 21 |
|---|---|---|---|---|---|---|---|---|---|
| 009-006 L-D | BUN | 64.6 | 71.3 | 77.2 | 80.7 | 82.5 | 78.1 | 64.4 | 63.7 |
|  | Creat | 2.37 | 2.38 | NA | NA | NA | 2.37 | 2.34 | 2.40 |
| 009-011 | BUN | 28.5 | 27.9 | 31.7 | 28.1 | 28.1 | 22.2 | 32.6 | 36.9 |
| CHR | Creat | 2.31 | 2.27 | NA | NA | NA | 2.21 | 2.32 | 2.54 |
| 009-014 | BUN | 18.6 | 15.6 | 16.1 | 15.6 | 14.4 | 15.6 | 18.5 | 18.9 |
| RWR | Creat | 1.11 | 1.13 | NA | NA | NA | 1.23 | 1.13 | 1.16 |
| 009-017 | BUN | 60.3 | 61.7 | 67.1 | 75.3 | 75.2 | 75.9 | 71.3 | 74.4 |
| SMK | Creat | 2.37 | 2.31 | NA | NA | NA | 2.31 | 2.29 | 2.61 |
| 009-019 | BUN | 51.4 | 41.9 | 44.8 | ND | 41.4 | 37.7 | 46.6 |  |
| GLS | Creat | 3.14 | 2.71 | NA | ND | NA | 2.33 | 2.85 |  |
| 009-022 | BUN | 87.3 | 103.3 | 101.6 | ND | 94.6 | 85.3 | 76.4 | 97.8 |
| JHR | Creat | 2.40 | 2.40 | NA | ND | NA | 2.50 | 1.93 | 3.00 |
| 009-023 | BUN | 42.3 | 39.5 | 36.3 | 39.9 | 36.5 | 37.9 | 37.4 | 33.5 |
| EEF | Creat | 2.50 | 2.48 | NA | NA | NA | 2.22 | 2.44 | 2.39 |
| 009-025 | BUN | 42.4 | 43.1 | 37.9 | ND | 28.2 | 25.9 | 31.3 |  |
| DHK | Creat | 2.35 | 2.09 | NA | ND | NA | 1.82 | 2.05 |  |
| 009-026 | BUN | 24.3 | 25.5 | 28.5 | ND | 27.1 | 29.1 | 35.4 |  |
| ABL | Creat | 2.02 | 2.04 | NA | ND | NA | 1.99 | 1.94 |  |
| 009-028 | BUN | 46.9 | 55 |  |  |  |  |  |  |
| GMS | Creat | 4.51 | 4.61 | NA | NA | NA |  |  |  |

Surprisingly, the glomerular filtration rate (GFR) for subjects administered the ZS-9/ZS-7 composition were unexpectedly higher relative to the patient's baseline. Without being bound to any particular theory, the inventors posit that the improved GFRs and lowered creatinine levels (see Table 9 above) are due to absence of the ZS-8 impurities in the ZS-9/ZS-7 composition. As is generally known in the prior art, ZS-8 crystals have been characterized as being more reactive and therefore able to "leach" into the system.

This clinical trial demonstrates that ingestion of moderate amounts of ZS-9/ZS-7 surprisingly and unexpectedly decreases creatinine levels in patients.

In addition, a dose-related reduction in S-creatinine levels and hence creatinine clearance and GFR (improvement in GFR) in the above Phase 2 study was also observed. These observations indicate a potentially beneficial effect of ZS on kidney function. This could be explained by a ZS induced reduction in aldosterone levels, secondary to reductions in S-K, as it is well known that chronic hyperaldosteronism tends to accelerate progression of CKD. This explanation is further supported by Example 22, which shows that aldosterone levels can be mediated by administration of microporous zirconium silicate. Further, the reduction in lack of observed hypokalemia is consistent with the reduction of aldosterone and the attendant lowering of potassium excretion in the urine.

Example 22

In a multi-week dog study (male and female), involving 100, 300, and 1000 mg/kg/dose levels (See Table 10 below), several important observations were made. The zirconium silicate according to this example had a content of 94% ZS-9, 4% ZS-7, and 2% amorphous zirconium silicate.

Blood Gas

At the Week 2 and Week 4 collections, both sexes receiving 1000 mg/kg/dose had minimal (occasionally statistically significant) increases in serum pH that were associated with minimal increases in bicarbonate (HCO3) (up to 1.2-fold), relative to controls. Minimal increases in tCO2 (up to 1.2-fold) were also present in these treatment groups. Similar changes were also noted at the Week 2 collection in males receiving 1000 mg/kg/dose+KCl, and at the Week 4 collection in females receiving 1000 mg/kg/dose+KCl. These findings were not considered biologically relevant given the small magnitude of changes. Furthermore, all values remained within expected ranges.

Hematology

There were no test article-related effects among hematology endpoints parameters in either sex at any interval, up to and including the terminal collection at Week 4. There were occasional statistical differences that were not considered test article-related or toxicologically meaningful due to their small magnitude, sporadic nature and/or lack of a dose response. All mean and individual values were considered within an acceptable range for biologic and/or procedure-related variation.

Clinical Chemistry

At the Week 2 and Week 4 collections, both sexes receiving 1000 mg/kg/dose had mild decreases in potassium (up to 23%) and phosphorus (up to 20%), relative to controls. Reductions in potassium and phosphorus were considered test article-related. There was also a tendency for bicarbonate to be minimally increased (up to 1.2-fold) in both sexes receiving 1000 mg/kg/dose at the Week 2 and Week 4 collections, relative to controls. Fluctuations in bicarbonate tended to correlate with alterations among blood gas data and urine pH (discussed below). Minimal increases in bicarbonate were also noted sporadically in other treatment groups at Week 4, including males receiving 100 mg/kg/dose, and females receiving 1000 mg/kg/dose+KCl and 1000 mg/kg/dose SID. Serum potassium, phosphorus and bicarbonate were similar to controls at the end of the Week 7 recovery interval in both sexes receiving 1000 mg/kg/dose.

At the Week 2 and Week 4 collections, females receiving 1000 mg/kg/dose had mild progressive increases in AST (2.3-fold) and ALT (3.3-fold), relative to controls. These changes were attributable to one of six individuals at Week 2 (Animal number 732), and two of six individuals at Week 4 (animal number 733 and 736). Elevations in AST and ALT did not correlate with microscopic changes in the liver, and given the sporadic nature of these findings, they were unlikely to be test article-related. At the pretest, Week 2 and Week 4 collections, there were mild progressive increases in alkaline phosphatase (ALP), aspartate aminotransferase (AST) and alanine aminotransferase (ALT) in males receiving 100 mg/kg/dose. These changes were attributable to one individual (animal number 716), and considered incidental. AST, ALT and ALP were similar to controls in both sexes receiving 1000 mg/kg/dose at the end of the Week 7 recovery interval. There were occasionally other mild fluctuations among clinical chemistry endpoints that were not considered test article-related or toxicologically meaningful due to their small magnitude, sporadic nature, and/or lack of a dose-response or correlative findings. All other individual and mean values were considered within an acceptable range for biologic and/or procedure-related variation.

Aldosterone

At the Week 4 collection, both sexes receiving 1000 mg/kg/dose had mild to moderate decreases in aldosterone concentration (up to 67%), relative to controls. Decreases in serum aldosterone were attributable to reductions in aldosterone biosynthesis secondary to test article-related decreases in serum potassium. Reductions in aldosterone resulted in alterations in renal potassium and sodium excretion (discussed below), and correlated with microscopic changes in the zona glomerulosa of the adrenal gland (intracytoplasmic lipid vacuolation and cystic degeneration). Similar changes in aldosterone were not noted in either sex receiving 1000 mg/kg/dose+KCl. At the Week 7 (recovery) collection, aldosterone was similar to controls in males receiving 1000 mg/kg/dose, but remained moderately decreased in one of three females receiving 1000 mg/kg/dose (animal number 736).

Urinalysis

At the Week 2 and Week 4 collections, both sexes receiving 1000 mg/kg/dose and 1000 mg/kg/dose+KCl had mild to moderate increases in urine volume (up to 3.3-fold) with concurrent decreases in urine specific gravity. These changes were considered test article related. There was a tendency for urine pH to mildly increase in these treatment groups, which correlated with alterations in serum bicarbonate. These changes were considered test article-related. Urine volume, specific gravity and pH were similar to controls at the end of the Week 7 recovery interval in both sexes receiving 1000 mg/kg/dose. Despite minor variations between treatment groups among physical (appearance), biochemical (protein, occult blood, etc.), and microscopic (erythrocytes, etc.) urinary components, there were no other test article-related effects among urinalysis parameters in either sex at any dose level. All other findings were within an acceptable range for biologic and procedure-related variation.

Urine Chemistry

As illustrated in the following table, there was a tendency for fractional excretion of potassium (Fe: K) to decrease in most treatment groups, relative to controls, indicative of reduced renal potassium excretion. These changes were generally minimal overall, and were not associated with meaningful changes in serum potassium, with the exception of both sexes receiving 1000 mg/kg/dose, and 1000 mg/kg/dose+KCl. Severe reductions in FE: K were noted in both sexes receiving 1000 mg/kg/dose, and were considered a compensatory response to reductions in serum potassium concentration. Conversely, mild increases in FE: K were noted in both sexes receiving 1000 mg/kg/dose+KCl. These treatment groups also had mild increases in fractional excretion of chloride (FE: Cl) (up to 3.2-fold), relative to controls. Increases in FE: K and FE: Cl were considered secondary to KCl supplementation.

In most treatment groups, there were mild to moderate increases in fractional excretion of sodium (FE: Na), relative to controls. These findings indicated increased renal sodium excretion, and were not associated with meaningful changes in serum sodium. Alterations in aldosterone (discussed previously) likely contributed to effects in renal sodium excretion.

There were also mild decreases in urine osmolality at Week 2 and Week 4, which mostly correlated with reductions in urine specific gravity, and increases in urine volume. These findings were typical of reduced urine concentration (discussed previously). At the Week 2 and Week 4 collections, urinary calcium excretion (calcium/creatinine ratio) was mildly increased (up to 7.5-fold) both sexes receiving 1000 mg/kg/dose, relative to controls. Alterations in urine calcium excretion did not result in notable effects on serum calcium concentrations. At the Week 7 recovery interval, there were no notable effects on urine chemistry endpoints in either sex receiving 1000 mg/kg/dose.

| | | Summary of Effects on Urinalysis Parameters[a] | | | | | | | | | |
|---|---|---|---|---|---|---|---|---|---|---|---|
| | | 100 mg/kg/dose (TID) | | 300 mg/kg/dose (TID) | | 1000 + KCl mg/kg/dose (TID) | | 1000 mg/kg/dose (TID) | | 1000 mg/kg/dose (SID) | |
| Endpoint | Interval | M | F | M | F | M | F | M | F | M | F |
| Urine Volume | Week 2 | — | — | — | — | ↑2.2 | ↑2.1 | ↑2.1 | ↑2.7[b] | — | — |
| | Week 4 | — | — | ↑1.3 | ↑1.4 | ↑1.4 | ↑1.5 | ↑1.6 | ↑3.3[b] | — | — |
| FE: Na | Week 2 | — | — | — | — | ↑4.2[b] | ↑3.3[b] | ↑3.8[b] | ↑2.8 | ↑2.4[b] | — |
| | Week 4 | — | — | ↑1.8[b] | — | ↑4.4[b] | ↑2.8[b] | ↑3.6[b] | ↑2.7[b] | ↑2.2[b] | — |
| FE: K | Week 2 | — | ↓30[b] | ↓23 | ↓30[b] | ↑1.8[b] | ↑1.5 | ↓95[b] | ↓96[b] | ↓29 | ↓43[b] |
| | Week 4 | ↓25 | ↓22 | — | ↓20 | ↑1.9[b] | ↑1.5 | ↓95[b] | ↓95 | ↓28[b] | ↓34[b] |
| Urine Osmolality | Week 2 | — | — | — | — | — | ↓27[b] | ↓52[b] | ↓64[b] | — | — |
| | Week 4 | — | — | — | — | — | — | ↓54[b] | ↓69[b] | — | — |

[a]Changes relative to controls
[b]Statistically significant
M: Male;
F: Female
↑: Fold-increase;
↓: Percent-decrease;
—: No meaningful change Fecal Occult Blood No definitive test article-related effects were noted on fecal occult blood analysis in any treatment group at the Week 4 or Week 7 recovery collections. A few individuals receiving the test article had a positive fecal occult blood test at the Week 4 collection, including one of three males at 300 mg/kg/dose, one of three males and one of three females at 1000 mg/kg/dose+KCl, two of six males and one of six females at 1000 mg/kg/dose, and one of five females at 1000 mg/kg/dose SID. At the Week 7 recovery interval, one of three females receiving 0 mg/kg/dose had a positive fecal occult blood test. Given the presence of a positive result in a control female and lack of correlative findings, positive results in individuals receiving the test article were likely spurious or diet-related.

The reduction in phosphorous observed in this trial is noteworthy because of the purity of the crystals. This reduction in phosphate was unexpected because it was not previously thought that zirconium silicate crystals (without substantial amorphous content) could effectively bind phosphate ions. These observations further demonstrate that the present invention, particularly the preferred crystals having very little amorphous content can be effectively used to treat hyperphospatemia as well as other conditions where hyperphosphatemia may be present, such as hyperkalemia, chronic kidney disease, and/or chronic heart disease.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

Example 23

Optimal use of cardio- and reno-protective renin-angiotensin-aldosterone system inhibitors (RAASi) is greatly limited by hyperkalaemia. Sodium (or calcium) polystyrene sulfonate (SPS/CPS) with or without sorbitol, has been used for controlling hyperkalemia but its efficacy is uncertain and has been reportedly associated with potentially serious adverse events (AEs), including sodium loading and colonic necrosis (Harel 2013; Sterns 2010). Thus, there is a need for a safe, well-tolerated and effective hyperkalaemia therapy. ZS-9, a nonabsorbed cation exchanger designed to specifically entrap excess potassium ($K^+$), significantly reduced serum $K^+$ vs placebo over 48 hr with excellent tolerability in patients with chronic kidney disease (CKD) and hyperkalaemia (Ash 2013). Here we report the safety of ZS-9 during a large, two-part Phase 3 hyperkalemia trial.

Patients (N=753) with serum $K^+$ 5-6.5 mmol/L were randomised (1:1:1:1:1) to ZS-9 (1.25 g, 2.5 g, 5 g or 10 g) or placebo thrice daily (TID) for 48 hr (acute phase), after which those with $K^+ \leq 4.9$ mmol/L (n=542) were either re-randomized 1:1 to the same dose of ZS-9 that was given during the acute phase or placebo once daily (QD), or (for placebo-treated patients) re-randomized to ZS-9 1.25 g or 2.5 g QD, for Day 3-15 (extended phase). AEs and serious AEs (SAEs) were recorded through study end.

Figure 31:
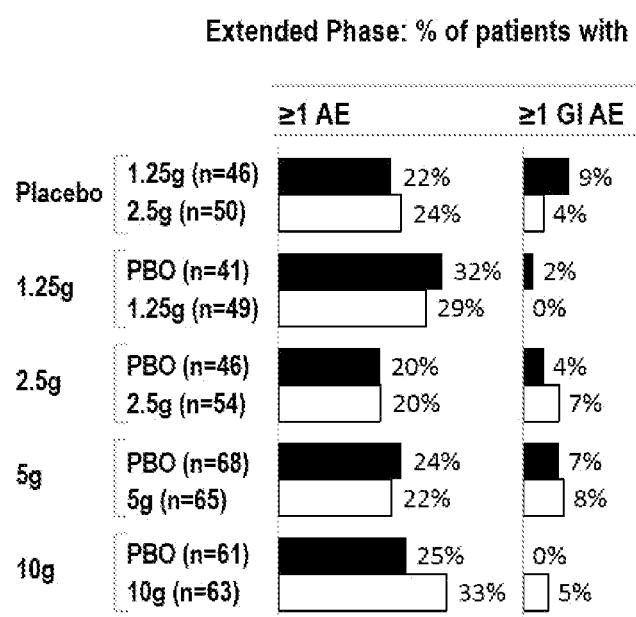
FIG. 31: The proportion of patients with ≥1 AE and ≥1 GI AE in the extended-treatment phase of the large, two-part Phase 3 hyperkalemia trial reported in Example 23.

At baseline, mean age was 65 yr. CKD, heart failure, or diabetes was 60%, 40% and 60% respectively. Two-thirds of patients were on concomitant RAASi. The proportion of patients with ≥1 AE and ≥1 GI AE in the ZS-9 dose groups was not significantly different compared with placebo in either the acute or extended-treatment phases. In the acute phase, the proportion of patients with ≥1 AE (≥1 GI AE) with ZS-9 1.25 g, 2.5 g, 5 g and 10 g was 16.2%, (4.5%), 9.2% (2.1%), 14.0% (3.8%), and 11.9% (3.5%), respectively, vs 10.8% (5.1%) with placebo. The most common (≥2% in any treatment group) GI AEs in the acute phase were diarrhea and constipation. One SAE (placebo) was reported during the acute phase. The proportion of patients with ≥1 AE and ≥1 GI AE in the extended-treatment phase is shown in FIG. 31. The number of patients with SAEs was low and similar for ZS-9 (3, 4, 3, and 0 patients each on ZS-9 1.25 g, 2.5 g, 5 g and 10 g, respectively) and placebo (5 patients) with extended treatment.

ZS-9 was well tolerated during 2 days of acute, thrice-daily treatment and 12 additional days of once-daily treatment. The incidence of GI AEs with ZS-9 was not significantly different from placebo in either phase, including at the highest doses of ZS-9. No SAEs were reported with ZS-9 in the acute phase and the number of patients with SAEs was similar vs placebo during extended treatment. Acute TID and extended QD dosing of ZS-9 was well tolerated and appeared to be safe in these high-risk patients with hyperkalaemia, potentially allowing optimal use of reno- and cardio-protective RAASi in patients who may benefit from such treatment.

Example 24

Therapies that affect the renin-angiotensin-aldosterone (RAAS) system increase the risk of hyperkalaemia (potassium [$K^+$]>5 mmol/L). Hyperkalaemia often prompts RAAS therapy discontinuation, despite its proven benefit in chronic kidney disease (CKD) and heart failure patients. There is an unmet need for safe, reliable, effective drugs that provide sustained $K^+$ reduction. ZS-9 is a novel, nonabsorbed cation exchanger designed to specifically entrap excess Kt Here we report changes in serum $K^+$ for the largest dose of ZS-9 (10 g) vs placebo in patients stratified by baseline RAAS use (ie, RAAS vs non-RAAS) from a Phase 3 trial of ZS-9.

In the acute phase, 753 patients with $K^+$ 5-6.5 mmol/L were randomised (1:1:1:1:1) to ZS-9 (1.25 g, 2.5 g, 5 g or 10 g) or placebo given three times daily (TID) with meals for 48 hours. In the extended efficacy phase, 542 patients who became normokalaemic (3.5-4.9 mmol/L) were re-randomised 1:1 to the same dose of ZS-9 received during the acute phase or placebo and treated once daily (QD) for 12 additional days. RAAS inhibitors were kept constant throughout the study.

Overall, 67% of patients were receiving RAAS therapy at baseline, of whom 66%, 36%, and 9%, were on an ACE, ARB, or spironolactone, respectively. At baseline mean $K^+$ values were 5.3 mmol/L in all subgroups (Table 1). At the end of the acute phase (ie, 48 hours after first dose), patients who received 10 g ZS-9 had significantly greater decreases in $K^+$ levels than did patients who received placebo, in both the RAAS (−0.7 vs −0.2 mmol/L, respectively; p<0.001) and non-RAAS (−0.7 vs −0.3 mmol/L, respectively; p<0.001) groups (Table 1).

TABLE 1

| | Mean (SD) acute phase $K^+$ values (mmol/L) | | | | |
|---|---|---|---|---|---|
| | | N | RAAS | N | Non-RAAS |
| Placebo | Baseline | 98 | 5.3 (0.36) | 60 | 5.3 (0.37) |
| | 48 hr | 98 | 5.1 (0.47) | 59 | 5.1 (0.49) |
| | Δ baseline | 98 | −0.2 (0.42) | 59 | −0.3 (0.41) |

TABLE 1-continued

Mean (SD) acute phase K+ values (mmol/L)

| | | N | RAAS | N | Non-RAAS |
|---|---|---|---|---|---|
| 10 g ZS-9 | Baseline | 95 | 5.3 (0.32) | 48 | 5.3 (0.38) |
| | 48 hr | 92 | 4.5 (0.48) | 48 | 4.5 (0.42) |
| | Δ baseline | 92 | −0.7 (0.49) | 48 | −0.7 (0.51) |
| | P-value (vs placebo) | | <0.001 | | <0.001 |

Extended efficacy phase baseline K+ values for ZS-9-treated and placebo-treated patients were similar in both the RAAS (4.5 vs 4.4 mmol/L, respectively) and non-RAAS groups (4.6 vs 4.4 mmol/l, respectively). On Day 15, change from extended phase baseline mean K+ levels were significantly smaller in ZS-9-treated patients than in placebo-treated patients, regardless of whether they were receiving RAAS or not (Table 2).

TABLE 2

Mean (SD) extended efficacy phase K+ values (mmol/L)

| Acute | Extended | | N | RAAS | N | Non-RAAS |
|---|---|---|---|---|---|---|
| 10 g ZS-9 | Placebo | Extended Phase Baseline | 39 | 4.4 (0.36) | 22 | 4.4 (0.34) |
| | | Day 15 | 38 | 5.0 (0.53) | 20 | 4.9 (0.43) |
| | | Δ baseline | 38 | 0.6 (0.53) | 20 | 0.6 (0.41) |
| | 10 g ZS9 | Extended Phase Baseline | 43 | 4.5 (0.46) | 20 | 4.6 (0.43) |
| | | Day 15 | 42 | 4.6 (0.49) | 19 | 4.6 (0.57) |
| | | Δ baseline | 42 | 0.1 (0.54) | 19 | 0.1 (0.63) |
| | | P-value (vs placebo) | | <0.001 | | 0.004 |

In the overall population, rates of adverse events were not significantly different in the ZS-9 10 g and placebo groups in both phases of the study.

These results show that ZS-9 was effective in decreasing K+ after 3 days of TID treatment and maintaining K+ levels with QD dosing in patients receiving RAAS therapy, results consistent with those in patients not on RAAS inhibitors. ZS-9 may become an important treatment for both correcting hyperkalaemia and importantly maintaining normokalaemia in a safe and well-tolerated manner. ZS-9 may enable optimal use of cardio- and reno-protective RAAS inhibitors in patients who may benefit from them.

The invention claimed is:

1. A method for treating chronic kidney or chronic heart disease comprising administering to a patient in need thereof a first agent selected from an angiotensin-converting enzyme (ACE) inhibitor or angiotensin receptor blocker (ARB), and a second agent comprising zirconium silicate of formula (I):

$$A_p M_x Zr_{1-x} Si_n Ge_y O_m \tag{I}$$

where

A is a potassium ion, sodium ion, rubidium ion, cesium ion, calcium ion, magnesium ion, hydronium ion or mixtures thereof, M is at least one framework metal, wherein the framework metal is hafnium (4+), tin (4+), niobium (5+), titanium (4+), cerium (4+), germanium (4+), praseodymium (4+), terbium (4+) or mixtures thereof, "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$, wherein the second agent is a zirconium silicate composition comprising ZS-9 and lacks detectable amounts of ZS-8.

2. The method of claim 1, wherein the first agent is an ACE inhibitor selected from captopril, zofenopril, enalapril, ramipril, quinapril, perindopril, lisinopril, benazepril, imidapril, zofenopril, trandolapril, fosinopril, or pharmaceutically acceptable salts thereof.

3. The method of claim 1, wherein the first agent is an ARB selected from valsartan, telmisartan, losartan, irbesartan, azilsartan, olmesartan, or pharmaceutically acceptable salts thereof.

* * * * *